US007601335B2

(12) United States Patent
McCutcheon et al.

(10) Patent No.: US 7,601,335 B2
(45) Date of Patent: Oct. 13, 2009

(54) PRETREATMENT OF A BIOLOGICAL SAMPLE FROM AN AUTOIMMUNE DISEASE SUBJECT

(75) Inventors: Krista McCutcheon, Burlingame, CA (US); An Song, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 307 days.

(21) Appl. No.: 11/437,296

(22) Filed: May 19, 2006

(65) Prior Publication Data

US 2006/0263349 A1 Nov. 23, 2006

Related U.S. Application Data

(60) Provisional application No. 60/682,990, filed on May 20, 2005.

(51) Int. Cl.
G01N 33/53 (2006.01)
(52) U.S. Cl. .............. 424/9.2; 435/7.21; 435/7.23; 435/7.24; 435/7.8; 435/962; 436/178; 436/824; 436/825
(58) Field of Classification Search ............. None
See application file for complete search history.

(56) References Cited

U.S. PATENT DOCUMENTS

| | | | |
|---|---|---|---|
| 4,690,905 A | 9/1987 | Diamond |
| 4,861,579 A | 8/1989 | Meyer et al. |
| 5,500,362 A | 3/1996 | Robinson et al. |
| 5,565,332 A | 10/1996 | Hoogenboom et al. |
| 5,573,905 A | 11/1996 | Lerner et al. |
| 5,595,721 A | 1/1997 | Kaminski et al. |
| 5,677,180 A | 10/1997 | Robinson et al. |
| 5,693,780 A | 12/1997 | Newman et al. |
| 5,721,108 A | 2/1998 | Robinson et al. |
| 5,736,137 A | 4/1998 | Anderson et al. |
| 5,776,456 A | 7/1998 | Anderson et al. |
| 5,843,398 A | 12/1998 | Kaminski et al. |
| 5,843,439 A | 12/1998 | Anderson et al. |
| 5,849,898 A | 12/1998 | Seed et al. |
| 6,015,542 A | 1/2000 | Kaminski et al. |
| 6,090,365 A | 7/2000 | Kaminski et al. |
| 6,120,767 A | 9/2000 | Robinson et al. |
| 6,171,586 B1 | 1/2001 | Lam et al. |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,287,537 B1 | 9/2001 | Kaminski et al. |
| 6,306,393 B1 | 10/2001 | Goldenberg |
| 6,368,596 B1 | 4/2002 | Ghetie et al. |
| 6,399,061 B1 | 6/2002 | Anderson et al. |
| 6,410,391 B1 | 6/2002 | Zelsacher |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,827 B1 | 5/2003 | Kaminski et al. |
| 6,652,852 B1 | 11/2003 | Robinson et al. |
| 6,682,734 B1 | 1/2004 | Anderson et al. |
| 6,726,909 B2 | 4/2004 | Williams |
| 6,737,056 B1 | 5/2004 | Presta |
| 6,846,476 B2 | 1/2005 | White |
| 6,893,625 B1 | 5/2005 | Robinson et al. |
| 6,896,885 B2 | 5/2005 | Hanna |
| 6,897,044 B1 | 5/2005 | Braslawsky et al. |
| 2001/0018041 A1 | 8/2001 | Hanna et al. |
| 2001/0056066 A1 | 12/2001 | Bugelski et al. |
| 2002/0004587 A1 | 1/2002 | Miller et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez |
| 2002/0012665 A1 | 1/2002 | Hanna |
| 2002/0041847 A1 | 4/2002 | Goldenberg |
| 2002/0058029 A1 | 5/2002 | Hanna |
| 2002/0128488 A1 | 9/2002 | Yamakawa et al. |
| 2002/0136719 A1 | 9/2002 | Shenoy et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026801 A1 | 2/2003 | Weiner et al. |
| 2003/0026804 A1 | 2/2003 | Grillo-Lopez et al. |
| 2003/0068664 A1 | 4/2003 | Albitar et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0133930 A1 | 7/2003 | Goldenberg et al. |
| 2003/0147885 A1 | 8/2003 | Anderson et al. |
| 2003/0157108 A1 | 8/2003 | Presta |
| 2003/0180292 A1 | 9/2003 | Hanna et al. |
| 2003/0185796 A1 | 10/2003 | Wolin et al. |
| 2003/0219433 A1 | 11/2003 | Hansen |
| 2003/0219818 A1 | 11/2003 | Bohen et al. |
| 2004/0093621 A1 | 5/2004 | Shitara et al. |
| 2004/0202658 A1 | 10/2004 | Benyunes |
| 2004/0213784 A1 | 10/2004 | Grillo-Lopez et al. |

(Continued)

FOREIGN PATENT DOCUMENTS

DE 10060686 6/2002

(Continued)

OTHER PUBLICATIONS

Christen et al., "Immune response to a recombinant human TNFR55-IgG1 fusion protein: auto-antibodies in rheumatoid arthritis (RA) and multiple sclerosis (MS) patients have neither neutralizing nor agonist activities" *Human Immunology* 60(9):774-790 (Sep. 1999).

(Continued)

*Primary Examiner*—David A Saunders
(74) *Attorney, Agent, or Firm*—Wendy M. Lee

(57) ABSTRACT

The present application describes a method for pretreating a biological sample from an autoimmune disease subject in order to avoid interference, especially where the sample is to be subjected to a cell-based biological activity assay, such as a neutralizing antibody assay.

22 Claims, 14 Drawing Sheets

U.S. PATENT DOCUMENTS

| | | | |
|---|---|---|---|
| 2005/0025764 | A1 | 2/2005 | Watkins et al. |
| 2005/0032130 | A1 | 2/2005 | Beresini et al. |
| 2005/0053602 | A1 | 3/2005 | Brunetta |
| 2005/0069545 | A1 | 3/2005 | Carr et al. |
| 2005/0079174 | A1 | 4/2005 | Barbera-Guillen et al. |
| 2005/0106108 | A1 | 5/2005 | Leung et al. |
| 2005/0112060 | A1 | 5/2005 | White |
| 2005/0123540 | A1 | 6/2005 | Hanna et al. |
| 2005/0123546 | A1 | 6/2005 | Umana et al. |
| 2005/0180972 | A1 | 8/2005 | Wahl et al. |
| 2005/0186216 | A1 | 8/2005 | Ledbetter et al. |
| 2006/0263349 | A1* | 11/2006 | McCutcheon et al. .... 424/131.1 |
| 2007/0099245 | A1* | 5/2007 | Gorovits et al. ........... 435/7.2 |

FOREIGN PATENT DOCUMENTS

| | | |
|---|---|---|
| EP | 0 332 865 A2 | 9/1989 |
| EP | 0 330 191 B1 | 10/1996 |
| WO | WO 92/21031 | 11/1992 |
| WO | WO 95/03770 | 2/1995 |
| WO | WO 98/56418 A2 | 12/1998 |
| WO | WO 98/58964 | 12/1998 |
| WO | WO 99/22764 | 5/1999 |
| WO | WO 99/51642 | 10/1999 |
| WO | WO 00/09160 | 2/2000 |
| WO | WO 00/20864 | 4/2000 |
| WO | WO 00/27428 | 5/2000 |
| WO | WO 00/27433 | 5/2000 |
| WO | WO 00/42072 | 7/2000 |
| WO | WO 00/44788 | 8/2000 |
| WO | WO 00/61739 | 10/2000 |
| WO | WO 00/67795 | 11/2000 |
| WO | WO 00/67796 | 11/2000 |
| WO | WO 00/74718 A1 | 12/2000 |
| WO | WO 00/76542 A1 | 12/2000 |
| WO | WO 01/03734 A1 | 1/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 A1 | 3/2001 |
| WO | WO 01/29246 A1 | 4/2001 |
| WO | WO 01/34194 A1 | 5/2001 |
| WO | WO 01/72333 A1 | 10/2001 |
| WO | WO 01/74388 A1 | 10/2001 |
| WO | WO 01/77342 A1 | 10/2001 |
| WO | WO 01/80884 A1 | 11/2001 |
| WO | WO 01/97858 A2 | 12/2001 |
| WO | WO 02/04021 A1 | 1/2002 |
| WO | WO 02/16329 | 2/2002 |
| WO | WO 02/24909 A2 | 3/2002 |
| WO | WO 02/34790 A1 | 5/2002 |
| WO | WO 02/38766 A2 | 5/2002 |
| WO | WO 02/056910 A1 | 7/2002 |
| WO | WO 02/060955 A2 | 8/2002 |
| WO | WO 02/079255 A1 | 10/2002 |
| WO | WO 02/092620 A2 | 11/2002 |
| WO | WO 02/096948 A2 | 12/2002 |
| WO | WO 02/102312 A2 | 12/2002 |
| WO | WO 03/002607 A1 | 1/2003 |
| WO | WO 03/024991 A2 | 3/2003 |
| WO | WO 03/053926 A1 | 3/2003 |
| WO | WO 03/049694 A2 | 6/2003 |
| WO | WO 03/061694 A1 | 7/2003 |
| WO | WO 03/068821 A2 | 8/2003 |
| WO | WO 03/085119 A1 | 10/2003 |
| WO | WO 2004/032828 A2 | 4/2004 |
| WO | WO 2004/035607 A2 | 4/2004 |
| WO | WO 2004/056312 A2 | 7/2004 |
| WO | WO 2004/058298 A1 | 7/2004 |
| WO | WO 2004/091657 A2 | 10/2004 |
| WO | WO 2004/103404 A1 | 12/2004 |
| WO | WO 2005/000351 A2 | 1/2005 |
| WO | WO 2005/000901 A2 | 1/2005 |
| WO | WO 2005/014618 A2 | 2/2005 |
| WO | WO 2005/016969 A2 | 2/2005 |
| WO | WO 2005/017529 A | 2/2005 |
| WO | WO 2005/044859 A2 | 5/2005 |
| WO | WO 2005/070963 A1 | 8/2005 |

OTHER PUBLICATIONS

Tincani et al., "The anti-β2-glycoprotein I activity in human anti-phospholipid syndrome sera is due to monoreactive low-affinity autoantibodies directed to epitopes located on native β2-glycoprotein I and preserved during species' evolution" *Journal of Immunology* 157(12):5732-5738 (Dec. 15, 1996).

Ahn et al., "Long-term remission from life-threatening hypercoaulable state associated with lupus anticoagulant (LA) following rituximab therapy" *Am. J. Hematol.* 78(2) :127-129 (2005).

Ahn et al., "Severe hypercoabulable state and concomitant life threatening bleeding successfully treated with rituximab" *Blood* (Abstract #4139) 102(11) :108b (Nov. 16, 2003).

Akashi et. al., "Successful Treatment of Refractory Systemic Lupus Erythematosus with Intravenous Immunoglobulins" *J. Rheumatology* 17:375-379 (1990).

Albert et al., "A Phase 1 trial of Rituximab (Anti-CD20) for treatment of Systemic Lupus Erythematous" *Arthritis Rheum.* (Abstract #LB9) 48(12) :3659 (Dec. 2003).

Anderson et al., "Expression of Human B Cell-Associated Antigens on Leukemias and Lymphomas: A Model of Human B Cell Differentiation" *Blood* 63(6) :1424-1433 (1984).

Anderson et al., "Revised estimate of the prevalence of multiple sclerosis in the United States" *Ann Neurol.* 31(3) :333-336 (Mar. 1992).

Andersson et al., "Multiple MAG peptides are recognized by circulating T and B lymphocytes in polyneuropathy and multiple sclerosis" *Eur J Neurol.* 9(3) :243-251 (May 2002).

Andrassy et al., "Wegener's granulomatosis with renal involvment: patient survival and correlations between initial renal function renal histology, therapy and renal outcome" *Clinical Nephrology* 35:139-147 (1991).

Anolik et al., "B cell depletion therapy in systemic lupus erythematosus" *Current Rhematology Reports* 5(5) :350-356 (Oct. 2003).

Anolik et al., "B lymphocyte depletion as a novel treatment for systemic lupus erythematosus (SLE): Phase I/II trial of rituximab (Rituxan (R)) in SLE" *Arthritis and Rheumatism* (Abstract # 2009) 44(9) ;S387 (Sep. 2001).

Anolik et al., "B lymphocyte Depletion in the treatment of Systemic Lupus (SLE): Phase I/II trial of Rituximab (RITUXAN) in SLE" *Arthritis and Rheumatism* (Abstract #717) 46(9) :S289 (Oct. 2002).

Anolik et al., "The relationship of FcgammaRIIIa genotype to degree of B cell depletion by rituximab in the treatment of systemic lupus erythematosus" *Arthritis and Rheumatism* 48 (2) :455-459 (Feb. 2003).

Arbuckle et al., "Development of autoantibodies before the clinical onset fo systemic lupus erythematosus" *New England J. of Medicine* 349(16):1526-1533 (Oct. 16, 2003).

Arzoo et al., "Treatment of refractory antibody mediated autoimmune disorders with an anti-CD20 monoclonal antibody (rituximab)" *Annals of the Rheumatic Diseases* 61(10):922-924.

Auner et al., "Restoration of erythropoiesis by rituximab in an adult patient with primary acruired pure red cell aplasia refractory to conventional treatment" *Br J Haematol.* 116(3):727-728 (Mar. 2002).

Baker et al., "Generation and characterization of LymphoStat-B, a human monoclonal antibody that antagonizes the bioactivities of B lymphocyte stimulator" *Arthritis and Rheumatism* 48(11) :3253-3256 (Nov. 2003).

Balow et al., "Vasculitic diseases of the kidney, polyarteritis, Wegener's granulomatosis, necrotizing and crescentic glomerulonephritis, and other disorders" *Diseases of the Kidney*, Schrier and Gottschalk, 5th edition, Boston:Little, Brown and Compan pp. 2095-2117 (1993).

Bauduer, "Rituximab: a very efficient therapy in cold agglutinins and refractory autoimmune haemolytic anaemia associated with CD20-positive, low-grade non-Hodgkin's lymphoma" *Br J Haematol.* 112(4):1085-1086 (Mar. 2001).

Berentsen et al., "Favourable response to therapy with the anti-CD20 monoclonal antibody rituximab in promary chronic cold agglutinin disease" *Br J Haemetol.* 115(1):79-83 (Oct. 2001).

Berentsen et al., "Rituximab for primary chronic cold agglutinin disease: a prosepctive study of 37 courses of therapy in 27 patients" *Blood* 103(8):2925-2928 (Apr. 15, 2004).

Berger, "Antimyelin antibodies as a predictor of clinically definite multiple sclerosis after a first demyelinating event" *N. Engl J Med.* 349(2):139-145 (Jul. 10, 2003).

Bielekova et al., "Encephalitogenic potential of the myelin basic protein peptide (amino acids 83-99) in multiple sclerosis: results of a phase II clinical trial with an altered peptide ligand" *Nat Med.* 6(10):1167-1175 (Oct. 2000).

Binstadt et al., "Rituximab therapy for multisystem autoimmune diseases in pediatric patients" *Journal of Pediatrics* 143:598-604 (Nov. 2003).

Boletis, "An open study of B cell depletion in patients with proliferative lupus nephritis: Preliminary results" *Journal of the American Society of Nephrology* (Abstracts issue SA-PO378) 14:379A (Nov. 2003).

Boomsma et al., "Prediction of relapses in Wegener's granulomatosis by measurement of antineutrophil cytoplasmic antibody levels" *Arthritis and Rheumatism* 43(9):2025-2033 (Sep. 2000).

Boomsma, M, "ANCA-associated vasculitis: occurrence, prediction, prevention, and outcome of relapses" *Thesis University Groningen* Chapter 1-11(ISBN 90-367-1451-6):1-166 (2001).

Booth et al., "Prospective Study of TNF Blockade with Infliximab in Anti-Neutrophil Cytoplasmic Antibody-Associated Systemic Vasculitis" *J. Am. Soc. Nephrol.* 15:717-721 (2004).

Bouroncle et al., "Treatment of Wegener's granulomatosis with Imuran" *Am. J. Med.* 42:314-318 (1967).

Calabrese, "Molecular differences in anticytokine therapies" *Clinical and Experimental Rheumatology* 21(2):241-248 (2003).

Cambridge et al., "B lymphocyte depletion in patients with rheumatoid arthritis: serial studies of immunological parameters" *Arthritis Rheum* 46(9):S1350 (2002).

Cambridge et al., "Serologic changes following B lymphocyte depletion therapy for rheumatoid arthritis" *Arthritis and Rheumatism* 48(8):2146-2154 (Aug. 2003).

Carter et al., "Humanization of an Anti-p185$^{HER2}$ Antibody For Human Cancer Therapy" *Proc. Natl. Acad. Sci. USA* 89(10):4285-4289 (May 1992).

Cepok et al., "Patterns of cerebrospinal fluid pathology correlate with disease progression in multiple sclerosis" *Brain* 124(Pt 11):2169-2176 (Nov. 2001).

Chambers and Isenberg, "Anti-B cell therapy (rituximab) in the treatment of autoimmune disease" *Lupus* 14(3):210-214 (2005).

Chira and Sandborg, "Novel therapies in pediatric rheumatic diseases" *Current Opinion in Pediatrics* 15(6):579-585 (2003).

Clark et al., "Role of Bp35 Cell Surface Polypeptide in Human B-cell Activation" *Proc. Natl. Acad. Sci. USA* 82:1766-1770 (Mar. 1985).

Cohen and Nagler, "Treatment of refractory autoimmune disease with ablative immunotherapy" *Autoimmunity Reviews* 3(2):21-29 (Feb. 2004).

Cohen and Nagler, "Treatment of refractory autoimmune diseases with lymphoablation and hematopoietic stem cell support" *Israel Medical Association Journal* 4(11 Suppl.):865-867 (Nov. 1, 2002).

Cohen et al., "Treatment of refractory autoimmune diseases with ablative immunotherapy using monoclonal antibodies and/or high dose chemotherapy with hematopoietic stem cell support" *Current Pharmaceutical Design* 9(3):279-288 (2003).

Cohen Teravert et al., "Association Between Active Wegerner's Granulomatosis and Anticytoplasmic Antibodies" *Arch. Intern. Med.* 149:2461-2465 (Nov 1989).

Cohen Tervaert et al., "Detection of Autoantibodies Against Myeloid Lysosomal Enzymes: A Useful Adjunct to Classification of Patients with Biopsy-Proven Necrotizing Arteritis" *Am. J. Med.* 91:59-66 (Jul. 1991).

Cohen Tervaert et al., "Prevention of relapses in Wegener's granulomatosis by treatment based on antineutrophil cytoplasmic antibody titre" *Lancet* 336:709-711 (1990).

CohenTervaert et al., "Serial ANCA testing is useful in monitoring disease activity of patients with ANCA-associated vasculitides" *Sarcoidosis Vasc. Diffuse Lung Dis.* 13:241-245 (1996).

Coll et al., "Rituximab therapy for the type B syndrome of severe insulin resistance" *N Engl J Med.* 350(3):310-311 (Jan. 15, 2004).

Confavreux et al., "Relapses and progression of disability in multiple sclerosis" *N Engl J Med.* 343(20):1430-1438 (Nov. 16, 2000).

Cooper et al., "The efficacy and safety of B-cell depletion with anti-CD20 monoclonal antibody in adults with chronic immune thrombocytopenic purpura" *Br. J. Haematol.* 125:232-239 (2004).

Cragg et al., "Complement-mediated-lysis by anti-CD20 mAb correlates with segration into lipid rafts" *Blood* 101(3):1045-1052 (Feb. 1, 2003).

Cragg et al., "The biology of CD20 and its potential as a target for mAb therapy" *Curr. dir. Autoimmun.* 8:140-174 (2005).

Cross et al., "Preliminary Results from a Phase II trial of-Rituximab in MS" (Abstract), 8th Ann. Meeting of the Americas Committee, for Research and Treatment in Multiple Sclerosis pp. 20-21 (Oct 19, 2003).

Crowley and Walters, "Determination of immunoglobulins in blood serum by high-performance affinity chromatography" *J. Chromatogr.* 266:157-162 (1983).

Cupps et al., "Suppression of Human B Lymphocyte Function by Cyclophosphamide" *J. Immunol.* 128(6):2453-2457 (Jun. 1982).

D'Arena et al., "Late and long-lasting response in an adult chronic idiopathic thrombocytopenic after extended course of rituximab" *Leuk Lymphoma.* 44(3):561-562 (Mar. 2003).

D'Cruz and Hughes, "The treatment of lupus nephritis" *BMJ* 330(7488):377-378 (Feb. 2005).

de Groot et al., "Therapy for the maintenance of remission in sixty-five patients with generalized Wegener's granulomatosis" *Arthritis and Rheumatism* 39(12):2052-2061 (Dec. 1996).

De Vita et al., "Efficacy and Safety of Rituximab Treatment in Type II Mixed Cryoglobulinemia" *Arthritis & Rheum.* (ACR Concurrent Session Vaculitis: Novel Treatment and Pathogenesis Abstract #469) 46:S206 (Oct. 26, 2002).

De Vita et al., "Efficacy of Selective B Cell Blockade in the Treatment of Rheumatoid Arthritis" *Arthritis and Rheumatism* 46(8):2029-2033 (Aug. 2002).

De'Oliviera et al., "Relationship Between Disease Activity and Antineutrophil Cytoplasmic Antibody Concentration in Long-Term Management of Systemic Vasculitis" *Am J. Kidney Dis.* 25(3):380-389 (Mar. 1995).

Demidem et al., "Chimeric Anti-CD20 (IDEC-C2B8) Monoclonal Antibody Sensitizes a B Cell Lymphoma Cell Line to Cell Killing by Cytotoxic Drugs" *Cancer Biotherapy & Radiopharmaceuticals* 12(3):177-186 (1997).

Doran et al., "Frequency of infection in patients with rheumatoid arthritis compared with controls: a population-based study" *Arthritis Rheum.* 46(9):2287-2293 (Sep. 2002).

Dumont, "IDEC-131 IDEC/Eisai" *Current Opinion in Investigational Drugs* 3(5):725-734 (May 1, 2002).

Duna et al., "Wegener's granulomatosis" *Rheum Dis Clin North Am.* 21(4):949-986 (Nov. 1995).

Dupuy et al., "Treatment of refractory pemphigus vulgaris with rituximab (anti-CD20 monoclonal antibody)" *Arch Dermatol.* 140(1):91-96 (Jan. 2004).

Edelbauer et al., "Rituximab in childhood systemic lups erythematosus refractory to conventional immunosuppression Case report" *Pediatric Nephrology* 20(6):811-813 (2005).

Edwards and Cambridge, "Sustained Improvement in Rheumatoid Arthritis Following a Protocol Designed to Deplete B Lymphocytes" *Rheumatology* 40:205-211 (2001).

Edwards et al., "B-lymphocyte depletion therapy in rheumatoid arthritis and other autoimmune disorders" *Biochemical Society Transactions* 30 (part 4):824-828 (2002).

Edwards et al., "Efficacy and safety of Rituximab, a B-cell targeted chimeric monoclonal antibody: A randomized, placebo-controlled trial in patients with rheumatoid arthritis" *Arthritis and Rheumatism* (Abstract #446) 46(9):S197 (2002).

Edwards et al., "Efficacy of B-cell-targeted therapy with rituximab in patients with rheumatoid arthritis" *New England J. of Medicine* 350(25) :2572-2581 (Jun. 17, 2004).

Egg et al., "Anti-MOG and anti-MBP antibody subclasses in multiple sclerosis" *Mult Scler.* 7(5) :285-289 (Oct. 2001).

Einfeld et al., "Molecular Cloning of the Human B Cell CD20 Receptor Predicts a Hydrophobic Protein with Multiple Transmembrane Domains" *EMBO Journal* 7(3) :711-717 (1988).

Eisenberg et al. "A Phase I trial of B-cell depletion with anti-CD20 monoclonal antibody (rituximab) in the treatment of systemic lupus erythematosus" *Arthritis Research and Therapy* (Abstract #29) 5(Suppl 3) :S9-S10 (2003).

Eisenberg R., "SLE—Rituximab in lupus" *Arthritis Res Ther.* 5(4) : 157-159 (2003).

Eisenberg, "Mechanisms of autoimmunity" *Immunol. Res.* 27(2-3) : 203-217 (2003).

Emery et al., "Efficacy and Safety of Rituximab at 2 Years Following a Single Treatment in Patients with Active Rheumatoid Arthritis" *Arthritis and Rheumatism* (Abstract #1762) S0(S9) :S659 (2004).

Emery et al., "Sustained Efficacy at 48 Weeks after Single treatment Course of Rituximab in patients with Rheumatoid Arthritis" *Arthritis Rheumatology* (Abstract #1095) 48(9) :S439 (2003).

Eriksson P., "Nine patients with anti-neutrophil cytoplasmic antibody-positive vasculitis successfully treated with rituximab" *J Intern Med.* 257(6) :540-548 (Jun 2005).

Eriksson, "Short-term outcome and safety in 5 patients with ANCA-positive vasculitis treadted with rituximab" *Kidney and Blood Pressure Research* (Abstract P87) 26:294 (2003).

Esiri M., "Multiple sclerosis: a quantitative and qualitative study of immunoglobulin-containing cells in the central nervous system" *Neuropathol Appl Neurobiol* 6(1) :9-21 (Jan. 1980).

Falk et al., "Anti-Neutrophil Cytoplasmic Autoantibodies with Specificity for Myeloperoxidase in Patients with Systemic Vasculitis and Idiopathic Necrotizing and Crescentic Glomerulonephritis" *New England J. of Medicine* 318(25) :1651-1657 (Jun 23, 1988).

Falk et al., "Clinical Course of Anti-Neutrophil Cytoplasmic Autoantibody-associated Glomerulonephrities and Systemic Vasculitis" *Annals of Internal Medicine* 113(9) :656-663 (Nov. 1, 1990).

Fauci et al., "The spectrum of vasculitis: clinical, pathologic, immunologic and therapeutic considerations" *Annals of Internal Medicine* 89(5 Pt 1) :660-676 (Nov. 1978).

Fauci et al., "Wegener's Granulomatosis: Prospective Clinical and Therapeutic Experience With 85 Patients for 21 Years" *Annals of Internal Medicine* 98(1) :76-85 (Jan. 1983).

Filippini et al., "Interferons in relapsing remitting multiple sclerosis: a systematic review" *Lancet* 361 (19357) :545-552 (Feb. 15, 2003).

Foster et al., "Cytokine-receptor pairing: Accelerating discovery of cytokine function" *Nature Reviews. Drug Discovery* 3(2) :160-170 (Feb. 2004).

Fra et al., "Reimission of refractory lupus nephritis with a protocol including rituximab" *Lupus* 12(10) :783-787 (2003).

Gaskin et al., "Systemic vasculitis" *Oxford textbook of clinical nephrology*, Cameon et al., Oxford University Press vol. 1(4.5.3) :612-636 (1992).

Genain et al., "Identification of autoantibodies associated wtih myelin damage in multiple sclerosis" *Nat Med.* 5(2) :170-175 (Feb. 1999).

Gescuk, et al., "Novel Therapeutic Agents for Systemic Lupus Erythematosus" *Current Opinion in Rheumatology* 14:515-521 (2002).

Glennie and van de Winkel, "Renaissance of cancer therapeutic antibodies" *Drug Discov Today* 8(11):503-510 (Jun. 1, 2003).

Gong et al., "Importance of cellular microenvironment and circulatory dynamics in B cell immunotherapy" *J. Immunol.* 174:817-826 (2005).

Gordon et al., "Relapses in patients with a systemic vasculitis" *Q J. Med* 86(12) :779-789 (Dec. 1993).

Gordon et al., "Zevalin™ radioimmunotherapy is associated with a low incidence of human-anti mouse antibody (HAMA) and human anti-Rituxan$^R$ antibody (HACA) response". *Blood* (Abstract #4632) 98(11 Part 2) :228b (2001).

Gorman et al., "B cell depletion in autoimmune disease" *Arthritis Research and Therapy* 5(Supplement 4) :S17-S21 (2003).

Gorman et al., "Does B cell depletion have a role to play in the treatment of systemic lupus erythematosus?" *Lupus* 13(5) :312-316 (2004).

Goronzy and Weyand, "B cells as a therapeutic target in autoimmune disease" *Arthritis Research and Therapy* 5(3) :131-135 (Mar. 19, 2003).

Gottenberg et al., "Tolerance and short term efficacy of rituximab in 43 patients with systemic autoimmune diseases" *Annals of the Rheumatic Diseases* 64(6) :913-920 (2005).

Guillevin et al., "Antineutrophil cytoplasmic antibodies, abnormal angiograms and pathological findings in polyarteritis nodosa and Churg-Strauss Syndrome: Indications for the classification of vasculitides of the polyarteritis nodose group" *Br. J. Rheumatology* 35(10) :958-964 (1996).

Guillevin et al., "Churg-Strauss Syndrome: Clinical Study and Long-Term Follow-Up of 96 Patients" *Medicine* 78(1) :26-37 (Jan. 1999).

Guillevin et al., "Microscopic Polyangiitis" *Arthritis and Rheumatism* 42(3) :421-430 (Mar. 1999).

Hainsworth, "Rituximab as first-line and maintenance therapy for patients with indolent non-hodgkin's lymphoma" *J Clin Oncol.* 20(20) :4261-4267 (Oct. 15, 2002).

Hainsworth, "Single-agent rituximab as first-line and maintenance treatment for patients with chronic lymphocytic leukemia or small lymphocytic lymphoma: a phase II trial of the Minnie Pearl Cancer Research Network" *J Clin Oncol.* 21(9) :1746-1751 (May 1, 2003).

Hamaguchi et al., "The peritoneal cavity provides a protective niche for B1 and conventional B lymphocytes during anti-CD20 immunotherapy in mice" *J. Immunol.* 174:4389-4399 (2005).

Hasak Janet, "Statement of Janet E. Hasak for" pp. 1-2 (Oct., 8, 2004).

Haubitz et al., "Cyclosporin for the prevention of disease reactivation in relapsing ANCA-associated vasculitis" *Nephrol. Dial. Transplant* 13:2074-2076 (1998).

Hellmich and Gross, "The annual European Congress of Rheumatology: Recent advances in the treartment of rheumatic diseases" *Expert Opinion on Investigational Drug* 12(10) :1713-1719 (2003).

Hoffman et al., "Wegener Granulomatosis: An Analysis of 158 Patients" *Annals of Internal Medicine* 116:488-498 (Mar. 15, 1992).

Hong e tal., "Simple quantitative live cell and anti-idiotypic antibody based ELISA for humanized antibody directed to cell surface protein CD20" *Journal of Immunological Methods* 294:189-197 (2004).

Houssiau, "Management of refractory systemic rheumatic diseases" *Acta Clinica Belgica* 58(5) :314-317 (2003).

Idusogie et al., "Engineered antibodies with increased activity to recruit complement" *J. Immunol.* 166(4) :2571-2575 (2001).

Isenberg and Leckie, "Biological treatments for systemic lupus erythematosus" *Scandinavian Journal of Rheumatology* 31(4) :187-191 (2002).

Izquierdo, "Intrathecal IgG synthesis: marker of progression in multiple sclerosis patients" *Acta Neurol Scand.* 105(3) :158-163 (Mar. 2002).

Izzedine et al., "Lymphopenia in Wegener s Granulomatosis" *Nephron* 92:466-471 (2002).

Jayne and Rasmussen, "Treatment of Antineutrophil Cytoplasm Autoantibody-Associated Systemic Vasculitis: Initiatives of the European Community Systemic Vasculitis Clinical Trials Study Group" *Mayo Clin. Proc.* 72:737-747 (Aug. 1997).

Jayne et al., "A randomized trial of maintenance therapy for vasculitis associated with antineutrophil cytoplasmic autoantibodies" *New England J. of Medicine* 349:36-44 (Jul. 3, 2003).

Jayne et al., "ANCA and predicting relapse in systemic vasculitis" *QJM* 88(2) :127-133 (Feb. 1995).

Jayne et al., "B-cell depletion with rituximab for refractory vasculitis" *Kidney and Blood Pressure Research* (Abstract P88) 26:294-295 (2003).

Jayne, "Current attitudes to the therapy of vasculitis" *Kidney and Blood Pressure Research* 26(4) :231-239 (2003).

Jayne, "Evidence-based treatment of systemic vasculitis" *Rheumatology* 39:585-595 (2000).

Jennette and Falk, "Small-vessel vasculitis" *New England J. of Medicine* 337:1512-1523 (Nov. 20, 1997).

Jennette et al., "Nomenclature of Systemic Vasculitides" *Arthritis and Rheumatism* 37(2) :187-192 (Feb. 1994).
Jilani Iman et al., "Transient down-modulation of CD20 by rituximab in patients with chronic lymphocytic leukemia" *Blood* 102(10) :3514-3520 (Nov. 15, 2003).
Jinno Yoshio et al., "Local Expansion of Plasma-Lineage Cells Without Formation of Germinal Centers Characterizes Ulcerative Colitis" *Digestive Disease Week Abstract and Itinerary* (Abstract #M1164) (2003).
Jordan, "Intravenous Gamma-Globulin Therapy in systemic Lupus Erythematosus and Immune Complex Disease" *Clin. Immunol. Immunopathol.* 53:S164-S169 (1989).
Kalled et al., "BAFF: B cell survival factor and emerging therapeutic target for autoimmune disorders" *Expert Opinion on Therapeutic Targets* 7(1) :115-123 (2003).
Kamesh et al., "ANCA-Positive Vasculitis" *J. Am. Soc. Nephrol.* 13:1953-1960 (2002).
Kaminski, M. et al., "Development of HAMA after Bexxar™ therapy does not preclude treatment with rituximab" *Blood* (Abstract #3172) 96(11 Part 1) :734a (2000).
Kazkaz and Isenberg, "Anti B cell Therapy (rituximab) in the treatment of auroimmune diseases" *Current Opinion in Pharmacology* 4:398-402 (2004).
Keogh et al., "Induction of remission by B lymphocyte depletion in eleven patients with refractory antineutrophil cytoplasmic antibody-associated vasculitis" *Arthritis Rheum.* 52(1) :262-268 (Jan. 2005).
Keogh et al., "Rituximab—A Potential Mechanistic-Based Therapy for Treatment of Refractory ANCA-Associated Vasculitis" *Kidney Blood Pressure Research* (Abstract #O32) 26:293 (2003).
Keogh et al., "Rituximab for Refratory Wegener's Granulomatosis: Report of A Prospective, Open-Label Pilot Trial" *AJRCCM Articles in Press* pp. keogh-0-33 (Oct 13, 2005).
Keogh et al., "Rituximab for Remission Induction in Severe ANCA-Associated Vasculities. A Report of a Prospective Open-Label Pilot in 10 Patients" *American College of Rheumatology, Session title: Vasculitis* (Abstract 605) (Oct. 18, 2004).
Klemmer et al., "Treatment of antibody mediated autoimmune disorders with a Anti-CD20 monoclonal antibody Rituximab" *Arthritis and Rheumatism* (Abstract #1623) 48(Suppl 9) :S624 (2003).
Kneitz et al., "Effective B cell depletion with rituximab in the treatment of autoimmune diseases" *Immunobiology* 206:519-527 (2002).
Koper, N. et al., "Quantitation of IgG and IgM human anti-mouse antibodies (HAMA) interference in CA 125 measurements using affinity chromatography" *Clin. Chem. Lab. Med* 36(1) :23-28 (1998).
Kremenchutzky et al., "The natural history of multiple sclerosis: a geographically based study. 7. Progressive-relapsing and relapsing-progressive multiple sclerosis: a re-evaluation" *Brain* 122 (Pt 10) :1941-1949 (Oct. 1999).
Kurtzke, "Rating neurologic impairment in multiple sclerosis: an expanded disability status scale (EDSS)" *Neurology* 33(11) :1444-1452 (Nov. 1983).
Lake and Dionne, "Future Strategies in Immunotherapy" *Burger's Medicinal Chemistry and Drug Discovery*, Abraham, 6th edition, Hoboken:John Wiley & Sons, Inc., Chapter 6, vol. 5:223-247 (2003).
Langford, "Treatment of ANCA-Associated Vasculitis" *New England J. of Medicine* 349:3-4 (Jul. 3, 2003).
Layios et al., "Remission of severe cold agglutinin disease after Rituximab therapy" *Leukemia* 15(1) :187-188 (Jan. 2001).
'Leandro et al., "An open study of B lymphocyte depletion in systemic lupus erythematosus" *Arthritis and Rheumatism* 46(10) :2673-2677 (Oct 2002).
Leandro et al., "B cell repopulation occurs mainly from naive B cells in patients with rheumatoid arthritis and systemic lupus erythematosus treated with rituximab" *Arthritis and Rheumatism* (Abstract #1160) 48(Suppl 9) :S464 (Oct. 27, 2003).
Leandro et al., "B Lymphocyte depletion in rheumatoid arthritis: early evidence for safety, efficacy and dose response" *Arthritis and Rheumatism* (#1905) 44(9) :S370 (2001).
Leandro et al., "Clinical outcome in 22 patients with rheumatoid arthritis treated with B lymphocyte depletion" *Annals of the Rheumatic Diseases* 61(10) :883-888 (2002).

Leandro et al., "Treatment of refractory lupus nephritis with B lymphocyte depletion" *Arthritis and Rheumatism* (Abstract #924) 48 (Supplement 9) :S378 (2003).
Lee and Kueck, "Rituxan in the Treatment of Cold Agglutinin Disease" *Blood* 92:3490-3491 (1998).
The Lenercept Multiple Sclerosis Study Group and The University of British Columbia MS/MRI, "TNF neutralization in MS: results of a randomized, placebo-controlled multicenter study" *Neurology* 53(3) :457-465 (Aug. 11, 1999).
Leon et al., "Interference by rheumatoid factor activity in the detection of antiavian antibodies in pigeon breeders disease" *Clin. Exp. Med.* (Abstract) 2(2) :59-67 (Jul. 2002).
Levine and Pestronk, "IgM antibody-related polyneuropathies: B-cell depletion chemotherapy using Rituximab" *Neurology* 52(8) : 1701-1704 (May 12, 1999).
Levine, "A Pilot Study of Rituximab Therapy for Refractory Dermatomyositis" *Arthritis Rheum.* (Abstract #1299) 46 (Suppl. 9) :S488-S489 (2002).
Lhote and Guillevin, "Polyarteritis nodosa, microscopic polyangiitis, and Churg-Strauss syndrome. Clinical aspects and treatment" *Rheumatic Disease Clinics of North America* 21(4) :911-947 (Nov. 1995).
Liang and Tedder, "CD20" *CD20 Wiley Encyclopedia of Molecular Medicine* pp. 562-564 (Jan. 15, 2002).
Linnik et al., "Workshop report on some new ideas about the treatment of systemic lupus erythematosus" *Lupus* 11(12) :793-796 (2002).
Lockshin and Sammaritano, "Lupus pregnancy" *Autoimmunity* 36 (1) :33-40 (2003).
Looney et al., "B-cell depletion as a novel treatment for systemic lupus erythematosus: a phase I/II dose-escalating trial of rituximab" *Arthritis and Rheumatism* 50(8) :2580-2589 (Aug. 2004).
Looney et al., "Treatment of SLE with anti-CD20 monoclonal antibody" *Curr. Dir. Autoimmun.* 8:193-205 (2005).
Looney, "B cell-targeted therapy in diseases other than rheumatoid arthritis" *J. Rheumatology* 32(Suppl. 73) :25-28 (2005).
Looney, "B cells as a therapeutic target in autoimmune diseases other than rheumatoid arthritis" *Rheumatology* 44(Suppl. 2) :ii13-ii17 (2005).
Looney, "Treating human autoimmune disease by depleting B cells" *Annals of the Rheumatic Diseases* 61:863-866 (2002).
Lucchinetti et al., "Heterogeneity of multiple sclerosis lesions: implications for the pathogenesis of demyelination" *Ann Neurol.* 47(6) :707-717 (Jun. 2000).
MacDermott et al., "Alterations of IgM, IgG, and IgA synthesis and secretion by peripheral blood and intestinal mononuclear cells from patients with ulcerative colitis and Crohn's disease" *Gastroenterology* 84:844-852 (Nov. 1981).
Maeda, T. et al., "Successful treatment with a chimeric anti-CD20 monoclonal antibody (IDEC-C2B8, Rituximab) for a patient with relapsed mantle cell lymphoma who developed a human anti-chimeric antibody" *Intl. J. Hematology* 74(1):70-75 (2001).
Maloney et al., "The Anti-Tumor Effect of Monoclonal Anti-CD20 Antibody (mAb) Therapy Includes Direct Anti-Proliferative Activity and Induction of Apoptosis in CD20 Positive Non-Hodgkin's Lymphoma (NHL) Cell Lines" *Blood* (Abstract #2535) 88(10) :637a (1996).
Manches et al., "In vitro mechanisms of action of rituximab on primary non-Hodgkin lymphomas" *Blood* 101(3) :949-954 (Feb. 1, 2003).
Martin and Chan, "Pathogenic roles of B cells in human autoimmunity; insights from the clinic" *Immunity* 20(5) :517-527 (may 2004).
Mata et al., "Multiple sclerosis is associated with enhanced B cell responses to the ganglioside GD1a" *Mult Scler.* 5(6) :379-388 (Dec. 1999).
Matthews, R., "Medical Heretics" *New Scientist* 170(2285):34-37 (Apr. 7, 2001).
McDonald et al., "Recommended diagnostic criteria for multiple sclerosis: guidelines from the International Panel on the diagnosis of multiple sclerosis" *Ann Neurol.* 50(1) :121-127 (Jul. 2001).
McKeever et al., "A Toxicity Evaluation of Humanized-Anti-CD20 Antibody PRO70769" *Society of Toxicology Annual Meeting, Baltimore, Maryland* (Poster #75) 78(S-1):15 (Mar. 22, 2004).

Mehta et al., "Exacerbation of lupus while receiving rituximab for chronic refractory thrombocytopenia" *Blood* (Abstract #3862) 98(11) :61b-62b (Nov. 16, 2001).

Mintzer David Michael, "Combined Autoimmune Thrombocytopenia Blood Neutropenia: Treatment with Rituximab" *Blood* (Abstract #3635) 100(11) (Nov. 16, 2002).

Mire-Sluis, A. et al., "Recommendations for the design and optimization of immunoassays used in the detection of host antibodies against biotechnology products" *J. Immunol. Methods* 289:1-16 (2004).

Nachman et al., "Treatment Response and Relapse in Antineutrophil Cytoplasmic Autoantibody-Associated Microscopic Polyangiitis and Glomerulonephritis1 2" *J. Am. Soc. Nephrol.* 7:33-39 (1996).

Neuwelt, "The role of plasmapheresis in the treatment of severe central nervous system neuropsychiatric systemic lupus erythematosus" *Therapeutic Apheresis and Dialysis* 7(2) :173-182 (Apr. 2003).

Niles et al., "The Syndrome of Lung Hemorrhage and Nephritis Is Usually an ANCA-Associated Condition" *Arch. Intern. Med.* 156:440-445 (Feb. 1996).

Nobile-Orazio, "IgM paraproteinaemic neuropathies" *Curr. Opin. Neurol.* 17(5) :599-605 (Oct. 17, 2004).

Noonan et al., "Prevalence estimates for MS in the United States and evidence of an increasing trend for woman" *Neurology* 58(1) :136-138 (Jan. 8, 2002).

Norton et al., "Combined corticosteroid and azathioprine therapy in 2 patients with Wegner's granulomatosis" *Archives of Internal Medicine* 121(6) :554-560 (Jun. 1968).

Nowack et al., "Mycophenolate Mofetil for Maintenance Therapy of Wegner s Granulomatosis and Microscopic Polyangiitis: A Pilot Study in 11 Patients with Renal Involvement" *J. Am. Soc. Nephrol.* 10:1965-1971 (1999).

O'Connor, "Key issues in the diagnosis and treatment of multiple sclerosis. An overview" *Neurology* 59(6 Supp 3) :S1-S33 (Sep. 24, 2002).

Oelke, "American College of Rheumatology—65th Annual Meeting" *IDrugs* 5(1) :30-31 (2002).

Onuma et al., "Autoimmunity in ulcerative colitis (UC): a predominant colonic mucosal B cell response against human tropomyosin isoform 5" *Clin Exp. Immunol.* 121:466-471 (2000).

Park and Smolen, "Monoclonal antibody therapy" *Advances in Protein Chemistry* 56:369-421 (2001).

Patel et al., "Graft-versus-Kaposi's Sarcoma effect and reversal of Lupus Anticoagulant Syndrome and Thalassemia Intermedia after non-myeloablative allogeneic stem cell transplant" *Blood* (Abstract 5256) 98(11) :370b (Nov. 16, 2001).

Pavelka et al., "Improvement in patient-reported outcomes with rituximab in patients with rheumatoid arthritis" *Annals of the Rheumatic Diseases* (Abstract FRI0135) 63(S1) :289-290 (2004).

Penichet and Morrison, "Antibody Engineering" *Wiley Encyclopedia of Molecular Medicine* (Section: Chimeris, Humanized and Human Antibodies) pp. 214-216 (2002).

Perrotta and Abuel, "Response of Chronic Relapsing ITP of 10 Years Duration to Rituximab" *Blood* (Abstract #3360) 92(10 Suppl. 1 Part 1-2) :88b (1998).

Perrotta et al., "Rituxan in the treatment of chronic idiopathic thrombocytopenia purpura (ITP)" *Blood* (Abstract #49) 94:14a (1999).

Perrotta, "Anti-CD20 monoclonal antibody (rituximab) for life-threatening autoimmune haemolytic anaemia in a patient with systemic lupus erythematosus" *British Journal of Haematology* 116(2) : 465-467 (Feb. 2002).

Pestronk et al., "Treatment of IgM antibody associated polyneuropathies using rituximab" *J. Neurol Neurosurg Psychiatry* 74(4) :485-489 (Apr. 2003).

Pettersson et al., "Incidence and outcome of pauci-immune necrotizing and crescentic glomerulonephritis in adults" *Clinical Nephrology* 43(3) :141-149 (1995).

Podolsky, D., "Inflammatory Bowel Disease" *New England J. of Medicine* 347(6) :417-429 (Aug. 8, 2002).

Popa et al., "Differential B- and T-cell activation in Wegener's granulomatosis" *J. Allergy Clin. Immunol.* 103 :885-894 (May 1999).

Pranzatelli et al., "CSF B-Cell Over-Expansion in Paraneoplastic Opsoclonus-Myoclonus: Effect of Rituximab, an Anti-B-Cell Monoclonal Antibody" *Neurology* (Abstract #P05.128) 60(5(suppl 1)) :A395 (Mar. 2003).

Press et al., "Monoclonal Antibody 1F5 (Anti-CD20) Serotherapy of Human B Cell Lymphomas" *Blood* 69(2) :584-591 (Feb. 1987).

Prineas and Wright, "Macrophages, lymphocytes, and plasma cells in the perivascular compartment in chronic multiple sclerosis" *Laboratory Investigation* 38(4) :409-421 (Apr. 1978).

Protheroe et al., "Remission of Inflammatory Arthropathy in Association with Anti-CD20 Therapy for Non-Hodgkin's Lymphoma" *Rheumatology* 38(11) :1150-1152 (Nov. 1999).

Quartier et al., "Treatment of childhood autoimmune haemolytic anaemia with rituximab" *Lancet* 358:1511-1513 (Nov. 3, 2001).

Radis et al., "Effects of cyclophosphamide on the development of malignancy and on long-term survival of patients with rheumatoid arthritis" *Arthritis and Rheumatism* 38 (8) :1120-1127 (Aug. 1995).

Rahman, "Cytokines in systemic lupus erythematosus, London, UK" *Arthritis Research and Therapy* 5 (4) :160-164 (2003).

Raj et al., "Successful Treatment of Refractory Autoimmune Hemolytic Anemia With Monthly Rituximab Following Nonmyeloablative Stem Cell Transplantation for Sickle Cell Disease" *J. Pediatr. Hematol. Oncol.* 26(5):312-314 (May 2004).

Rastetter et al., "Rituximab: expanding role in therapy for lymphomas and autoimmune diseases" *Annual Review of Medicine* 55:477-503 (2004).

Ratanatharathorn et al., "Anti-CD20 chimeric monoclonal antibody treatment of refractory immune-mediated thrombocytopenia in a patient with chronic graft-versus-host disease" *Ann Intern Med.* 133(4) :275-279 (Aug. 15, 2000).

Reff et al., "Depletion of B Cells In Vivo by a Chimeric Mouse Human Monoclonal Antibody to CD20" *Blood* 83(2) :435-445 (1994).

Reindl et al., "Antibodies against the myelin oligodendrocyte glycoprotein and the myelin basic protein in multiple sclerosis and other neurological diseases: a comparative study" *Brain* 122 (Pt 11) : 2047-2056 (Nov. 1999).

Reinhold-Keller et al., "An interdisciplinary approach to the care of patients with Wegener's granulomatosis: long-term outcome in 155 patients" *Arthritis and Rheumatism* 43(5) :1021-1032 (May 2000).

Renaud et al., "Rituximab in the treatment of polyneuropathy associated with anti-MAG antibodies" *Muscle Nerve* 27(5) :611-615 (May 2003).

Robak, "Monoclonal antibodies in the treatment of autoimmune cytopenias" *European Journal of Haematology* 72:79-88 (2004).

Rojas-Garcia et al., "Chronic neuropathy with IgM anti-ganglioside antibodies: Lack of long term response to rituximab" *Neurology* 61(2 of 2) :1814-1816 (Dec. 2003).

Rudick et al., "Multiple sclerosis progression in a natural history study: predictive value of cerebrospinal fluid free kappa light chains" *Mult Scler.* 1(3) :150-155 (Nov. 1995).

Russell et al., "Detection of Anti-Neutrophil Cytoplasmic Antibodies under Actual Clinical Testing Conditions" *Clinical Immunology* 103(2) :196-203 (2002).

Sadatipour, "Increased circulating antiganglioside antibodies in primary and secondary progressive multiple sclerosis" *Ann Neurol.* 44(6) :980-983 (Dec. 1998).

Saigal et al., "Hypocomplementemic urticarial vasculitis with angioedema, a rare presentation of systemic lupus erythematosus: rapid response to rituximab" *Journal of the American Academy of Dermatology* 49(Supplement 5 ) :S283-S285 (Nov. 2003).

Saito et al., "Successful treatment with anti-CD20 monoclonal antibody (rituximab) of life-threatening refractory systemic lupus erythematosus with renal and central nervous system involvement" *Lupus* 12:798-800 (2003).

Saleh et al., "A pilot study of the anti-CD20 monoclonal antibody rituximab in patients with refratctory immune thrombocytopenia" *Semin Oncol.* 27(6 Supp 12) :99-103 (Dec 2000).

Sanders et al., "Maintenance Therapy for Vasculitis Associated with Antineutrophil Cytoplasmic Autoantibodies" *New England J. of Medicine* 349(21) :2072-2073 (Nov. 20, 2003).

Sarwal et al., "Molecular Heterogeneity in Acute Renal Allograft Rejection Identified by DNA Microarray Profiling" *New England J. of Medicine* 349(2) :125-138 (Jul. 10, 2003).

Savage et al., "Primary systemic vasculitis" *Lancet* 349:553-558 (Feb. 22, 1997).

Sfikakis et al., "Remission of Proliferative Lupus Nephritis Following B Cell Depletion Therapy Is Preceded by Down-Regulation of the T Cell Costimulatory Molecule CD40 Ligand" *Arthritis and Rheumatism* 52(2) :501-513 (Feb. 2005).

Sfikakis PP et al., "Clinical Responses Correlate with Deactivation of T Cells Following Therapeutic B Cell Depletion in Patients With Lupus Nephritis" *Cutting edge in rheumatology 3* (EULAR Berlin, 1 page) (Jun. 11, 2004).

Shan, D. et al., "Signaling events involved in anti-CD20-induced apoptosis of malignant human B cells" *Cancer Immunol. Immunother.* 48(12) :673-683 (2000).

Shanahan et al., "Upcoming biologic agents for the treatment rheumatic diseases" *Current Opinion in Rheumatology* 15(3) :226-236 (May 2003).

Shaw et al., "B cell therapy for rheumatoid arthritis: the rituximab (anti-CD20) experience" *Ann Rheum Dis.* 62(Suppl. 2) :ii55-ii59 (Nov. 2003).

Siden A., "Isoelectric focusing and crossed immunoelectrofocusing of CSF immunoglobulins in MS" *J. Neurol.* 221(1) :39-51 (Jul. 11, 1979).

Silverman and Weisman, "Rituximab therapy and autoimmune disorders: prospects for anti-B cell therapy" *Arthritis and Rheumatism* 48(6) :1484-1492 (Jun. 2003).

Silverman, "Anti-CD20 therapy in systemic lupus erythematosus: a step closer to the clinic" *Arthritis and Rheumatism* 52(2) :371-377 (Feb. 2005).

Smith and Jayne, "A Prospective, Open Label Trial of B-cell Depletion with Rituximab in Refractory Systemic Vasculitis" *Journal of the American Society of Nephrology* (11th International Vasculitis and ANCA workshop) 14(Poster # SU-P0998) :755A (2003).

Solsky and Wallace, "New therapies in systemic lupus erythematosus" *Best Practice and Research Clinical Rheumatology* 16(2) :293-312 (2002).

Somer et al., "Improvement in Sjogren's syndrome following therapy with rituximab for margianl zone lymphoma" *Arthritis and Rheumatism* 49(3) :394-398 (Jun. 15, 2003).

Song and McCutcheon, "Strategies, Challenges and Design of Neutralizing Antibody Assays for Biotherapeutics: Development of a Cell-based Rituximab-RA NAb Assay" (Slides presnted at Immunogenicity for Biotherapeutics Conference, San Francisco, CA, USA,) pp. 1-23 (May 23-25, 2005).

Song, A., "Strategies, Challenges and Design of Neutralizing Antibody Assays for Biotherapeutics: Development of a Cell-based Rituximab-RA NAb Assay" (Abstract with Slides presented at Biological Assay Development & Validation Conference, Reston, VA, USA,) pp. 1-19 (Apr. 25-27, 2005).

Specks et al., "Response of Wegener's Granulomatosis to anti-CD20 Chimeric Monoclonal Antibody Therapy" *Arthritis and Rheumatism* 44(12) :2836-2840 (Dec. 2001).

Stahl et al., "Rituximab in RA: Efficacy and safety from a randomised, controlled trial" *Ann. Rheum. Dis.* (OP0004) 62(Suppl. 1) (2003).

Stahl, D. et al., "Serum affinity chromatography for the detection of IgG alloantibodies in a patient with high-titer IgM cold agglutinins" *Vox Sanguinis* 74(4) :253-255 (1998).

Stasi et al., "Rituximab chimeric anti-CD20 monoclonal antibody treatment for adults with chronic idiopathic thrombocytopenic purpura" *Blood* 98(4) :952-957 (Aug. 15, 2001).

Stegeman et al., "Association of Chronic Nasal Carriage of *Staphylococcus aureus* and Higher Relapse Rates in Wegener Granulomatosis" *Annals of Internal Medicine* 120(1) :12-17 (Jan. 1, 1994).

Stegeman et al., "Trimethoprim-Sulfamethoxazole (co-trimoxazole) for the prevention of relapses of Wegener's Granulomatosis" *New England J. of Medicine* 335(1) :16-20 (Jul. 4, 1996).

Stillwell et al., "Cyclophosphamide-induced bladder toxicity in Wegner's granulomatosis" *Arthritis and Rheumatism* 31(4) :465-470 (Apr. 1988).

Stockinger et al., "Monoclonal Antibodies to Human Cell Surface Antigens" *Current Protocols in Immunology* (Appendix 4A), Coligan et al., John Wiley & Sons, Inc. pp. A.4A.1-A4A.49 (Feb. 2003).

Stockwin and Holmes, "Antibodies as therapeutic agents: Vive la renaissance" *Expert Opinion on Biological Therapy* 3(7) :1133-1152 (2003).

Stone et al., "A Disease-Specific Activity Index for Wegener's Granulomatosis" *Arthritis and Rheumatism* 44(14) :912-920 (Apr. 2001).

Stone et al., "Etanercept Combined With Conventional Treatment in Wegner's Granulomatosis" *Arthritis and Rheumatism* 44(5) :1149-1154 (May 2001).

Stone et al., "Test Characteristics of Immunofluorescence and ELISA Tests in 856 Consecutive Patients with Possible ANCA Associated Conditions" *Arthritis Care and Research* 13:424-434 (2000).

Strand et al., "Outcome Measures To Be Used in Clinical Trials in Systemic Lupus Erythematosus" *J. Rheumatology* 26:490-497 (1999).

Su and Madaio, "Recent Advances in the Pathogenesis of Lupus Nephritis: Autoantibodies and B Cells" *Seminars in Nephrology* 23(6) :564-568 (Nov. 2003).

Szczepanski et al., "Safety Data From 48 weeks Follow-Up of a Randomised Controlled trial of Rituximab in Patients with Rheumatoid Arthritis" *Arthritis Rheumatology* (Abstract #204) 48(9) :S121 (2003).

Tahir et al., "Humanized anti-CD20 monoclonal antibody in the treatment of severe resistant systemic lups erythematosus in a patient with antibodies against rituximab" *Rheumatology* 44(4) :561-562 (2005).

Taylor, "Antibody therapy for rheumatoid-arthritis" *Current Opinion in Pharmacology* 3(3) :323-328 (2003).

Tedder et al., "The B Cell Surface Molecule B1 is Functionally Linked with B Cell Activation and Differentiation" *The Journal of Immunology* 135 (2) :973-979 (Aug. 1985).

Tedder et al., "The CD20 Surface Molecule of B Lymphocytes Functions as a Calcium Channel" *J. Cell. Biochem.* (Abstract #M 023) 14D:195 (1990).

ten Cate et al., "Anti-CD20 monoclonal antibody (rituximab) for refractory autoimmune thrombocytopenia in a girl with systemic lupus erythematosus" *Rheumatology* 43(2) :244-245 (Feb. 2004).

Tokunaga et al., "Down-regulation ot CD40 and CD80 on B cells in patients with life-threatening systemic lupus erythematosus after successful treatment with rituximab" *Rheumatology* 44(2) :176-182 (2005).

Tomietto et al., "B cell depletion may lead to normalization of anti-platelet, anti-erythrocyte and antiphospholipid antibodies in systemic lupus erythematosus" *Thromb. Haemost.* 92:1150-1153 (2004).

Treon et al., "The Use of Rituximab in the Treatment of Malignant and Nonmalignant Plasma Cell Disorders" *Seminars in Oncology* 27(6, Suppl. 12) :79-85 (Dec. 2000).

Tuscano et al., "B lymphocytes contribute to autoimmune disease pathogenesis: Current trends and clinical implications" *Autoimmunity Reviews* 2(2) :101-108 (2003).

Tuscano et al., "Successful treatment of Infliximab-refractory rheumatoid arthritis with rituximab" *Annual Scientific Meeting of the American College of Rheumatology* (Presentation #LB11, Poster #444), New Orleans, LA (Oct. 24-29, 2002).

Uchida et al., "The innate mononuclear phagocyte network depletes B lymphocytes through Fc receptor-dependent mechanisms during anti-CD20 antibody immunotherapy" *Journal of Experimental Medicine* 199(12) :1659-1669 (Jun. 21, 2004).

Valente, "Chapter 68—Vasculitis and related disorders" *Textbook of Rheumatology*, Saunders, 5th edition, Philadelphia pp. 1079-1101 (1997).

Valentine et al., "Anti-CD20 monoclonal antibody (rituximab, RTX) therapy in a hemodialysis (HD) patient (Pt) with severe systemic lupus erythematosus (SLE)" *Journal of the American Society of Nephrology* (Abstract #PUB064) 13:683A (Sep. 2002).

Valentine et al., "B3.9 Structure and function of the B-cell specific 35-37κDa CD20 protein" *Leukocyte Typing III* (B-cell antigens—papers), McMichael, Ed., Oxford University Press pp. 440-443 (1987).

Valentine et al., "Phosphorylation of the CD20 Phosphoprotein in Resting B Lymphocytes" *J. Bio. Chem.* 264(19) :11282-11287 (1989).

Villar et al., "Intrathecal IgM synthesis is a prognostic factor in multiple sclerosis" *Ann Neurol.* 53(2) :222-226 (Feb. 2003).

Virgolini and Marzocchi, "Rituximab in autoimmune diseases" *Biomedicine & Pharmacotherapy* 58:299-309 (2004).

Vugmeyster et al., "Depletion of B cells by a humanized anti-CD20 antibody PRO70769 in Macaca fascicularis" *J. Immunotherapy* 28(3) :212-219 (May/Jun. 2005).

Wallace, "Management of lupus erythematosus: recent insights" *Current Opinion in Rheumatology* 14(3) :212-219 (May 2002).

Wei et al., "Development and validation of a cell-based bioassay for the detection of neutralizing antibodies against recombinant human erythropoietin in clinical studies" *J. Immunol. Methods* 293(1-2) : 115-126 (Oct. 2004).

Weide et al., "Successful long-term treatment of systemic lupus erythematosus with rituximab maintenance therapy" *Lupus* 12:779-782 (2003).

Weinshenker et al., "The natural history of multiple sclerosis: a geographically based study. I. Clinical course and disability" *Brain* 112:133-146 (Feb. 1989).

Weinstein et al., "B-cell biology" *Rheumatic Disease Clinics of North America* 30(1) :159-174 (2004).

Weyand and Goronzy, "Ectopic Germinal Center Formation in Rheumatoid Synovitis" *Ann. N.Y. Acad. Sci.* 987:140-149 (2003).

Wiestner et al., "Rituximab in the treatment of acquired factor VIII inhibitors" *Blood* 100 (9) :3426-3428 (Nov. 1, 2002).

Wiik, "Delineation of a standard procedure for indirect immunofluorescence detection of ANCA" *APMIS* 97(Suppl. 6) :12-13 (1989).

Wingerchuk et al., "Multiple sclerosis: current pathophysiological concepts" *Laboratory Investigation* 81(3) :263-281 (Mar. 2001).

Wolinsky, "The diagnosis of primary progressive multiple sclerosis" *J Neurol Sci.* 206(2) :145-152 (Feb. 15, 2003).

Wylam et al., "Successful treatment of refractory myasthenia gravis using rituximab: a pediatric case report" *J Pediatr.* 143(5) :674-677 (Nov. 2003).

Xiao et al., "Antineutrophil cytoplasmic autoantibodies specific for myeloperoxidase cause glomerulonephritis and vasculitis in mice" *J. Clin. Invest.* 110(7) :955-963 (Oct. 2002).

Zaja et al., "B-cell depletion with rituximab as treatment for immune hemolytic anemia and chronic thrombocytopenia" *Haematologica* 87(2) :189-195 (Feb. 2002).

Zaja et al., "Efficacy and safety of rituximab in type II mixed cryoglobulinemia" *Blood* 101(10) :3827-3834 (May 15, 2003).

Zaja et al., "Rituximab for myasthenia gravis developing after bone marrow transplant" *Neurology* 55(7) :1062-1063 (Oct. 10, 2000).

Zaja et al., "Rituximab for the treatment of type II mixed cryoglobulinemia" *Haematologica* 84(12) :1157-1158 (Dec. 1999).

Zaja et al., "Rituximab in a case of cold agglutinin disease" *Br J Haematol.* 115:232-233 (Oct. 2001).

Zaja et al., "The B-cell compartment as the selective target for the treatment of immune thrombocytopenias" *Haematologica* 88(5) : 538-546 (May 2003).

Zaya, F. et al., "Rituximab for the treatment of autoimmune disease" *Blood* (Abstract #3770) 98(11 Part 2) :41b (2001).

Zecca et al., "Rituximab for the treatment of refractory autoimmune hemolytic anemia in children" *Blood* 101(10) :3857-3861 (May 15, 2003).

Zeman et al., "Cerebrospinal fluid cytologic findings in multiple sclerosis. A comparison between patient subgroups" *Acta Cytol.* 45(1) :51-59 (Jan.-Feb. 2001).

Higashida et al., "Treatment of DMARD-Refractory Rheumatoid Arthritis With Rituximab" Annual Scientific Meeting of the American College of Rheumatology (Abstract #LB11), New Orleans, LA (Oct. 2002).

Stone and Specks, "Rituximab Therapy for the Induction of Remission and Tolerance in ANCA-associated Vasculitis. Clinical Trial Research Summary of the 2002-2003 Immune Tolerance Network" American Society of Nephrology (11th International Vasculitis and ANCA workshop)(Poster 88).

\* cited by examiner

FIG. 1A

Sequence Alignment of Variable Light Domains

```
              FR1                      CDR1
              10        20             30              40
2H7      QIVLSQSPAILSASPGEKVTMTC  [RASSSVS-YMH]   WYQQKP
           * *         *  ** hu2H7.v16 DIQMTQSPSSLSASVGDRVTITC  [RASSSVS-YMH]   WYQQKP
                                    *  *  * ** hum KI   DIQMTQSPSSLSASVGDRVTITC  [RASQSISNYLA]   WYQQKP

FR2      CDR2               FR3
                       50         60         70         80
2H7      GSSPKPWIY   [APSNLAS]  GVPARFSGSGSGTSYSLTISRVEA
          * *    *               *        *       ** hu2H7.v16 GKAPKPLIY  [APSNLAS]  GVPSRFSGSGSGTDFTLTISSLQP
              *       * * * hum KI   GKAPKLLIY   [AASSLES]  GVPSRFSGSGSGTDFTLTISSLQP

CDR3         FR4
                     90           100
2h7      EDAATYYC  [QQWSFNPPT]  FGAGTKLELKR
           *                     *   *  *

HU2h7.V16 EDFATYYC [QQWSFNPPT]  FGQGTKVEIKR
                    **** *

HUM ki   EDFATYYC  [QQYNSLPWT]  FGQGTKVEIKR
```

FIG. 1B

Sequence Alignment of Variable Heavy Domains

```
                        FR1                           CDR1
                  10          20              30              40
2H7         QAYLQQSGAELVRPGASVKMSCKAS    GYTFTSYNMH     WVKQT
            ***  **   **   *   * ***  *              * *
hu2H7.v16   EVQLVESGGGLVQPGGSLRLSCAAS    GYTFTSYNMH     WVRQA
                                           *  *    *
hum III     EVQLVESGGGLVQPGGSLRLSCAAS    GFTFSSYAMS     WVRQA FR2            CDR2                   FR3
                    50    a       60           70          80
2H7         PRQGLEWIG    AIYPGNGDTSYNQKFKG    KATLTVDKSSSTAYM
             **    *                         ** **     ** * *
hu2H7.v16   PGKGLEWVG    AIYPGNGDTSYNQKFKG    RFTISVDKSKNTLYL
                  *      * ****  * * ****      * *
hum III     PGKGLEWVA    VISGDGGSTYYADSVKG    RFTISRDNSKNTLYL CDR3            FR4
                       abc    90    100abcde         110
2H7         QLSSLTSEDSAVYFCAR    VVYYSNSYWYFDV    WGTGTTVTVSS
             **  **    *   *                        *
hu2H7.V16   QMNSLRAEDTAVYYCAR    VVYYSNSYWYFDV    WGQGTLVTVSS
                                 *******  *** *
hum III     QMNSLRAEDTAVYYCAR    GRVGYSLY---DY    WGQGTLVTVSS
```

FIG. 2

Light chain alignment

```
             1                                32
hu2H7.v16    DIQMTQSPSSLSASVGDRVTITCRASSSVSYMHWYQQKPGKAPKPLIYAP
             **********************************.***************
hu2H7.v511   DIQMTQSPSSLSASVGDRVTITCRASSSVSYLHWYQQKPGKAPKPLIYAP 52
hu2H7.v16    SNLASGVPSRFSGSGSGTDFTLTISSLQPEDFATYYCQQWSFNPPTFGQG
             ***********************************.*************
hu2H7.v511   SNLASGVPSRFSGSGSGTDFTLTISSLQPEDFATYYCQQWAFNPPTFGQG 102
hu2H7.v16    TKVEIKRTVAAPSVFIFPPSDEQLKSGTASVVCLLNNFYPREAKVQWKVD
             **************************************************
hu2H7.v511   TKVEIKRTVAAPSVFIFPPSDEQLKSGTASVVCLLNNFYPREAKVQWKVD 152
hu2H7.v16    NALQSGNSQESVTEQDSKDSTYSLSSTLTLSKADYEKHKVYACEVTHQGL
             **************************************************
hu2H7.v511   NALQSGNSQESVTEQDSKDSTYSLSSTLTLSKADYEKHKVYACEVTHQGL 202       214
hu2H7.v16    SSPVTKSFNRGEC
             *************
hu2H7.v511   SSPVTKSFNRGEC
```

FIG. 3

Heavy chain alignment

```
             1
hu2H7.v16    EVQLVESGGGLVQPGGSLRLSCAASGYTFTSYNMHW
             ***********************************
hu2H7.v511   EVQLVESGGGLVQPGGSLRLSCAASGYTFTSYNMHW 37           52a                          82abc
hu2H7.v16    VRQAPGKGLEWVGAIYPGNGDTSYNQKFKGRFTISVDKSKNTLYLQMNSL
             ***************************  ********************
hu2H7.v511   VRQAPGKGLEWVGAIYPGNGATSYNQKFKGRFTISVDKSKNTLYLQMNSL 83           100abcde       113
hu2H7.v16    RAEDTAVYYCARVVYYSNSYWYFDVWGQGTLVTVSS
             ****************   *****************
hu2H7.v511   RAEDTAVYYCARVVYYSYRYWYFDVWGQGTLVTVSS 118
hu2H7.v16    ASTKGPSVFPLAPS
             **************
hu2H7.v511   ASTKGPSVFPLAPS 132
hu2H7.v16    SKSTSGGTAALGCLVKDYFPEPVTVSWNSGALTSGVHTFPAVLQSSGLYS
             **************************************************
hu2H7.v511   SKSTSGGTAALGCLVKDYFPEPVTVSWNSGALTSGVHTFPAVLQSSGLYS 182
hu2H7.v16    LSSVVTVPSSSLGTQTYICNVNHKPSNTKVDKKVEPKSCDKTHTCPPCPA
             **************************************************
hu2H7.v511   LSSVVTVPSSSLGTQTYICNVNHKPSNTKVDKKVEPKSCDKTHTCPPCPA 232
hu2H7.v16    PELLGGPSVFLFPPKPKDTLMISRTPEVTCVVVDVSHEDPEVKFNWYVDG
             **************************************************
hu2H7.v511   PELLGGPSVFLFPPKPKDTLMISRTPEVTCVVVDVSHEDPEVKFNWYVDG 282
hu2H7.v16    VEVHNAKTKPREEQYNSTYRVVSVLTVLHQDWLNGKEYKCKVSNKALPAP
             ******************.******************************  *****
hu2H7.v511   VEVHNAKTKPREEQYNATYRVVSVLTVLHQDWLNGKEYKCKVSNAALPAP 332
hu2H7.v16    IEKTISKAKGQPREPQVYTLPPSREEMTKNQVSLTCLVKGFYPSDIAVEW
             *  ***********************************************
hu2H7.v511   IAATISKAKGQPREPQVYTLPPSREEMTKNQVSLTCLVKGFYPSDIAVEW 382
hu2H7.v16    ESNGQPENNYKTTPPVLDSDGSFFLYSKLTVDKSRWQQGNVFSCSVMHEA
             **************************************************
hu2H7.v511   ESNGQPENNYKTTPPVLDSDGSFFLYSKLTVDKSRWQQGNVFSCSVMHEA 432           447
hu2H7.v16    LHNHYTQKSLSLSPGK
             ****************
hu2H7.v511   LHNHYTQKSLSLSPGK
```

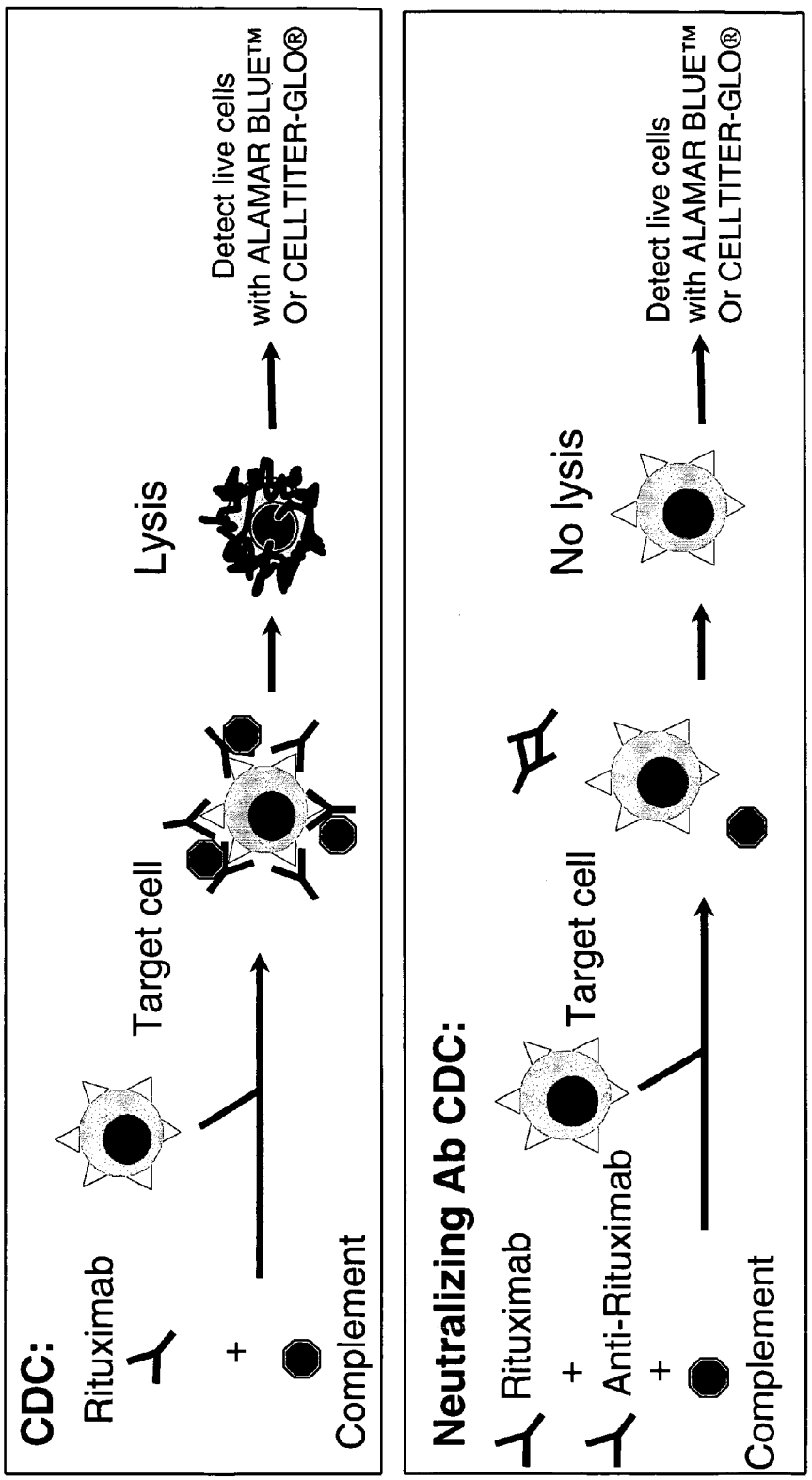
FIG._4
CDC: Complement-Dependent Cytotoxicity as a Neutralizing Ab Assay

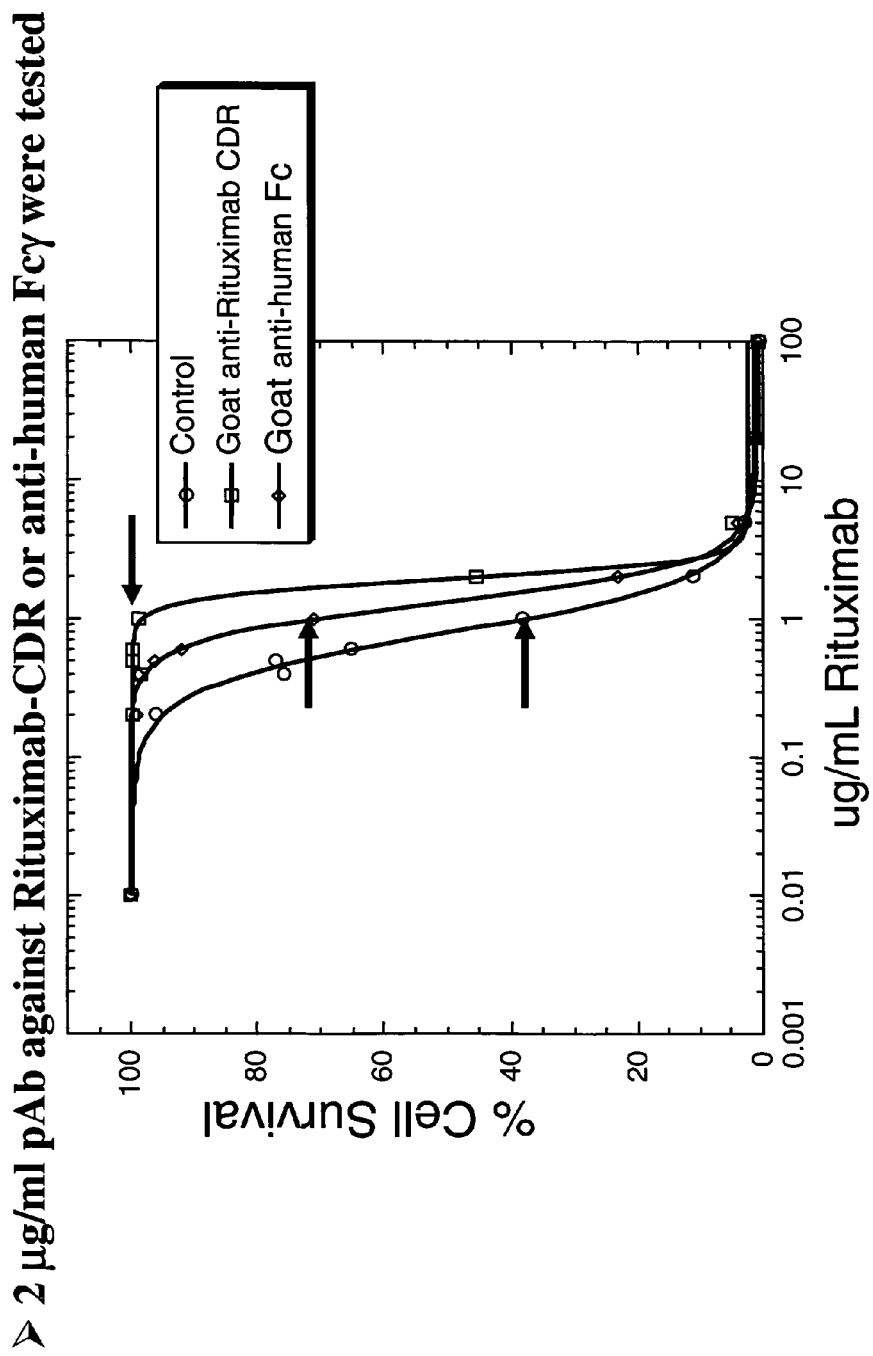
FIG._5
CDC as a Neutralizing Ab Assay

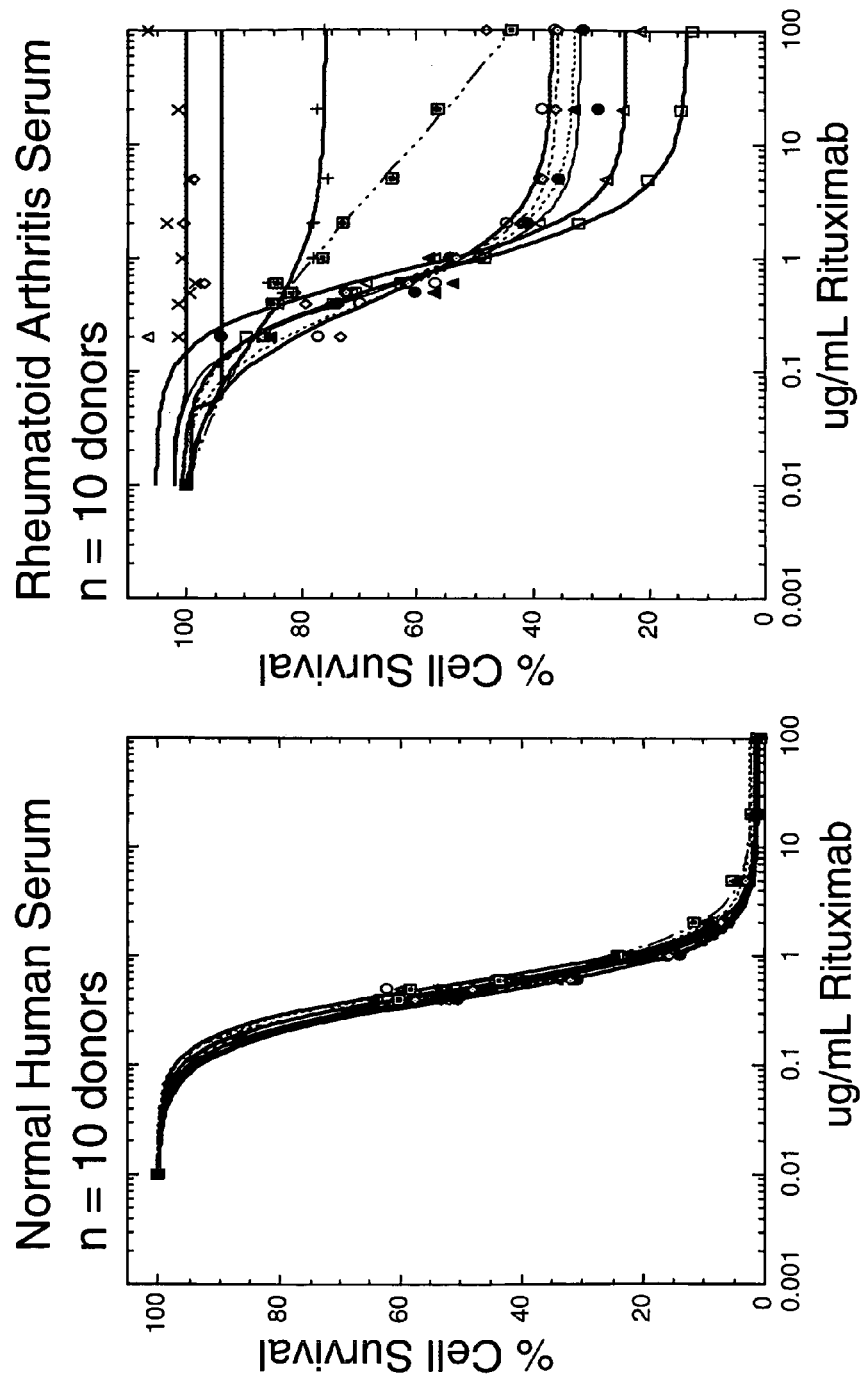
FIG._6 CDC NAb Assay: Serum Tolerance

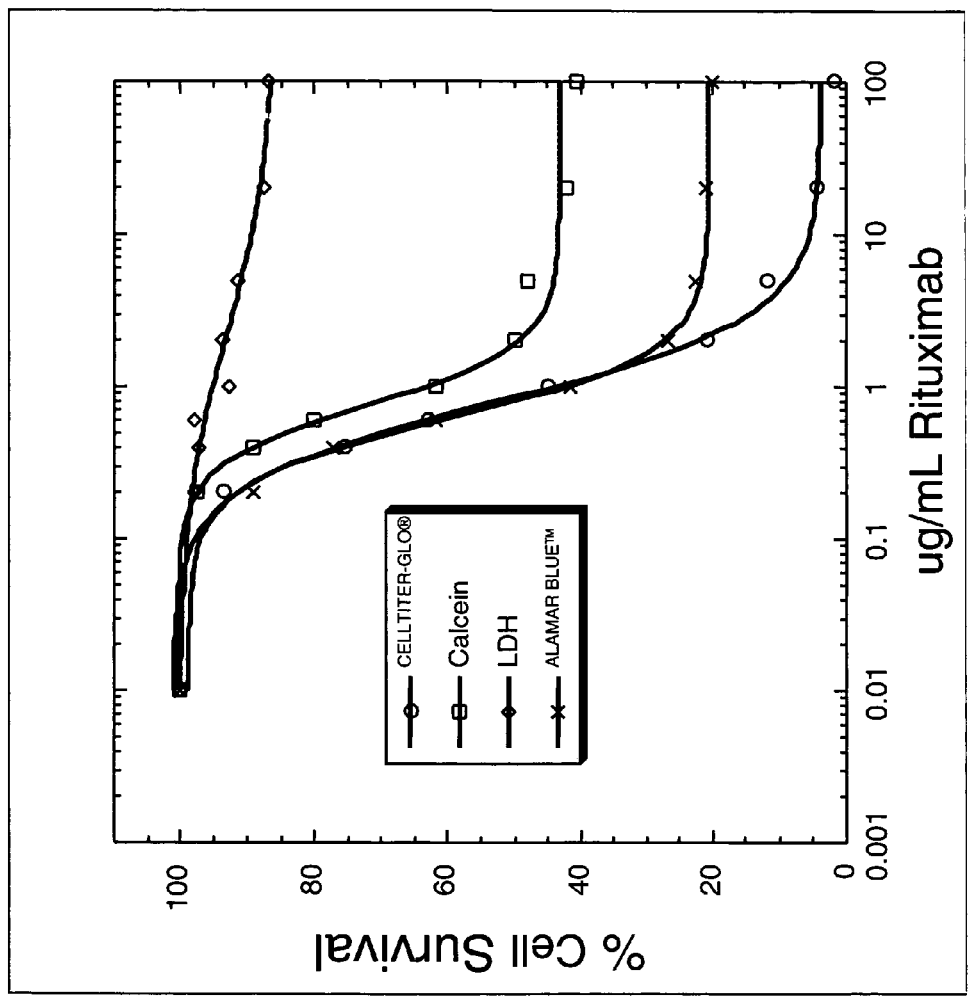
FIG._7

RA Serum Interference:
ALAMAR BLUE™ vs. CELLTITER-GLO®

FIG._9
Serum pre-treatment procedure

Autoimmune Serum Pre-treatment

FIG._11

PRETREATMENT OF A BIOLOGICAL SAMPLE FROM AN AUTOIMMUNE DISEASE SUBJECT

This is a non-provisional application claiming priority under 35 USC § 119 to Provisional Application No. 60/682,990 filed May 20, 2005, the entire disclosure of which is hereby incorporated by reference.

FIELD OF THE INVENTION

The present invention concerns a method for pretreating a biological sample from an autoimmune disease subject in order to avoid interference, especially where the sample is to be subjected to a cell-based biological activity assay, such as a neutralizing antibody assay.

BACKGROUND OF THE INVENTION

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naïve B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody, but instead produce the antibody in a form that can be secreted. Secreted antibodies are the major effector molecules of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes. Valentine et al., *J. Biol. Chem.* 264(19):11282-11287 (1989) and Einfeld et al., *EMBO J.* 7(3):711-717 (1988). The antigen is also expressed on greater than 90% of B-cell non-Hodgkin's lymphomas (NHL) (Anderson et al. *Blood* 63(6):1424-1433 (1984)), but is not found on hematopoietic stem cells, pro-B cells, normal plasma cells, or other normal tissues (Tedder et al. *J. Immunol.* 135(2):973-979 (1985)). CD20 regulates an early step(s) in the activation process for cell-cycle initiation and differentiation (Tedder et al., supra), and possibly functions as a calcium-ion channel. Tedder et al., *J. Cell. Biochem.* 14D: 195 (1990).

Given the expression of CD20 in B-cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody that is utilized, and thus, the available approaches to targeting the CD20 antigen can vary considerably.

The rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). Rituximab is indicated for the treatment of patients with relapsed or refractory low-grade or follicular, CD20-positive, B-cell non-Hodgkin's lymphoma. In vitro, rituximab has been demonstrated to mediate complement-dependent cytotoxicity (CDC) and antibody-dependent cellular cytotoxicity (ADCC) and to induce apoptosis (Reff et al., *Blood* 83(2):435-445 (1994); Maloney et al., *Blood* 88:637a (1996); Manches et al., *Blood* 101:949-954 (2003)). Synergy between rituximab and chemotherapies and toxins has also been observed experimentally. In particular, rituximab sensitizes drug-resistant human B-cell lymphoma cell lines to the cytotoxic effects of doxorubicin, CDDP, VP-16, diphtheria toxin, and ricin (Demidem et al., *Cancer Chemotherapy & Radiopharmaceuticals* 12(3):177-186 (1997)). In vivo preclinical studies have shown that rituximab depletes B cells from the peripheral blood, lymph nodes, and bone marrow of cynomolgus monkeys. Reff et al., *Blood* 83:435-445 (1994).

Rituximab has also been studied in a variety of non-malignant autoimmune disorders, in which B cells and autoantibodies appear to play a role in disease pathophysiology. Edwards et al., *Biochem Soc. Trans.* 30:824-828 (2002). Rituximab has been reported to potentially relieve signs and symptoms of, for example, rheumatoid arthritis (RA) (Leandro et al., *Ann. Rheum. Dis.* 61:883-888 (2002); Edwards et al., *Arthritis Rheum.*, 46 (Suppl. 9): S46 (2002); Stahl et al., *Ann. Rheum. Dis.*, 62 (Suppl. 1): OP004 (2003); Emery et al., *Arthritis Rheum.* 48(9): S439 (2003)), lupus (Eisenberg, *Arthritis. Res. Ther.* 5:157-159 (2003); Leandro et al. *Arthritis Rheum.* 46: 2673-2677 (2002); Gorman et al., *Lupus*, 13: 312-316 (2004)), immune thrombocytopenic purpura (D'Arena et al., *Leuk. Lymphoma* 44:561-562 (2003); Stasi et al., *Blood*, 98: 952-957 (2001); Saleh et al., *Semin. Oncol.*, 27 (Supp 12):99-103 (2000); Zaia et al., *Haematolgica*, 87: 189-195 (2002); Ratanatharathorn et al., *Ann. Int. Med.*, 133: 275-279 (2000)), pure red cell aplasia (Auner et al., *Br. J. Haematol.*, 116: 725-728 (2002)); autoimmune anemia (Zaja et al., *Haematologica* 87:189-195 (2002) (erratum appears in *Haematologica* 87:336 (2002)), cold agglutinin disease (Layios et al., *Leukemia*, 15: 187-8 (2001); Berentsen et al., *Blood*, 103: 2925-2928 (2004); Berentsen et al., *Br. J. Haematol.*, 115: 79-83 (2001); Bauduer, *Br. J. Haematol.*, 112: 1083-1090 (2001); Damiani et al., *Br. J. Haematol.*, 114: 229-234 (2001)), type B syndrome of severe insulin resistance (Coll et al., *N. Engl. J. Med.*, 350: 310-311 (2004), mixed cryoglobulinemia (DeVita et al., *Arthritis Rheum.* 46 Suppl. 9:S206/S469 (2002)), myasthenia gravis (Zaja et al., *Neurology*, 55: 1062-63 (2000); Wylam et al., *J. Pediatr.*, 143: 674-677 (2003)), Wegener's granulomatosis (Specks et al., *Arthritis & Rheumatism* 44: 2836-2840 (2001)), refractory pemphigus vulgaris (Dupuy et al., *Arch Dermatol.*, 140:91-96 (2004)), dermatomyositis (Levine, *Arthritis Rheum.*, 46 (Suppl. 9):S1299 (2002)), Sjogren's syndrome (Somer et al., *Arthritis & Rheumatism*, 49: 394-398 (2003)), active type-II mixed cryoglobulinemia (Zaja et al., *Blood*, 101: 3827-3834 (2003)), pemphigus vulgaris (Dupay et al., *Arch. Dermatol.*, 140: 91-95 (2004)), autoimmune neuropathy (Pestronk et al., *J. Neurol. Neurosurg. Psychiatry* 74:485-489 (2003)), paraneoplastic opsoclonus-myoclonus syndrome (Pranzatelli et al. *Neurology* 60(Suppl. 1) PO5.128:A395 (2003)), and relapsing-remitting multiple sclerosis (RRMS). Cross et al. (abstract) "Preliminary results from a phase II trial of rituximab in MS" Eighth Annual Meeting of the Americas Committees for Research and Treatment in Multiple Sclerosis, 20-21 (2003).

A Phase II study (WA16291) has been conducted in patients with rheumatoid arthritis (RA), providing 48-week follow-up data on safety and efficacy of rituximab. Emery et al. *Arthritis Rheum* 48(9):S439 (2003); Szczepanski et al. *Arthritis Rheum* 48(9):S121 (2003); Edwards et al., "Efficacy of B-cell-targeted therapy with rituximab in patients with rheumatoid arthritis" *N Engl. J. Med.* 350:2572-82 (2004). A total of 161 patients were evenly randomized to four treatment arms: methotrexate, rituximab alone, rituximab plus methotrexate, and rituximab plus cyclophosphamide (CTX). The treatment regimen of rituximab was one gram administered intravenously on days 1 and 15. Infusions of rituximab in most patients with RA were well tolerated by most patients, with 36% of patients experiencing at least one adverse event during their first infusion (compared with 30% of patients receiving placebo). Overall, the majority of adverse events was considered to be mild to moderate in severity and was well balanced across all treatment groups. There were a total of 19 serious adverse events across the four arms over the 48 weeks, which were slightly more frequent in the rituximab/CTX group. The incidence of infections was well balanced across all groups. The mean rate of serious infection in this RA patient population was 4.66 per 100 patient-years, which is lower than the rate of infections requiring hospital admission in RA patients (9.57 per 100 patient-years) reported in a community-based epidemiologic study. Doran et al., *Arthritis Rheum.* 46:2287-2293 (2002).

The reported safety profile of rituximab in a small number of patients with neurologic disorders, including autoimmune neuropathy (Pestronk et al., supra), opsoclonus-myoclonus syndrome (Pranzatelli et al., supra), and RRMS (Cross et al., supra), was similar to that reported in oncology or RA. In an ongoing investigator-sponsored trial (IST) of rituximab in combination with interferon-β (IFN-β) or glatiramer acetate in patients with RRMS (Cross et al., supra), 1 of 10 treated patients was admitted to the hospital for overnight observation after experiencing moderate fever and rigors following the first infusion of rituximab, while the other 9 patients completed the four-infusion regimen without any reported adverse events.

Patents and patent publications concerning CD20 antibodies and CD20 binding molecules include U.S. Pat. Nos. 5,776,456, 5,736,137, 5,843,439, 6,399,061, and 6,682,734, as well as US 2002/0197255, US 2003/0021781, US 2003/0082172, US 2003/0095963, US 2003/0147885 (Anderson et al.); U.S. Pat. No. 6,455,043, US 2003/0026804, and WO 2000/09160 (Grillo-Lopez, A.); WO 2000/27428 (Grillo-Lopez and White); WO 2000/27433 and US 2004/0213784 (Grillo-Lopez and Leonard); WO 2000/44788 (Braslawsky et al.); WO 2001/10462 (Rastetter, W.); WO01/10461 (Rastetter and White); WO 2001/10460 (White and Grillo-Lopez); US 2001/0018041, US 2003/0180292, WO 2001/34194 (Hanna and Hariharan); US 2002/0006404 and WO 2002/04021 (Hanna and Hariharan); US 2002/0012665 and WO 2001/74388 (Hanna, N.); US 2002/0058029 (Hanna, N.); US 2003/0103971 (Hariharan and Hanna); US 2002/0009444 and WO 2001/80884 (Grillo-Lopez, A.); WO 2001/97858 (White, C.); US 2002/0128488 and WO 2002/34790 (Reff, M.); WO 2002/060955 (Braslawsky et al.); WO 2002/096948 (Braslawsky et al.); WO 2002/079255 (Reff and Davies); U.S. Pat. No. 6,171,586 and WO 1998/56418 (Lam et al.); WO 1998/58964 (Raju, S.); WO 1999/22764 (Raju, S.); WO 1999/51642, U.S. Pat. Nos. 6,194,551, 6,242,195, 6,528,624 and 6,538,124 (Idusogie et al.); WO 2000/42072 (Presta, L.); WO 2000/67796 (Curd et al.); WO 2001/03734 (Grillo-Lopez et al.); US 2002/0004587 and WO 2001/77342 (Miller and Presta); US 2002/0197256 (Grewal, I.); US 2003/0157108 (Presta, L.); WO 04/056312 (Lowman et al.); US 2004/0202658 and WO 2004/091657 (Benyunes, K.); WO 2005/000351 (Chan, A.); US 2005/0032130A1 (Beresini et al.); US 2005/0053602A1 (Brunetta, P.); U.S. Pat. Nos. 6,565,827, 6,090,365, 6,287,537, 6,015,542, 5,843,398, and 5,595,721, (Kaminski et al.); U.S. Pat. Nos. 5,500,362, 5,677,180, 5,721,108, 6,120,767, and 6,652,852 (Robinson et al.); U.S. Pat. No. 6,410,391 (Raubitschek et al.); U.S. Pat. No. 6,224,866 and WO00/20864 (Barbera-Guillem, E.); WO 2001/13945 (Barbera-Guillem, E.); US2005/0079174A1 (Barbera-Guillem et al.); WO 2000/67795 (Goldenberg); US 2003/0133930 and WO 2000/74718 (Goldenberg and Hansen); US 2003/0219433 and WO 2003/68821 (Hansen et al.); WO2004/058298 (Goldenberg and Hansen); WO 2000/76542 (Golay et al.); WO 2001/72333 (Wolin and Rosenblatt); U.S. Pat. No. 6,368,596 (Ghetie et al.); U.S. Pat. No. 6,306,393 and US 2002/0041847 (Goldenberg, D.); US 2003/0026801 (Weiner and Hartmann); WO 2002/102312 (Engleman, E.); US 2003/0068664 (Albitar et al.); WO 2003/002607 (Leung, S.); WO 2003/049694, US2002/0009427, and US 2003/0185796 (Wolin et al.); WO 2003/061694 (Sing and Siegall); US 2003/0219818 (Bohen et al.); US 2003/0219433 and WO 2003/068821 (Hansen et al.); US 2003/0219818 (Bohen et al.); US2002/0136719 (Shenoy et al.); WO 2004/032828 (Wahl et al.); and WO 2002/56910 (Hayden-Ledbetter). See also U.S. Pat. No. 5,849,898 and EP 330,191 (Seed et al.); EP332,865A2 (Meyer and Weiss); U.S. Pat. No. 4,861,579 (Meyer et al.); US2001/0056066 (Bugelski et al.); WO 1995/03770 (Bhat et al.); US 2003/0219433 A1 (Hansen et al.); WO 2004/035607 (Teeling et al.); US 2004/0093621 (Shitara et al.); WO 2004/103404 (Watkins et al.); WO 2005/000901 (Tedder et al.); US 2005/0025764 (Watkins et al.); WO2005/016969 and US 2005/0069545 A1 (Carr et al.); WO 2005/014618 (Chang et al.).

Publications concerning therapy with rituximab include: Perotta and Abuel, "Response of chronic relapsing ITP of 10 years duration to rituximab" Abstract # 3360 Blood 10(1) (part 1-2): p. 88B (1998); Perotta et al., "Rituxan in the treatment of chronic idiopathic thrombocytopenic purpura (ITP)", *Blood*, 94: 49 (abstract) (1999); Matthews, R., "Medical Heretics" *New Scientist* (7 Apr., 2001); Leandro et al., "Lymphocyte depletion in rheumatoid arthritis: early evidence for safety, efficacy and dose response" *Arthritis and Rheumatism* 44(9): S370 (2001); Leandro et al., "An open study of B lymphocyte depletion in systemic lupus erythematosus", *Arthritis and Rheumatism*, 46:2673-2677 (2002), wherein during a 2-week period, each patient received two 500-mg infusions of rituximab, two 750-mg infusions of cyclophosphamide, and high-dose oral corticosteroids, and wherein two of the patients treated relapsed at 7 and 8 months, respectively, and have been retreated, although with different protocols; Weide et al. "Successful long-term treatment of systemic lupus erythematosus with rituximab maintenance therapy" *Lupus*, 12: 779-782 (2003), wherein a patient was treated with rituximab (375 mg/m$^2$×4, repeated at weekly intervals) and further rituximab applications were delivered every 5-6 months and then maintenance therapy was received with rituximab 375 mg/m$^2$ every three months, and a second patient with refractory SLE was treated successfully with rituximab and is receiving maintenance therapy every three months, with both patients responding well to rituximab therapy; Edwards and Cambridge, "Sustained improvement in rheumatoid arthritis following a protocol designed to deplete B lymphocytes" *Rheumatology* 40:205-211 (2001);

Cambridge et al., "B lymphocyte depletion in patients with rheumatoid arthritis: serial studies of immunological parameters" *Arthritis Rheum.*, 46 (Suppl. 9): S1350 (2002); Edwards et al., "Efficacy and safety of rituximab, a B-cell targeted chimeric monoclonal antibody: A randomized, placebo controlled trial in patients with rheumatoid arthritis. *Arthritis and Rheumatism* 46(9): S197 (2002); Pavelka et al., *Ann. Rheum. Dis.* 63: (S1):289-90 (2004); Emery et al., *Arthritis Rheum.* 50 (S9):S659 (2004); Levine and Pestronk, "IgM antibody-related polyneuropathies: B-cell depletion chemotherapy using rituximab" *Neurology* 52: 1701-1704 (1999); DeVita et al., "Efficacy of selective B cell blockade in the treatment of rheumatoid arthritis" *Arthritis & Rheum* 46:2029-2033 (2002); Hidashida et al. "Treatment of DMARD-refractory rheumatoid arthritis with rituximab." Presented at the *Annual Scientific Meeting of the American College of Rheumatology*; October 24-29; New Orleans, La. 2002; Tuscano, J. "Successful treatment of infliximab-refractory rheumatoid arthritis with rituximab" Presented at the *Annual Scientific Meeting of the American College of Rheumatology*; October 24-29; New Orleans, La. 2002; "Pathogenic roles of B cells in human autoimmunity; insights from the clinic" Martin and Chan, *Immunity* 20:517-527 (2004); Silverman and Weisman, "Rituximab Therapy and Autoimmune Disorders, Prospects for Anti-B Cell Therapy", *Arthritis and Rheumatism*, 48: 1484-1492 (2003); Kazkaz and Isenberg, "Anti B cell therapy (rituximab) in the treatment of autoimmune diseases", *Current opinion in pharmacology*, 4: 398-402 (2004); Virgolini and Vanda, "Rituximab in autoimmune diseases", *Biomedicine & pharmacotherapy*, 58: 299-309(2004); Klemmer et al., "Treatment of antibody mediated autoimmune disorders with a AntiCD20 monoclonal antibody Rituximab", *Arthritis And Rheumatism*, 48: (9): S624-S624(2003); Kneitz et al., "Effective B cell depletion with rituximab in the treatment of autoimmune diseases", *Immunobiology*, 206: 519-527 (2002); Arzoo et al., "Treatment of refractory antibody mediated autoimmune disorders with an anti-CD20 monoclonal antibody (rituximab)" *Annals of the Rheumatic Diseases*, 61 (10), p922-4 (2002) *Comment in Ann Rheum Dis.* 61: 863-866 (2002); "Future Strategies in Immunotherapy" by Lake and Dionne, in *Burger's Medicinal Chemistry and Drug Discovery* (2003 by John Wiley & Sons, Inc.) Article Online Posting Date: Jan. 15, 2003 (Chapter 2"Antibody-Directed Immunotherapy"); Liang and Tedder, *Wiley Encyclopedia of Molecular Medicine*, Section: CD20 as an Immunotherapy Target, article online posting date: 15 Jan., 2002 entitled "CD20"; Appendix 4A entitled "Monoclonal Antibodies to Human Cell Surface Antigens" by Stockinger et al., eds: Coligan et al., in *Current Protocols in Immunology* (2003 John Wiley & Sons, Inc) Online Posting Date: May, 2003; Print Publication Date: February, 2003; Penichet and Morrison, "CD Antibodies/molecules: Definition; Antibody Engineering" in *Wiley Encyclopedia of Molecular Medicine* Section: Chimeric, Humanized and Human Antibodies; posted online 15 Jan., 2002; Specks et al. "Response of Wegener's granulomatosis to anti-CD20 chimeric monoclonal antibody therapy" *Arthritis & Rheumatism* 44:2836-2840 (2001); online abstract submission and invitation Koegh et al., "Rituximab for Remission Induction in Severe ANCA-Associated Vasculitis: Report of a Prospective Open-Label Pilot Trial in 10 Patients", American College of Rheumatology, Session Number: 28-100, Session Title: Vasculitis, Session Type: ACR Concurrent Session, Primary Category: 28 Vasculitis, Session Oct. 18, 2004 (http://www.abstractsonline.com/viewer/SearchResults.asp); Eriksson, "Short-term outcome and safety in 5 patients with ANCA-positive vasculitis treated with rituximab", *Kidney and Blood Pressure Research*, 26: 294 (2003); Jayne et al., "B-cell depletion with rituximab for refractory vasculitis" *Kidney and Blood Pressure Research*, 26: 294 (2003); Jayne, poster 88 (11th International Vasculitis and ANCA workshop), 2003 American Society of Nephrology; Stone and Specks, "Rituximab Therapy for the Induction of Remission and Tolerance in ANCA-associated Vasculitis", in the Clinical Trial Research Summary of the 2002-2003 Immune Tolerance Network, http://www.immunetolerance.org/research/autoimmune/trials/stone.html. See also Leandro et al., "B cell repopulation occurs mainly from naïve B cells' in patient with rheumatoid arthritis and systemic lupus erythematosus" *Arthritis Rheum.*, 48 (Suppl 9): S1160 (2003).

US Patent Application No. 2003/0068664 (Albitar et al.) describes an ELISA assay for determining human anti-chimeric antibody (HACA) directed against Rituximab.

US Patent Application No. US 2005/0032130A1 (Beresini and Song) discloses a method of detecting neutralizing antibodies to a therapeutic antibody, such as a CD20 antibody.

Mire-Sluis et al. *J. Immunol. Methods* 289: 1-16 (2004) provides recommendations for the detection and optimization of immunoassays used in detection of host antibodies against biotechnology products.

Hong et al. describe a simple quantitative live cell and anti-idiotypic antibody based ELISA for humanized antibody directed against cell surface protein CD20 (Hong et al. *J Immunol Methods.* 294:189-197 (2004)).

Wei et al., *J Immunol Methods.* 293:115-26 (2004) describe a cell-based bioassay for the detection of neutralizing antibodies against recombinant human erythropoietin in clinical studies.

Leon et al. describe interference by rheumatoid factor activity in the detection of antiavian antibodies in pigeon breeders (Leon et al. *Clin Exp Med.* 2(2):59-67 (2002); erratum in: Leon et al. *Clin Exp Med.* 2(3):157 (2002)). Stahl et al. *Vox Sang.* 74(4):253-255 (1998) refer to serum affinity chromatography for the detection of IgG alloantibodies in a patient with high-titer IgM cold agglutins. Koper et al. *Clin Chem Lab Med.* 36(1):23-28 (1998) quantified IgG and IgM human anti-mouse antibodies (HAMA) interference in CA125 measurements using affinity chromatography. Crowley and Walters refer to the determination of immunoglobulins in blood serum by high-performance affinity chromatography (Crowley and Walters *J Chromatogr.* 266:157-162 (1983)).

See, also, Maeda et al., *Intl. J. Hematology* 74(1):70-75 (2001); Gordon et al., *Blood* 98(11 Part 2):228b (2001); Kaminski et al., *Blood* 96(11 Part 1):734a (2000); Shan et al., *Cancer Immunology Immunotherapy* 48(12):673-683 (2000); Idusogie et al., *Journal of Immunology* 166(4):2571-2575 (2001); Reff et al., *Blood* 83(2):435-445 (1994); and Zaya et al., *Blood* 98(11 Part 2):41b (2001).

SUMMARY OF THE INVENTION

The present invention concerns, at least in part, the discovery that serum from subjects with autoimmune diseases, such as RA or SLE, contains substance(s) which interfere with the performance of a cell-based bioassay, such as a neutralizing antibody assay. Various methods for addressing the problem of interference were attempted, until immunoglobulin affinity purification was identified as the preferred method for removing the interference, so that more reliable results could be achieved in the bioassay.

Accordingly, in a first aspect, the invention provides a method of treating a biological sample from an autoimmune disease subject comprising:

(a) delipidating the sample;
(b) affinity purifying immunoglobulins in the sample;
(c) concentrating the purified immunoglobulins; and
(d) subjecting the concentrated immunoglobulins to a cell-based biological activity assay.

The invention further provides a method of treating a subject with an autoimmune disease comprising:
(a) administering a therapeutic antibody or immunoadhesin to the subject to treat the autoimmune disease;
(b) obtaining a biological sample from the subject;
(c) affinity purifying immunoglobulins in the biological sample; and
(d) subjecting the purified immunoglobulins to a neutralizing antibody assay.

For use in the above methods, the invention further provides a diagnostic kit comprising:
(a) delipidation reagent;
(b) buffers for affinity purification of immunoglobulins; and
(c) instruction manual instructing the user of the diagnostic kit to practice either, or both, of the above methods.

BRIEF DESCRIPTION OF THE DRAWINGS

FIG. 1A is a sequence alignment comparing the amino acid sequences of the variable light domain ($V_L$) of each of murine 2H7 (SEQ ID NO:1), humanized 2H7.v16 variant (SEQ ID NO:2), and the human kappa light chain subgroup I (SEQ ID NO:3). The CDRs of $V_L$ of 2H7 and hu2H7.v16 are as follows: CDR1 (SEQ ID NO:4), CDR2 (SEQ ID NO:5), and CDR3 (SEQ ID NO:6).

FIG. 1B is a sequence alignment comparing the amino acid sequences of the variable heavy domain ($V_H$) of each of murine 2H7 (SEQ ID NO:7), humanized 2H7.v16 variant (SEQ ID NO:8), and the human consensus sequence of the heavy chain subgroup III (SEQ ID NO:9). The CDRs of $V_H$ of 2H7 and hu2H7.v16 are as follows: CDR1 (SEQ ID NO:10), CDR2 (SEQ ID NO:11), and CDR3 (SEQ ID NO:12).

In FIG. 1A and FIG. 1B, the CDR1, CDR2 and CDR3 in each chain are enclosed within brackets, flanked by the framework regions, FR1-FR4, as indicated. 2H7 refers to murine 2H7 antibody. The asterisks in between two rows of sequences indicate the positions that are different between the two sequences. Residue numbering is according to Kabat et al. *Sequences of Immunological Interest*, 5th Ed. Public Health Service, National Institutes of Health, Bethesda, Md. (1991), with insertions shown as a, b, c, d, and e.

FIG. 2 shows an alignment of the mature 2H7.v16 and 2H7.v511 light chains (SEQ ID Nos. 13 and 15, respectively), with Kabat variable domain residue numbering and Eu constant domain residue numbering.

FIG. 3 shows an alignment of the mature 2H7.v16 and 2H7.v511 heavy chains (SEQ ID Nos. 14 and 16, respectively), with Kabat variable domain residue numbering and Eu constant domain residue numbering.

FIG. 4 illustrates complement-dependent cytotoxicity (CDC) as a neutralizing antibody (NAb) assay for Rituximab.

FIG. 5 represents CDC as a NAb assay with respect to the following samples: control, goat anti-rituximab CDR antibodies, and goat anti-human Fc antibodies.

FIG. 6 shows serum tolerance in the CDC NAb assay, comparing results from serum from normal human subjects (left), and serum from rheumatoid arthritis (RA) subjects (right).

FIG. 7 represents assay readout from the CDC NAb assay for: CELLTITER-GLO® Luminescent Cell Viability Assay, calcein, lactose dehydrogenase (LDH), and ALAMAR BLUE™ (resazurin).

DETAILED DESCRIPTION OF THE PREFERRED EMBODIMENTS

I. Definitions

Figure 8:
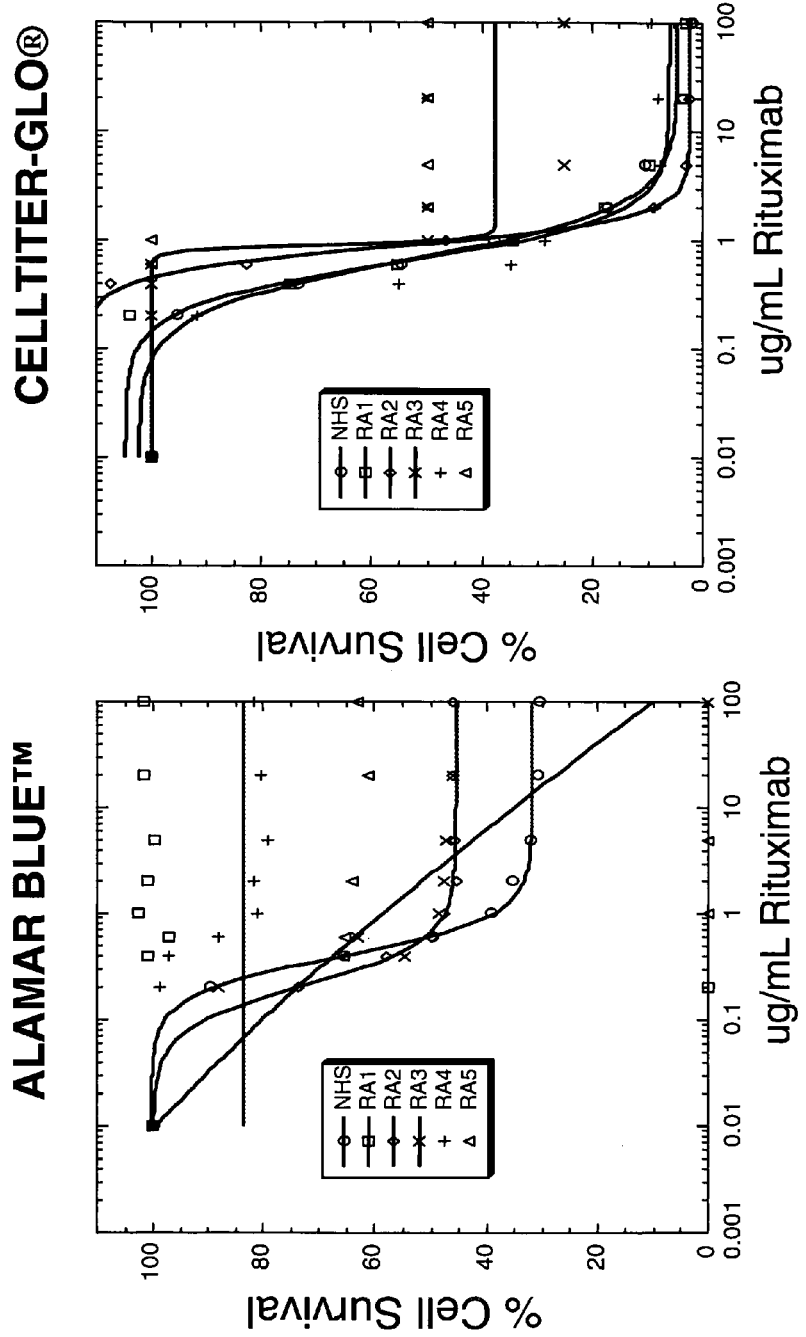
FIG. 8 compares RA serum interference comprising ALAMAR BLUE™ (resazurin) (left) or CELLTITER-GLO® (right) for assay readout.

Unless indicated otherwise, by "biological sample" herein is meant a sample obtained from a human subject. The subject preferably is an autoimmune disease subject. The sample may comprise immunoglobulins from the subject that bind to an antibody or drug with which the patient may have been treated, such as human anti-murine antibody (HAMA), human anti-chimeric antibody (HACA) or human anti-human antibody (HAHA). The biological sample may for example comprise serum, plasma, cell lysate, milk, saliva, vitrous fluid, synovial fluid, peritoneal cavity fluid, lacrimal fluid, tissue homogenate, but preferably serum. The sample may be from a subject who has been treated with a drug (in which case, the sample may further comprise the drug, such as a therapeutic antibody or immunoadhesin), or may be from an untreated or drug naïve subject.

"Autoimmune disease" herein refers to a disease or disorder arising from and directed against an individual's own tissues or organs or a co-segregate or manifestation thereof or resulting condition therefrom. In one embodiment, it refers to a condition that results from, or is aggravated by, the production by B cells of antibodies that are reactive with normal body tissues and antigens. In other embodiments, the autoimmune disease is one that involves secretion of an autoantibody that is specific for an epitope from a self antigen (e.g. a nuclear antigen). Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, antiphospholipid antibody syndrome, allergic neuritis, Behcet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, *ascariasis*, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

A "subject" herein is a human subject.

An "autoimmune disease subject" herein is a subject who has, or is at risk for developing, an autoimmune disease.

By "delipidating" herein is intended removing lipid from a biological sample, such as serum. Delipidation is desirable for removing lipids that may be present in the sample and may block or clog a purification column. Delipidation can be achieved by various methods including use of an absorbent (such as LIPOSORB®; sorbitan esters/polyoxyethylene sorbitan esters), organic extraction, filtration, centrifugation, and the like.

By "affinity purifying" is intended use of an adsorbent, preferably immobilized, which selectively or preferentially binds to a compound or composition (for example Fc region-containing polypeptides) to be purified. Examples include Protein A+G purification; IgG affinity purification (e.g. using MELON GEL™, from Pierce); anti-immunoglobulin antibodies (used singly or in combination with specificity for one or more isotypes; for example, a combination of anti-human IgG, IgA, IgM and IgE, coupled for specific affinity purification of each isotype); any other adsorbant with immunoglobulin binding properties (for example, PIERCE T-GEL™). The preferred affinity purification method herein involves the use of Protein A+G affinity purification (see definition below) to purify IgG, IgA, IgM and IgE antibody isotypes out of a biological sample. Preferably, the affinity purification herein purifies Fc region-containing polypeptides of essentially all isotypes.

An "Fc region-containing polypeptide" herein is a polypeptide which comprises an Fc region. Examples of such polypeptides include therapeutic antibodies, immunoadhesins, and immunoglobulins from subjects (including the subject's anti-drug immunoglobulins).

An "adsorbent" herein is a substance or composition which is able to attach other substances to its surface without any covalent bonding. Preferably, the adsorbent is immobilized.

An "immobilized" adsorbent is one which is affixed to a solid phase.

By "solid phase" is meant a non-aqueous matrix to which an adsorbent can be attached. The solid phase of interest herein is generally one which comprises a glass, silica, agarose or polystyrene surface. The solid phase may, for example, comprise a purification column or a discontinuous phase of discrete particles.

"Protein A+G affinity purification" herein refers to the use Protein A and Protein G, including variants, fragments, and/or fusions thereof, preferably immobilized on a solid phase, to remove immunoglobulins or Fc region-containing polypeptides from a sample. Such purification includes essentially simultaneous Protein A and Protein G purification, as well as sequential purification in any order (i.e. Protein A followed by Protein G, and vice versa).

By "concentrating" herein is meant increasing the concentration of a compound or composition of interest. For example, the concentration of immunoglobulins in a sample can be increased using a concentrator (such as Pierce ICON® protein concentrator, or CENTRICON-30™), centrifugation, filtration, etc.

The expression "biological activity" refers to a measurable function of an agent, such as a therapeutic antibody or immunoadhesin herein. Various activities are contemplated and include, but are not limited to, complement-dependent cytotoxicity (CDC), antibody-dependent cell-mediated cytotoxicity (ADCC), apoptosis, ion channel modulation, inhibiting growth of cells (e.g. cells expressing antigen to which the therapeutic antibody or immunoadhesin can bind), etc.

A "biological activity assay" refers to an assay that evaluates the biological activity of an agent or composition, such as a therapeutic antibody or immunoadhesin.

Herein, a "cell-based" assay is a bioassay that utilizes cells, including cell lines, to evaluate biological activity of an agent or composition, such as a therapeutic antibody or immunoadhesin. Preferably, the cell or cell line used in the assay expresses an antigen to which a therapeutic antibody or immunoadhesin binds.

The ability of a biological sample (including a pretreated sample or purified immunoglobulin preparation) to "block" a biological activity of an antagonist or antibody refers to both partial and complete blocking of that activity.

"Neutralizing antibodies" herein refer to antibodies that not only bind to an antigen (e.g. a therapeutic antibody or immunoadhesin) of interest, but further inhibit, to some extent, a biological activity of that antigen.

Herein, a "neutralizing antibody assay" is an assay which evaluates the presence of neutralizing antibodies in a sample.

"Interference" herein refers to the presence of compound(s) or composition(s) which interfere with the reproducibility of a cell-based biological activity assay, such as a neutralizing antibody assay. The presence of interference in a sample can be confirmed, for example, by assaying serum from drug naive autoimmune subjects from the target population in which the bioassay is to be performed. Where the assay demonstrates highly variable cellular responses between these individuals, one may conclude that serum interference is present in one or more of the samples. Preferably, the interference is not rheumatoid factor (RF), immunoglobulin, or a drug which a subject has been treated with.

A "B-cell" is a lymphocyte that matures within the bone marrow, and includes a naive B cell, memory B cell, or effector B cell (plasma cells). The B-cell herein may be a normal or non-malignant B cell.

A "B-cell surface marker" or "B-cell surface antigen" herein is an antigen expressed on the surface of a B cell that can be targeted with an antagonist or antibody that binds thereto. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, $2^{nd}$ Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a subject and may be expressed on both precursor B cells and mature B cells. Prefered B-cell surface markers for the purposes herein are CD20, CD22, and BR3.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., *Proc. Natl. Acad. Sci.* (USA) 82:1766 (1985), for example.

A "B-cell surface marker antagonist" is a molecule that, upon binding to a B-cell surface marker on B cells, destroys or depletes B cells in a subject and/or interferes with one or more B cell functions, e.g. by reducing or preventing a humoral response elicited by the B cell. The antagonist preferably is able to deplete B cells (i.e. reduce circulating B cell levels) in a subject treated therewith. Such depletion may be achieved via various mechanisms such antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native-sequence peptides, immunoadhesins, and small-molecule antagonists that bind to a B-cell surface marker such as CD20, optionally conjugated with or fused to a cytotoxic agent. The preferred antagonist comprises an antibody.

A "CD20 antibody antagonist" herein is an antibody that, upon binding to CD20 on B cells, destroys or depletes B cells in a subject and/or interferes with one or more B-cell functions, e.g., by reducing or preventing a humoral response elicited by the B cell. The antibody antagonist preferably is able to deplete B cells (i.e., reduce circulating B-cell levels) in a subject treated therewith. Such depletion may be achieved via various mechanisms such antibody-dependent cell-mediated cytotoxicity (ADCC) and/or complement-dependent cytotoxicity (CDC), inhibition of B-cell proliferation and/or induction of B-cell death (e.g., via apoptosis).

As used herein, "B cell depletion" refers to a reduction in B cell levels in an animal or human generally after drug or antibody treatment, as compared to the level before treatment. B cell depletion can be partial or complete. B cell levels are measurable using well known techniques such as those described in Reff et al., Blood 83: 435-445 (1994), or U.S. Pat. No. 5,736,137 (Anderson et al.). By way of example, a mammal (e.g. a normal primate) may be treated with various dosages of the antibody or immunoadhesin, and peripheral B-cell concentrations may be determined, e.g. by a FACS method that counts B cells.

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, U.S. Pat. No. 5,595,721); murine monoclonal antibody "1F5" (Press et al. Blood 69(2):584-591 (1987) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); humanized 2H7 (WO 2004/056312, Lowman et al., and as set forth below); 2F2 (HuMax-CD20), a fully human, high-affinity antibody targeted at the CD20 molecule in the cell membrane of B-cells (Genmab, Denmark; see, for example, Glennie and van de Winkel, Drug Discovery Today 8: 503-510 (2003) and Cragg et al., Blood 101: 1045-1052 (2003); WO 2004/035607; US2004/0167319); the human monoclonal antibodies set forth in WO 2004/035607 and US2004/0167319 (Teeling et al.); the antibodies having complex N-glycoside-linked sugar chains bound to the Fc region described in US 2004/0093621 (Shitara et al.); monoclonal antibodies and antigen-binding fragments binding to CD20 (WO 2005/000901, Tedder et al.) such as HB20-3, HB20-4, HB20-25, and MB20-11; CD20 binding molecules such as the AME series of antibodies, e.g., AME 33 antibodies as set forth in WO 2004/103404 and US2005/0025764 (Watkins et al., Eli Lilly/Applied Molecular Evolution, AME); CD20 binding molecules such as those described in US 2005/0025764 (Watkins et al.); A20 antibody or variants thereof such as chimeric or humanized A20 antibody (cA20, hA20, respectively) or IMMU-106 (US 2003/0219433, Immunomedics); CD20-binding antibodies, including epitope-depleted Leu-16, 1H4, or 2B8, optionally conjugated with IL-2, as in US 2005/0069545A1 and WO 2005/16969 (Carr et al.); bispecific antibody that binds CD22 and CD20, for example, hLL2xhA20 (WO2005/14618, Chang et al.); monoclonal antibodies L27, G28-2, 93-1B3, B-C1 or NU-B2 available from the International Leukocyte Typing Workshop (Valentine et al., In: Leukocyte Typing III (McMichael, Ed., p. 440, Oxford University Press (1987)); 1H4 (Haisma et al. Blood 92:184 (1998)); anti-CD20 auristatin E conjugate (Seattle Genetics); anti-CD20-IL2 (EMD/Biovation/City of Hope); anti-CD20 MAb therapy (EpiCyte); anti-CD20 antibody TRU 015 (Trubion). The preferred CD20 antibodies herein are chimeric, humanized, or human CD20 antibodies, more preferably rituximab, humanized 2H7, 2F2 (Hu-Max-CD20) human CD20 antibody (Genmab), and humanized A20 or IMMUN-106 antibody (Immunomedics).

The terms "rituximab" or "RITUXAN®" herein refer to the genetically engineered chimeric murine/human monoclonal antibody directed against the CD20 antigen and designated "C2B8" in U.S. Pat. No. 5,736,137, including fragments thereof which retain the ability to bind CD20.

Purely for the purposes herein and unless indicated otherwise, a "humanized 2H7" antibody is a humanized variant of murine 2H7 antibody, wherein the antibody is effective to reduce circulating B cells in vivo.

In one embodiment, the humanized 2H7 antibody comprises one, two, three, four, five or six of the following CDR sequences:

CDR L1 sequence RASSSVSYXH wherein X is M or L (SEQ ID NO. 21), for example SEQ ID NO:4 (FIG. 1A),
CDR L2 sequence of SEQ ID NO:5 (FIG. 1A),
CDR L3 sequence QQWXFNPPT wherein X is S or A (SEQ ID NO. 22), for example SEQ ID NO:6 (FIG. 1A),
CDR H1 sequence of SEQ ID NO:10 (FIG. 1B),
CDR H2 sequence of AIYPGNGXTSYNQKFKG wherein X is D or A (SEQ ID NO. 23), for example SEQ ID NO:11 (FIG. 1B), and
CDR H3 sequence of VVYYSXXYWYFDV wherein the X at position 6 is N, A, Y, W or D, and the X as position 7 is S or R (SEQ ID NO. 24), for example SEQ ID NO: 12 (FIG. 1B).

The CDR sequences above are generally present within human variable light and variable heavy framework sequences, such as substantially the human consensus FR residues of human light chain kappa subgroup I ($V_L\kappa I$), and substantially the human consensus FR residues of human heavy chain subgroup III ($V_H III$). See also WO 2004/056312 (Lowman et al.).

The variable heavy region may be joined to a human IgG chain constant region, wherein the region may be, for example, IgG1 or IgG3, including native sequence and variant constant regions.

In a preferred embodiment, such antibody comprises the variable heavy domain sequence of SEQ ID NO:8 (v16, as shown in FIG. 1B), optionally also comprising the variable light domain sequence of SEQ ID NO:2 (v16, as shown in FIG. 1A), which optionally comprises one or more amino acid substitution(s) at positions 56, 100, and/or 100a, e.g. D56A, N100A or N100Y, and/or S100aR in the variable heavy domain and one or more amino acid substitution(s) at positions 32 and/or 92, e.g. M32L and/or S92A, in the variable light domain. Preferably, the antibody is an intact antibody comprising the light chain amino acid sequences of SEQ ID NOs. 13 or 15, and heavy chain amino acid sequences of SEQ ID NO. 14, 16, 17 or 20.

A preferred humanized 2H7 antibody is ocrelizumab (Genentech).

The antibody herein may further comprise at least one amino acid substitution in the Fc region that improves ADCC activity, such as one wherein the amino acid substitutions are at positions 298, 333, and 334, preferably S298A, E333A, and K334A, using Eu numbering of heavy chain residues. See also U.S. Pat. No. 6,737,056B1, Presta.

Any of these antibodies may comprise at least one substitution in the Fc region that improves FcRn binding or serum half-life, for example a substitution at heavy chain position 434, such as N434W. See also U.S. Pat. No. 6,737,056B1, Presta.

Any of these antibodies may further comprise at least one amino acid substitution in the Fc region that increases CDC activity, for example, comprising at least a substitution at position 326, preferably K326A or K326W. See also U.S. Pat. No. 6,528,624B1 (Idusogie et al.).

Some preferred humanized 2H7 variants are those comprising the variable light domain of SEQ ID NO:2 and the variable heavy domain of SEQ ID NO:8, including those with or without substitutions in an Fc region (if present), and those comprising a variable heavy domain with alteration N100A; or D56A and N100A; or D56A, N100Y, and S100aR; in SEQ ID NO:8 and a variable light domain with alteration M32L; or S92A; or M32L and S92A; in SEQ ID NO:2.

M34 in the variable heavy chain of 2H7.v16 has been identified as a potential source of antibody stability and is another potential candidate for substitution.

In a summary of some various preferred embodiments of the invention, the variable region of variants based on 2H7.v16 comprise the amino acid sequences of v16 except at the positions of amino acid substitutions that are indicated in Table 1 below. Unless otherwise indicated, the 2H7 variants will have the same light chain as that of v16.

TABLE 1

Exemplary Humanized 2H7 Antibody Variants

| 2H7 Version | Heavy chain (V$_H$) changes | Light chain (V$_L$) changes | Fc changes |
|---|---|---|---|
| 16 for reference | — | — | |
| 31 | — | — | S298A, E333A, K334A |
| 73 | N100A | M32L | |
| 75 | N100A | M32L | S298A, E333A, K334A |
| 96 | D56A, N100A | S92A | |
| 114 | D56A, N100A | M32L, S92A | S298A, E333A, K334A |
| 115 | D56A, N100A | M32L, S92A | S298A, E333A, K334A, E356D, M358L |
| 116 | D56A, N100A | M32L, S92A | S298A, K334A, K322A |
| 138 | D56A, N100A | M32L, S92A | S298A, E333A, K334A, K326A |
| 477 | D56A, N100A | M32L, S92A | S298A, E333A, K334A, K326A, N434W |
| 375 | — | — | K334L |
| 588 | — | — | S298A, E333A, K334A, K326A |
| 511 | D56A, N100Y, S100aR | M32L, S92A | S298A, E333A, K334A, K326A |

One preferred humanized 2H7 comprises 2H7.v16 variable light domain sequence: DIQMTQSPSSLSASVGDRVTITCRASSSVSYMHWYQQKPGKAPKPLIYAPSNLASGVPSRFSGSGSGTDFTLTISSLQPEDFATYYCQQWSFNPPTFGQGTKVEIKR (SEQ ID NO:2); and 2H7.v16 variable heavy domain sequence:

```
EVQLVESGGGLVQPGGSLRLSCAASGYTFTSYNMHWV  (SEQ ID NO:8)
RQAPGKGLEWVGAIYPGNGDTSYNQKYKGRFTISVDK
SKNTLYLQMNSLRAEDTAVYYCARVVYYSNSYWYFDV
WGQGTLVTVSS.
```

Where the humanized 2H7.v16 antibody is an intact antibody, it may comprise the light chain amino acid sequence:

```
DIQMTQSPSSLSASVGDRVTITCRASSSVSYMHWYQ  (SEQ ID NO:13)
QKPGKAPKPLIYAPSNLASGVPSRFSGSGSGTDFTL
TISSLQPEDFATYYCQQWSFNPPTFGQGTKVEIKRT
VAAPSVFIFPPSDEQLKSGTASVVCLLNNFYPREAK
VQWKVDNALQSGNSQESVTEQDSKDSTYSLSSTLTL
SKADYEKHKVYACEVTHQGLSSPVTKSFNRGEC;
``` and the heavy chain amino acid sequence of SEQ ID NO. 14 or:

```
EVQLVESGGGLVQPGGSLRLSCAASGYTFTSYNMHW  (SEQ ID NO:17)
VRQAPGKGLEWVGAIYPGNGDTSYNQKFKGRFTISV
DKSKNTLYLQMNSLRAEDTAVYYCARVVYYSNSYWY
FDVWGQGTLVTVSSASTKGPSVFPLAPSSKSTSGGT
AALGCLVKDYFPEPVTVSWNSGALTSGVHTFPAVLQ
SSGLYSLSSVVTVPSSSLGTQTYICNVNHKPSNTKV
DKKVEPKSCDKTHTCPPCPAPELLGGPSVFLFPPKP
KDTLMISRTPEVTCVVVDVSHEDPEVKFNWYVDGVE
VHNAKTKPREEQYNSTYRVVSVLTVLHQDWLNGKEY
KCKVSNKALPAPIEKTISKAKGQPREPQVYTLPPSR
EEMTKNQVSLTCLVKGFYPSDIAVEWESNGQPENNY
KTTPPVLDSDGSFFLYSKLTVDKSRWQQGNVFSCSV
MHEALHNHYTQKSLSLSPG.
```

Another preferred humanized 2H7 antibody comprises 2H7.v511 variable light domain sequence:

```
DIQMTQSPSSLSASVGDRVTITCRASSSVSYLHWYQ  (SEQ ID NO:18)
QKPGKAPKPLIYAPSNLASGVPSRFSGSGSGTDFTL
TISSLQPEDFATYYCQQWAFNPPTFGQGTKVEIKR
``` and 2H7.v511 variable heavy domain sequence:

```
EVQLVESGGGLVQPGGSLRLSCAASGYTFTSYNMHW  (SEQ ID NO.19)
VRQAPGKGLEWVGAIYPGNGATSYNQKFKGRFTISV
DKSKNTLYLQMNSLRAEDTAVYYCARVVYYSYRYWY
FDVWGQGTLVTVSS.
```

Where the humanized 2H7.v511 antibody is an intact antibody, it may comprise the light chain amino acid sequence:

```
DIQMTQSPSSLSASVGDRVTITCRASSSVSYLHWYQ  (SEQ ID NO:15)
QKPGKAPKPLIYAPSNLASGVPSRFSGSGSGTDFTL
TISSLQPEDFATYYCQQWAFNPPTFGQGTKVEIKRT
VAAPSVFIFPPSDEQLKSGTASVVCLLNNFYPREAK
VQWKVDNALQSGNSQESVTEQDSKDSTYSLSSTLTL
SKADYEKHKVYACEVTHQGLSSPVTKSFNRGEC
``` and the heavy chain amino acid sequence of SEQ ID NO. 16 or:

```
EVQLVESGGGLVQPGGSLRLSCAASGYTFTSYNMHW  (SEQ ID NO.20)
VRQAPGKGLEWVGAIYPGNGATSYNQKFKGRFTISV
DKSKNTLYLQMNSLRAEDTAVYYCARVVYYSYRYWY
FDVWGQGTLVTVSSASTKGPSVFPLAPSSKSTSGGT
AALGCLVKDYFPEPVTVSWNSGALTSGVHTFPAVLQ
SSGLYSLSSVVTVPSSSLGTQTYICNVNHKPSNTKV
DKKVEPKSCDKTHTCPPCPAPELLGGPSVFLFPPKP
KDTLMISRTPEVTCVVVDVSHEDPEVKFNWYVDGVE
VHNAKTKPREEQYNATYRVVSVLTVLHQDWLNGKEY
KCKVSNAALPAPIAATISKAKGQPREPQVYTLPPSR
EEMTKNQVSLTCLVKGFYPSDIAVEWESNGQPENNY
KTTPPVLDSDGSFFLYSKLTVDKSRWQQGNVFSCSV
MHEALHNHYTQKSLSLSPG.
```

For the purposes herein, "immunotherapy" will refer to a method of treating a mammal (preferably a human patient) with an antibody, wherein the antibody may be an unconjugated or "naked" antibody, or the antibody may be conjugated or fused with heterologous molecule(s) or agent(s), such as one or more cytotoxic agent(s), thereby generating an "immunoconjugate".

As used herein, a "therapeutic antibody" is an antibody that is effective in treating a disease or disorder (preferably an autoimmune disease) in a mammal with or predisposed to the disease or disorder. Exemplary therapeutic antibodies include HER2 antibodies including trastuzumab (HERCEPTIN®) (Carter et al., *Proc. Natl. Acad. Sci. USA*, 89:4285-4289

(1992), U.S. Pat. No. 5,725,856) and pertuzumab (OMNI-TARG™) (WO01/00245); CD20 antibodies (see below); IL-8 antibodies (St John et al., *Chest,* 103:932 (1993), and International Publication No. WO 95/23865); VEGF or VEGF receptor antibodies including humanized and/or affinity matured VEGF antibodies such as the humanized VEGF antibody huA4.6.1 bevacizumab (AVASTIN®) and ranibizumab (LUCENTIS®) (Kim et al., *Growth Factors,* 7:53-64 (1992), International Publication No. WO 96/30046, and WO 98/45331, published Oct. 15, 1998); PSCA antibodies (WO01/40309); CD11a antibodies including efalizumab (RAPTIVA®) (U.S. Pat. No. 5,622,700, WO 98/23761, Steppe et al., *Transplant Intl.* 4:3-7 (1991), and Hourmant et al., *Transplantation* 58:377-380 (1994)); antibodies that bind IgE including omalizumab (XOLAIR®) (Presta et al., *J. Immunol.* 151:2623-2632 (1993), and International Publication No. WO 95/19181;U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); CD18 antibodies (U.S. Pat. No. 5,622,700, issued Apr. 22, 1997, or as in WO 97/26912, published Jul. 31, 1997); Apo-2 receptor antibody antibodies (WO 98/51793 published Nov. 19, 1998); Tissue Factor (TF) antibodies (European Patent No. 0 420 937 B1 granted Nov. 9, 1994); $\alpha_4$-$\alpha_7$ integrin antibodies (WO 98/06248 published Feb. 19, 1998); EGFR antibodies (e.g. chimerized or humanized 225 antibody, cetuximab, ERBUTIX® as in WO 96/40210 published Dec. 19, 1996); CD3 antibodies such as OKT3 (U.S. Pat. No. 4,515,893 issued May 7, 1985); CD25 or Tac antibodies such as CHI-621 (SIMULECT®) and ZENAPAX® (See U.S. Pat. No. 5,693,762 issued Dec. 2, 1997); CD4 antibodies such as the cM-7412 antibody (Choy et al. *Arthritis Rheum* 39(1):52-56 (1996)); CD52 antibodies such as CAMPATH-1H (ILEX/Berlex) (Riechmann et al. *Nature* 332:323-337 (1988)); Fc receptor antibodies such as the M22 antibody directed against FcγRI as in Graziano et al. *J. Immunol.* 155(10):4996-5002 (1995); carcinoembryonic antigen (CEA) antibodies such as hMN-14 (Sharkey et al. *Cancer Res.* 55(23Suppl): 5935s-5945s (1995)); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); CD38 antibodies, e.g. AT 13/5 (Ellis et al. *J. Immunol.* 155(2):925-937 (1995)); CD33 antibodies such as Hu M195 (Jurcic et al. *Cancer Res* 55(23 Suppl):5908s-5910s (1995)) and CMA-676 or CDP771; EpCAM antibodies such as 17-1A (PANOREX®); GpIIb/IIIa antibodies such as abciximab or c7E3 Fab (REOPRO®); RSV antibodies such as MEDI-493 (SYNAGIS®); CMV antibodies such as PROTOVIR®; HIV antibodies such as PRO542; hepatitis antibodies such as the Hep B antibody OSTAVIR®; CA 125 antibody OvaRex; idiotypic GD3 epitope antibody BEC2; αvβ3 antibody (e.g. VITAXIN®; Medimmune); human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); human leukocyte antigen (HLA) antibody such as Smart ID10 and the anti-HLA DR antibody Oncolym (Lym-1); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody, such as Lym-1Y-90 (USC) or anti-Lym-1 Oncolym (USC/Peregrine); LIF 226 (Enhanced Lifesci.); BAFF antibody (e.g., WO 03/33658); BAFF receptor antibody (e.g., WO 02/24909); BR3 antibody; Blys antibody such as belimumab; LYMPHOSTAT-B™; ISF 154 (UCSD/Roche/Tragen); gomilixima (Idec 152; Biogen Idec); IL-6 receptor antibody such as atlizumab (ACTEMRA™; Chugai/Roche); IL-15 antibody such as HuMax-Il-15 (Genmab/Amgen); chemokine receptor antibody, such as a CCR2 antibody (e.g. MLN1202; Millieneum); anti-complement antibody, such as C5 antibody (e.g. eculizumab, 5G1.1; Alexion); oral formulation of human immunoglobulin (e.g. IgPO; Protein Therapeutics); IL-12 antibody such as ABT-874 (CAT/Abbott); Teneliximab (BMS-224818; BMS); CD40 antibodies, including S2C6 and humanized variants thereof (WO00/75348) and TNX 100 (Chiron/Tanox); TNF-α antibodies including cA2 or infliximab (REMICADE®), CDP571, MAK-195, adalimumab (HUMIRA™), pegylated TNF-α antibody fragment such as CDP-870 (Celltech), D2E7 (Knoll), anti-TNF-α polyclonal antibody (e.g. PassTNF; Verigen); CD22 antibodies such as LL2 or epratuzumab (LYMPHOCIDE®; Immunomedics), including epratuzumab Y-90 and epratzumab I-131, Abiogen's CD22 antibody (Abiogen, Italy), CMC 544 (Wyeth/Celltech), combotox (UT Soutwestern), BL22 (NIH), and LympoScan Tc99 (Immunomedics). Preferably, the therapeutic antibody herein is a naked, intact antibody useful in the treatment of autoimmune disease, such as RA and/or SLE.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous"), and an immunoglobulin constant domain sequence (e.g., CH2 and/or CH3 sequence of an IgG). Exemplary adhesin sequences include contiguous amino acid sequences that comprise a portion of a receptor (herein a "ligand binding domain") or a ligand (herein a "receptor binding domain") that binds to a protein of interest. Adhesin sequences also include sequences that bind a protein of interest, but are not receptor or ligand sequences (e.g., adhesin sequences in peptibodies). Such polypeptide sequences can be selected or identified by various methods, include phage display techniques and high throughput sorting methods.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule that combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

"Treatment" of a subject herein refers to both therapeutic treatment and prophylactic or preventative measures. Those in need of treatment include those already with the disease as well as those in which the disease is to be prevented. Hence, the subject may have been diagnosed as having the disease or may be predisposed or susceptible to the disease. The term "treating", "treat" or "treatment" as used herein includes preventative (e.g., prophylactic), palliative and curative treatment.

The expression "effective amount" refers to an amount of a drug (such as an antibody or immunoadhesin) that is effective for preventing, ameliorating or treating the disease. Such an effective amount will generally result in an improvement in the signs or symptoms of disease.

The term "immunosuppressive agent" as used herein for adjunct therapy refers to substances that act to suppress or mask the immune system of the subject being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporine; 6 mercaptopurine; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251: 430-432 (1991); WO 90/11294; Ianeway, Nature, 341:482 (1989); and WO 91/01133); BAFF antagonists such as BAFF or BR3 antibodies or immunoadhesins and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9.

As used herein, "BAFF antagonist" generally refers to any compound that directly inhibits the biological activity of BAFF. A molecule directly inhibits the biological activity of BAFF by interacting with a BAFF polypeptide, BAFF gene, a BAFF transcript, or a BAFF receptor. A BAFF antagonist may, for example, bind to and neutralize the activity of BAFF; decrease BAFF expression levels; affect stability of BAFF; affect proteolytic cleavage of the membrane bound form of BAFF into the soluble form; interfere with the binding of BAFF to one or more receptors; or it may interfere with intracellular signaling of one or more BAFF receptors. BAFF antagonists may be proteinaceous (e.g., antibodies, receptor fusion proteins, peptides, peptibodies, dominant negative BAFF mutants) or non proteinaceous molecules (e.g., small organic molecules (less than about 500 Da)), including siRNA and aptamers, etc. Methods for assessing neutralizing biological activity of BAFF antagonists include, those are known described in the art. Examples of BAFF antagonists include polypeptides comprising a BAFF-binding portion of a BAFF receptor or a BAFF-binding variant thereof (e.g., WO 01/12812, WO 02/24909, WO 00/40716, WO 03/024991), anti-BAFF antibodies (e.g., WO 03/33658), BAFF-binding peptibody (e.g., WO 02/092620), anti-BAFF-R antibodies (e.g., WO 02/24909) and BAFF-binding peptides (e.g., WO 02/16412). According to one embodiment, the BAFF antagonist is selected from the group consisting of BCMA-Fc (e.g., WO 01/12812), BAFF-R-Fc (e.g., WO 02/24909), TACI-Ig (e.g., WO 00/40716), an anti-BAFF antibody (e.g., WO 03/33658), an anti-BAFF-R antibody (e.g., WO 02/24909), a BAFF-binding peptibodies (e.g., WO02/092620), a dominant negative BAFF (e.g., WO 04/081043). According a further embodiment, anti-BAFF antibodies and anti-BAFF receptor antibodies are human, humanized, chimerized or otherwise enhanced for treatment in humans.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small-molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrozole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

As used herein, the term "EGFR inhibitor" refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA™) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boebringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3 fluorophenyl) methoxy]phenyl]6[5 [[[2methylsulfonyl)ethyl]amino]methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC™) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF) or its receptor, such as bevacizumab (AVASTIN®) or ranibizumab (LUCENTIS®), or αvβ3 antibody such as VITAXN™ (Medimmune).

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-112, IL-15, including PROLEUKIN® rIL-2 and human IL-4 and mutants of human IL-4, such as, for example, a mutant containing a mutation in the region of IL-4 which is involved in binding to IL-2R gamma, e.g., Arg 21 is changed to a Glu residue; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; hormone-replacement therapy; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

The term "growth factor" refers to proteins that promote growth, and include, for example, hepatic growth factor; fibroblast growth factor; vascular endothelial growth factor;

nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, -β, and -γ; and colony stimulating factors (CSFs) such as macrophage-CSF (M-CSF); granulocyte-macrophage-CSF (GM-CSF); and granulocyte-CSF (G-CSF). As used herein, the term growth factor includes proteins from natural sources or from recombinant cell culture and biologically active equivalents of the native-sequence growth factor, including synthetically produced small-molecule entities and pharmaceutically acceptable derivatives and salts thereof.

The term "integrin" refers to a receptor protein that allows cells both to bind to and to respond to the extracellular matrix and is involved in a variety of cellular functions such as wound healing, cell differentiation, homing of tumor cells and apoptosis. They are part of a large family of cell adhesion receptors that are involved in cell-extracellular matrix and cell-cell interactions. Functional integrins consist of two transmembrane glycoprotein subunits, called alpha and beta, that are non-covalently bound. The alpha subunits all share some homology to each other, as do the beta subunits. The receptors always contain one alpha chain and one beta chain. Examples include Alpha6beta1, Alpha3beta1, Alpha7beta1, LFA-1 etc. As used herein, the term "integrin" includes proteins from natural sources or from recombinant cell culture and biologically active equivalents of the native-sequence integrin, including synthetically produced small-molecule entities and pharmaceutically acceptable derivatives and salts thereof.

For the purposes herein, "tumor necrosis factor alpha (TNF-alpha)" refers to a human TNF-alpha molecule comprising the amino acid sequence as described in Pennica et al., Nature, 312:721 (1984) or Aggarwal et al., JBC, 260:2345 (1985).

A "TNF-alpha inhibitor" herein is an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), adalimumab (HUMIRA™), pegylated soluble TNF-R pegsunercept (sTNF-R1; Amgen); pegylated anti-TNF antibody fragment, CDP-870 (Celltech).

Examples of "disease-modifying anti-rheumatic drugs" or "DMARDs" include hydroxycloroquine, sulfasalazine, methotrexate, leflunomide, etanercept, infliximab (plus oral and subcutaneous methotrexate), azathioprine, D-penicillamine, gold salts (oral), gold salts (intramuscular), minocycline, cyclosporine including cyclosporine A and topical cyclosporine, staphylococcal protein A (Goodyear and Silverman, J. Exp. Med., 197, (9), p1125-39 (2003)), including salts and derivatives thereof, etc.

Examples of "non-steroidal anti-inflammatory drugs" or "NSAIDs" include aspirin, acetylsalicylic acid, ibuprofen, naproxen, indomethacin, sulindac, tolmetin, COX-2 inhibitors such as celecoxib (CELEBREX®; 4-(5-(4-methylphenyl)-3-(trifluoromethyl)-1H-pyrazol-1-yl)benzenesulfonamide and valdecoxib (BEXTRA®), and meloxicam (MOBIC®), including salts and derivatives thereof, etc. Preferably, they are aspirin, naproxen, ibuprofen, indomethacin, or tolmetin.

Examples of "integrin antagonists or antibodies" herein include a CD11a or LFA-1 antibody, such as efalizumab (RAPTIVA®) commercially available from Genentech, or an alpha 4 integrin antibody such as natalizumab (ANTEGREN®) available from Biogen Idec/Elan, or diazacyclic phenylalanine derivatives (WO 2003/89410), phenylalanine derivatives (WO 2003/70709, WO 2002/28830, WO 2002/16329 and WO 2003/53926), phenylpropionic acid derivatives (WO 2003/10135), enamine derivatives (WO 2001/79173), propanoic acid derivatives (WO 2000/37444), alkanoic acid derivatives (WO 2000/32575), substituted phenyl derivatives (U.S. Pat. Nos. 6,677,339 and 6,348,463), aromatic amine derivatives (U.S. Pat. No. 6,369,229), ADAM disintegrin domain polypeptides (US2002/0042368), antibodies to alphavbeta3 integrin (EP 633945), aza-bridged bicyclic amino acid derivatives (WO 2002/02556), and 683699 (Tanabe) etc.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone, such as SOLU-MEDROL® methylprednisolone sodium succinate), dexamethasone or dexamethasone triamcinolone, hydrocortisone, and betamethasone. The preferred corticosteroids herein are prednisone, methylprednisolone, hydrocortisone, or dexamethasone.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

An "intact antibody" herein is one which comprises two antigen binding regions, and an Fc region. Optionally, the intact antibody has a functional Fc region.

"Growth inhibitory" antibodies are those that prevent or reduce proliferation of a cell expressing an antigen to which the antibody binds. For example, the antibody may prevent or reduce proliferation of B cells in vitro and/or in vivo.

Antibodies that "induce apoptosis" are those that induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies). "Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their "heavy chains," (if present) antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region; as well as naturally occurring variants of any of the above.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Antibody-dependent cell-mediated cytotoxicity" and "ADCC" refer to a cell-mediated reaction in which nonspecific cytotoxic cells that express Fc receptors (FcR5) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγR11 and FcγRIII. FcR expression on hematopoietic cells in summarized is Table 3 on page 464 of Ravetch and Kinet, *Annu. Rev. Immunol.* 9:457-492 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Human effector cells" are leukocytes that express one or more FcR5 and perform effector functions. Preferably, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII , and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-492 (1991); Capel et al., *Immunomethods* 4:25-34 (1994); and de Haas et al., *J. Lab. Clin. Med.* 126:330-341 (1995). Other FcRs, including those to be identified in the future, are encompassed by the term "FcR" herein. The term also includes the neonatal receptor, FcRn, which is responsible for the transfer of maternal IgGs to the fetus and immunoglobulin homeostasis (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816, 567), phage display technologies (see, e.g., Clackson et al., *Nature*, 352:624-628 (1991); Marks et al., *J. Mol. Biol.,* 222: 581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/ 34096; WO 1996/33735; WO 1991/10741; Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); and Lonberg and Huszar, *Intern. Rev. Immunol.,* 13: 65-93 (1995).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

A "naked antibody" for the purposes herein is an antibody that is not conjugated to a cytotoxic moiety or radiolabel.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

"Antibody exposure" refers to contact with or exposure to the antibody herein in one or more doses administered over a period of time of about 1-20 days. The doses may be given at one time or at fixed or irregular time intervals over this period of exposure. Initial and later (e.g. second or third) antibody exposures are separated in time from each other as described in detail herein.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

II. Sample Pretreatment

It was discovered in the Example below that serum from subjects with autoimmune disease, such as RA or SLE, contains substance(s) which interfere(s) with the reproducibility of a cell-based bioassay, such as a neutralizing antibody assay. The interference was not rheumatoid factor (RF) or immunoglobulin.

Various methods were evaluated for addressing this problem, but were not particularly successful either in recovery or specific antibodies, or in eliminating assay interference. While increasing sample dilution minimized interference, the sensitivity of the assay was compromised to greatly. Other methods for addressing the problem of interference were evaluated. For example, changing the assay read-out or cell-based binding assay did not fix the problem, neither did pre-treating the sample by desalting, delipidation, cytokine correlation, or saturated ammonium sulfate precipitation.

Immunoglobulin affinity purification was ultimately identified as the preferred method for removing the interference. This step recovered the subject's immunoglobulins away from the interference, so that the purified immunoglobulins could be subjected more reliably to a cell-based bioassay.

Accordingly, the invention concerns a method of treating a biological sample from an autoimmune disease subject comprising:

(a) delipidating the sample;

(b) affinity purifying immunoglobulins in the sample;

(c) concentrating the purified immunoglobulins; and (d) subjecting the concentrated immunoglobulins to a cell-based biological activity assay (preferably a neutralizing antibody assay).

Steps (a), (b) and (c) can be performed in any order, but preferably are carried out as step (a), followed by step (b), followed by step (c).

The biological sample herein includes various samples including serum, plasma, cell lysate, milk, saliva, vitrous fluid, and other secretions, synovial fluid, peritoneal cavity fluid, lacrimal fluid, and tissue homogenate, but preferably the sample comprises a serum sample. Moreover, the sample can be in various forms including liquid, frozen, chilled, lyophilized etc. The sample may be subjected to additional purification or treatment steps prior to and/or following the affinity purification step herein.

The biological sample may comprise immunoglobulins from the subject that bind to the antibody or immunoadhesin with which the patient has been treated, such as human anti-murine antibody (HAMA), human anti-chimeric antibody (HACA) or human anti-human antibody (HAHA). HAHA may be against either a humanized or human therapeutic antibody. In one embodiment, the sample is one which has been determined to contain such antibodies. For instance, serum from the patient may be found to comprise antibodies to the drug in question through an ELISA assay, such as the ELISA assays described in US Patent Application No. 2005/0032130A1 (Beresini and Song) or US Patent Application No. 2003/0068664 (Albitar et al.).

The sample is from a subject with an autoimmune disease, such as those listed above, but preferably rheumatoid arthritis (RA), systemic lupus erythematosis (SLE), or Sjogren's disease, and most preferably RA.

Moreover, the subject from whom the sample is obtained may be, or have been, treated with a therapeutic antibody, immunoadhesin, or other biologic drug such as a pegylated soluble TNF-R (including sTNF-R1 pegsunercept, Amgen), IL-1 receptor antagonist (IL-1Ra) such as anakira (KINERET®), DN-BAFF (Xencor), or vaccine such as B cell lymphoma vaccine (including those available from CRV/ATROS, Intracel, Large Scale Biology, Favrille, NCI, Genitope, etc) or LeukoVAX (Inflammatics).

Where the subject has been treated with a therapeutic antibody, the antibody may bind a B-cell surface marker, such as CD20 antibody, exemplary such antibodies including rituximab, humanized 2H7, 2F2 (HuMax-CD20) human CD20 antibody (Genmab), humanized A20 antibody or IMMU-106 (Immunomedics), TRU 015 (Trubion) etc. The preferred CD20 antibody herein is rituximab or humanized 2H7.

Other therapeutic antibodies of interest include a tumor necrosis factor (TNF)-α antibody (such as infliximab (REMICADE®), CDP571, MAK-195, adalimumab (HUMIRA™), pegylated TNF-α antibody fragment such as CDP-870, anti-TNF-α polyclonal antibody such as PassTNF); integrin antibody (such as efalizumab or natalizumab); BAFF antibody (e.g, WO 03/33658); BR3 antibody; BAFF receptor antibody (e.g., WO02/24909); Blys antibody (such as LYMPHOSTAT-B™, belimumab; HGS/CAT); CD37 antibody (such as TRU 016; Trubion); CD22 antibody such as LL2 or epratuzumab (LYMPHOCIDE®; Immunomedics), Abiogen's CD22 antibody, CMC 544 (Wyeth/Celltech), combotox (UT Soutwestern), BL22 (NIH), LIF 226 (Enhanced Lifesci.); VEGF or VEGF receptor antibody, including bevacizumab (AVASTIN®) and ranibizumab (LUCENTIS®); anti-HER antibody, including trastuzumab (HERCEPTIN®), pertuzumab (OMNITARG™), and cetuximab (ERBUTIX®); anti-IgE antibody, including omalizumab (XOLAIR®); IL-21 antibody (Zymogenetics/Novo Nordisk); anti-B cell antibody (Impheron); B cell targeting MAb (Immunogen/Aventis); 1D09C3 (Morphosys/GPC); Lym-1 antibody such as anti-Lym-1 Oncolym (USC/Peregrine); ISF 154 (UCSD/Roche/Tragen); gomiliximab (Idec 152; Biogen Idec); IL-6 receptor antibody such as atlizumab (ACTEMRA™; Chugai/Roche); IL-15 antibody such as HuMax-Il-15 (Genmab/Amgen); chemokine receptor antibody, such as a CCR2 antibody (e.g. MLN1202; Millieneum); anti-complement antibody, such as C5 antibody (e.g. eculizumab, 5G1.1; Alexion); oral formulation of human immunoglobulin (e.g. IgPO; Protein Therapeutics); IL-12 antibody such as ABT-874 (CAT/Abbott); Teneliximab (BMS-224818; BMS); CD40 antibodY, including S2C6 and humanized variants thereof (WO00/75348) and TNX 100 (Chiron/Tanox); CD52 antibody (e.g. Campath); αvβ3 antibody (VITAXIN®; Medimmune) etc.

Where the autoimmune disease subject has been treated with an immunoadhesin, the immunoadhesin may be BR3-Ig; TNF-α immunoadhesin (for example, etanercept); anti-BAFF peptibody (e.g., WO 02/092620; Amgen); TACI-Ig (Zymogenetics) (e.g, WO 00/40716); BCMA-Ig (ZymoGenetics) (e.g. WO01/12812); CTLA4-Ig, a B7 and CD28 costimulation blocker, such as abatacept (BMS); BAFF-R-Fc (e.g., WO 02/24909); etc.

The biological sample is generally obtained from the patient prior to and/or after the patient has been treated with the drug, antibody or immunoadhesin. Usually biological samples are obtained from the patient at a series of timepoints, e.g. from pretreatment throughout the treatment cycle(s). In order to avoid drug interfering with the performance of the assay, a biological sample will normally be taken when drug washout occurs. For instance, sample at baseline, and at 3, 6 and 9 months may be tested. If the patient is retreated at a later date, sample from baseline and at 3 or 6 months may be pretreated and then tested for neutralizing antibody.

A delipidation step prior to affinity purification is desirable to reduce clogging during the affinity purification step. One can use a lipid absorbent such as (LIPOSORB®; sorbitan esters/polyoxyethylene sorbitan esters) for delipidation, but other methods such as organic extraction, filtration, centrifugation etc, are available for delipidating the sample.

The affinity purification step preferably comprises purifying substantially all immunoglobulin isotypes (namely human IgG1, IgG2, IgG3, IgG4, IgM, IgA, and IgE, even if the affinity of the chosen adsorbent is different for the different isotypes). Affinity purification can be achieved by Protein A chromatography, Protein G chromatography, Protein A+G chromatography (for example, Protein A/G chromatography as exemplified, or a mixture of Protein A and Protein G resins, etc), IgG affinity purification (e.g. using MELON GEL™, from Pierce), anti-immunoglobulin antibody affinity purification (where the anti-immunoglobulin antibodies are used singly or in combination with specificity for one or all isotypes; for example, a combination of anti-human IgG, IgA, IgM and IgE, coupled for specific affinity purification of each isotype), other adsorbant with immunoglobulin binding properties (for example, PIERCE T-GEL™), etc. Preferably, affinity purification comprises Protein A+G affinity purification.

The affinity purification (e.g. Protein A+G affinity purification) is preferably repeated two, three, four, or more times, most preferably three times. After loading the affinity column, the solid phase is preferably washed to remove nonspecific binding, and the immunoglobulins can be eluted using various elution buffers. The preferred elution buffer is compatible with a subsequent cell-based neutralizing antibody assay. For example, the elution buffer can be at low pH, and/or contain hydrochloric acid (HCl), glycine, trifluoroacetic acid (TFA), acetic acid, etc. The elution buffer is optionally neutralized with a basic buffer, and/or phosphate buffered saline (PBS) may be added prior to performing a neutralizing antibody assay.

In one embodiment, the purified immunoglobulins are subjected to additional purification, treatment of concentration steps. For example, the immunoglobulins may be concentrated, for example, using a concentrator, or precipitated and resuspended, or lyophilized, etc.

The sample comprising concentrated or purified immunoglobulins is then able to be subjected to a neutralizing antibody assay, such as the ones described in the following section. The sample may comprise purified Fc-containing polypeptides, such as subject's immunoglobulins (including autoantibodies, and anti-drug antibodies), therapeutic antibodies and immunoadhesins, and rheumatoid factor (RF).

While a neutralizing antibody assay is the preferred cell-based bioassay herein, the pretreated sample may be subjected to other cell-based biological assays, including by way of example, a pharmakodynamic (PD) biomarker assay which can measure the functional activity of a drug in patient serum on cells, etc.

III. Neutralizing Antibody Assay

The sample pretreatment method herein is preferably employed in conjunction with an assay for detecting neutralizing antibodies to drug, such as a therapeutic antibody or immunoadhesin or other biologic, or to an antagonist or antibody that binds to a B cell surface marker (e.g. to an antibody that binds CD20). The assay determines the ability of a biological sample from a patient treated with the therapeutic antibody, immunoadhesin or other drug to block a biological activity of the drug; where blocking activity may indicate reduced efficacy of the drug.

Neutralizing antibodies may decrease the expected pharmacologic level of the infused drug, thereby decreasing efficacy or making the likelihood of response more variable. Neutralizing antibodies can be associated with serum sickness or immune complex disease on retreatment. By way of example, where a neutralizing antibody response is seen, the treatment may be halted or postponed, or the dosage may be increased, or the patient may be given further agents which improve the efficacy of the drug, and/or which reduce any immune response thereto. Various immunosuppressive agents that can be combined with the treatment to reduce an immune response, where a neutralizing antibody response is observed, are known and exemplary such drugs are specifically noted herein.

In addition to the usage of the assay results by clinicians in the treatment of patients, the neutralizing property of anti-drug antibodies, in conjunction with HAMA, HACA, or HAHA data, demonstrate immunogenicity, or tendency of immunogenicity, as well as the nature of immunogenicity of a drug. This information is useful in evaluating drug safety and predicting potential immune responses of patients to therapies.

In the context of a CD20 antibody, or other antagonist that binds a B cell surface marker, the assay is thought to be particularly useful where treatment therewith only leads to partial B cell depletion, where B cell hyperactivation is occurring (e.g. as in SLE), or where persistent disease symptoms exist for years and years (e.g as in SLE and RA).

Use of the assay with respect to patients who are being treated with the drug to treat an autoimmune disease is especially desirable. Various autoimmune diseases are described herein, but exemplary ones includes rheumatoid arthritis (RA), systemic lupus erythematosus (SLE), Wegener's disease, inflammatory bowel disease (IBD), idiopathic or immune thrombocytopenic purpura (ITP), thrombotic thrombocytopenic purpura (TTP), autoimmune thrombocytopenia, multiple sclerosis (MS), psoriasis, IgA nephropathy, IgM polyneuropathies, myasthenia gravis, vasculitis, diabetes mellitus, Reynaud's syndrome, Sjogren's syndrome glomerulonephritis, autoimmune hemolytic anemia etc.

In the preferred embodiment of the invention, the biological activity assay comprises a cell-based biological assay, such as an assay which determines complement-dependent cytotoxicity (CDC), antibody-dependent cell-mediated cytotoxicity (ADCC), apoptosis, ion channel modulation, or inhibition of cell growth.

Preferably, the assay studies CDC activity. According to this embodiment of the invention, cells expressing the antigen (e.g. a B cell surface marker, such as CD20) to which the therapeutic antibody or immunoadhesin binds may be exposed to complement (preferably human complement) in the presence (or absence) of the drug as well as a biological sample from a patient treated with the drug. The present application contemplates exposing the four components (cells, complement, drug and biological sample) simultaneously or sequentially in any order; all of these possibilities are encompassed herein. However, according to the preferred embodiment of the invention, the biological sample (e.g. serum) is combined with the drug so as to allow for neutralization of the drug's activity, and then cells and complement are added to this mixture.

Complement-dependent cytotoxicity (CDC) as a Rituximab neutralizing antibody assay is depicted in FIG. 4. The Fab domain of Rituximab binds to CD20, a cell surface antigen on B lymphocytes. Once bound, the Fc domain of Rituximab will recruit complement, and mediate cell lysis. In vitro, the Rituximab is added along with normal human serum complement, to WIL2-S cells. Cell lysis is measured proportional to the mitochondrial metabolic activity of live cells using either ALAMAR BLUE™ or CELLTITER GLO® (upper panel). When using this CDC assay to assess Rituximab neutralization antibodies in patient serum, the Rituximab is pre-incubated with the patient antibodies, before introducing complement and cells (lower panel). A neutralizing antibody will decrease Rituximab's potency, resulting in greater numbers of metabolically active live cells. The amount of neutralizing activity in a patient's serum is measured proportional to an increase in ALAMAR BLUE™ or CELLTITER GLO® signals relative to a negative control.

Following the exposure step, CDC activity is determined, preferably by assessing cell viability (i.e. by quantifying live cells). Various methods are available for determining cell viability including determining loss of membrane integrity as evaluated by uptake of propidium iodide (PI), trypan blue (see Moore et al. *Cytotechnology* 17:1-11 (1995)), annexin V, or 7AAD relative to untreated cells, the ALAMAR BLUE™ (resazurin) assay as in US Patent Application No. 2005/0032130A1 (Beresini and Song), or a modified assay using CELLTITER-GLO® Luminescent Cell Viability Assay for the assay readout as described below etc. A reduction in the antibody's or immunoadhesin's ability to mediate CDC may indicate that neutralizing antibodies are present in the biological sample.

For a cell-based assay, one will generally use a cell line which expresses the antigen to which the antibody or immunoadhesin binds. In the case of the CD20 antigen, various cells are available including, WIL2-S cells (ATCC CRL 8885, American Type Culture Collection) or WIL2-NS (ATCC CRL-8155), SU-DHL-4 (DSMZ No. ACC495, Deutsche Sammlung Von Mikroorganismen und Zelkulturen), or a CD20 expressing lymphoblastoid B-cell line. CDC assays using CD20 positive cells have been described in Idusogie et al., *J. Immunol.* 164:4178-4184 (2000); Idusogie et al., *J. Immunol.* 166:2571-2575 (2001); Reff et al. *Blood* 83(2):

435-445 (1994); U.S. Pat. No. 6,194,551 B1 (Idusogie et al.); and U.S. Pat. No. 5,736,137 (Anderson et al.).

Where the assay evaluates ADCC, the antibody or immunoadhesin may be assayed for its ability to mediate Natural-Killer cell (NK cell) and/or peripheral blood mononuclear cell (PBMC) lysis of cells expressing the antigen to which the therapeutic antibody binds. In the case of the CD20 antigen, WIL2-S cells may be used, and Shields et al., *J. Biol. Chem.* 276:6591-6604 (2001) and WO00/42072 (Presta, L.) describe an exemplary ADCC assay using those cells. See, also, Clynes et al. *Nature Medicine* 6:443-6 (2000). U.S. Pat. No. 5,736,137 (Anderson et al.) also describes an ADCC assay using CD20 positive cells.

Apoptosis refers to programmed cell death, e.g. of a B cell, and may be determined by a variety of different assays, such as binding of annexin V, fragmentation of DNA, cell shrinkage, dilation of endoplasmic reticulum, cell fragmentation, and/or formation of membrane vesicles (called apoptotic bodies). Assays which determine the ability of an antibody (e.g. Rituximab) to induce apoptosis have been described in Shan et al. *Cancer Immunol Immunther* 48:673-83 (2000); Pedersen et al. *Blood* 99:1314-9 (2002); Demidem et al. *Cancer Chemotherapy & Radiopharmaceuticals* 12(3):177-186 (1997), for example.

The ability of antibody or immunoadhesin to inhibit growth of a cell, e.g. a cancerous B cell expressing the antigen to which the antagonist or antibody binds, can be assessed by a variety of different assays. Taji et al. *Jpn J. Cancer Res* 89:748-56 (1998) describe how to determine growth inhibition of CD20-positive B lymphoma cell lines by a CD20 antibody.

Using the neutralizing antibody assay herein, one may determine the efficacy of an drug (e.g. one which binds CD20), by measuring the ability of a biological sample from a patient treated with the drug to block a biological activity thereof, wherein a reduction in the biological activity relative to a control sample is indicative that the patient is raising antibodies against the drug in question and/or that such antibodies can neutralize, at least to some degree, the biological activity thereof. A significant response may be one which results in a safety related problem from neutralizing antibody development and/or the requirement to alter dosing of the primary drug in response to altered clearance of the drug. For instance, in comparison to the same amount of pre-treatment counterpart (e.g., HAMA, HACA, and HAHA negative), a sample neutralizing about 20% or greater activity of the drug (e.g. in the range from about 20% to about 100%) at a given concentration, may be considered positive for neutralizing antibody directed against the drug.

The preferred neutralizing antibody assay herein is based on that disclosed in US2005/0032130 A1 (Beresini and Song), published Feb. 10, 2005, but modified in various respects as described in more detail in Example 1 below. In particular, the biological sample (i.e. serum) is now pre-treated serum; CELLTITER-GLO® Luminescent Cell Viability Assay is now the assay readout instead of ALAMAR BLUE™ (resazurin); control antibody used is a cynomolgus monkey Protein A purified (HER2 adsorbed) preparation, not goat anti-Rituximab; and buffers, volumes, complement, controls, serum matrix effects, data analysis and interpretation have changed as described in Example 1.

IV. Production of Antibodies

The drug of interest herein may be a therapeutic antibody, e.g. one that binds to a B-cell surface marker, especially one that binds to CD20. Accordingly, methods for generating antibodies will be described here.

The antigen to be used for production of, or screening for, antibodies may be, e.g., a soluble form of the antigen or a portion thereof, containing the desired epitope. Alternatively, or additionally, cells expressing the antigen at their cell surface can be used to generate, or screen for, antibodies. Other forms of the antigen useful for generating antibodies will be apparent to those skilled in the art.

A description follows as to exemplary techniques for the production of antibodies used in accordance with the present invention.

(i) Polyclonal Antibodies

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, antibodies or antibody fragments can be isolated from antibody phage libraries generated using the techniques described in McCafferty et al., *Nature*, 348: 552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind the B cell surface marker and further bind a second different B-cell surface marker. Alternatively, an anti-B cell surface marker binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell surface marker-binding arm and an arm that binds the cytotoxic agent (e.g. saporin, anti-interferon-$\alpha_i$ vinca alkaloid, ricin A chain, methotrexate or radioactive isotope hapten). Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

V. Production of Immunoadhesins

The drug herein may, in another embodiment, be an immunoadhesin, for example a BR3-Ig or TNF-α immunoadhesin. Exemplary methods for making immunoadhesins are described in more detail below.

The simplest and most straightforward immunoadhesin design combines the binding domain(s) of the adhesin (e.g. the extracellular domain (ECD) of a receptor) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc region of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)

(d) $AC_L-V_HC_H-(AC_H,$ or $AC_L-V_HC_H,$ or $V_LC_L-AC_H)$;

(e) $V_LC_L-AC_H-(AC_L-V_HC_H,$ or $V_LC_L-AC_H)$; and (f) $(A-Y)_n-(V_LC_L-V_HC_H)_2$, wherein each A represents identical or different adhesin amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

Immunoadhesins herein include peptibodies, which can be made as described in WO 02/092620, for example.

Other publications describing immunoadhesins of interest include: WO 01/12812 describing BCMA-Fc; WO 02/24909 related to BAFF-R-Fc; WO 00/40716 concerning TACI-Ig, etc.

VI. Conjugates and Other Modifications of the Antibody or Immunoadhesin

The antibody or immunoadhesin herein is optionally conjugated to another agent, such as a cytotoxic agent, or cytokine (for example IL2; see for example, WO2005/016969).

Conjugation will ordinarily be achieved through a covalent linkage, the precise nature of which will be determined by the targeting molecule and the linking site on the CD20 antagonist or antibody polypeptide. Typically, a non-peptidic agent is modified by the addition of a linker that allows conjugation to antibody or immunoadhesin through its amino acid side chains, carbohydrate chains, or reactive groups introduced on antibody or immunoadhesin by chemical modification. For example, a drug may be attached through the ε-amino group of a lysine residue, through a free α-amino group, by disulfide exchange to a cysteine residue, or by oxidation of the 1,2-diols in a carbohydrate chain with periodic acid to allow attachment of drugs containing various nucleophiles through a Schiff-base linkage. See, for example, U.S. Pat. No. 4,256,833. Protein modifying agents include amine-reactive reagents (e.g., reactive esters, isothiocyantates, aldehydes, and sulfonyl halides), thiol-reactive reagents (e.g., haloacetyl derivatives and maleimides), and carboxylic acid- and aldehyde-reactive reagents. CD20 antagonist or antibody polypeptides can be covalently joined to peptidic agents through the use of bifunctional cross-linking reagents. Heterobifunctional reagents are more commonly used and permit the controlled coupling of two different proteins through the use of two different reactive moieties (e.g., amine-reactive plus thiol, iodoacetamide, or maleimide). The use of such linking agents is well known in the art. See, for example, U.S. Pat. No. 4,671,958. Peptidic linkers can also be employed. In the alternative, the antibody or immunoadhesin can be linked to a peptidic moiety through preparation of a fusion polypeptide.

Examples of further bifunctional protein coupling agents include N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Alternatively, a fusion protein comprising the antibody/immunoadhesin and agent may be made, e.g. by recombinant techniques or peptide synthesis.

Other modifications of the antibody or immunoadhesin are contemplated herein. For example, the antibody immunoadhesin may be linked to one of a variety of nonproteinaceous polymers, e.g., polyethylene glycol, polypropylene glycol, polyoxyalkylenes, or copolymers of polyethylene glycol and polypropylene glycol.

The antibody or immunoadhesin disclosed herein may also be formulated as liposomes. Liposomes containing the antagonist or antibody are prepared by methods known in the art, such as described in Epstein et al. *Proc. Natl. Acad. Sci. USA,* 82:3688 (1985); Hwang et al. *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19): 1484 (1989).

Amino acid sequence modification(s) of the antibody or immunoadhesin are contemplated. For example, it may be desirable to improve the binding affinity and/or other biological properties of the antibody or immunoadhesin. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by different residue. The sites of greatest interest for substitutional mutagenesis of antibody antibodies include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), His(H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody or immunoadhesin. Such altering includes deleting one or more carbohydrate moieties found in the antibody, and/or adding one or more glycosylation sites that are not present in the antibody or immunoadhesin.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original protein (for O-linked glycosylation sites).

Where the protein comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd) concerning a CD20 antibody composition. Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US Pat. Appl. No. US 2003/0157108 A1, Presta, L; WO 00/61739A1; WO01/29246A1; US2003/0115614A1; US2002/0164328A1; US2004/0093621A1; US2004/0132140A1; US2004/0110704A1; US2004/0110282A1; US2004/0109865A1; WO03/085119A1; WO03/084570A1; WO2005/035778; WO2005/035586 (describing RNA inhibition (RNAi) of fucosylation); Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Nucleic acid molecules encoding amino acid sequence variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version.

It may be desirable to modify the antibody or immunoadhesin of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of an antibody antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered that has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. Nos. 6,194,551B1, 6,242,195B1, 6,528,624B1 and 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues). Substitution of one or more residues at positions 326, 327, 333 and/or 334 can improve C1q binding and/or CDC function.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln No. US2002/0004587 A1, Miller et al.).

VII. Pharmaceutical Formulations

Therapeutic formulations of the antibodies or immunoadhesins used in accordance with the present invention are prepared for storage by mixing an antibody or immunoadhesin having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystalized forms of the antibody or immunoadhesin are also contemplated. See, for example, US 2002/0136719A1 (Shenoy et al.).

The formulation herein may also contain more than one active compound as necessary for the particular indication being treated, preferably those with complementary activities that do not adversely affect each other. For example, it may be desirable to further provide a second medicament, such as those discussed in the Treatment Section below. The type and effective amounts of such other agents depend, for example, on the amount of antibody present in the formulation, the type of autoimmune disease being treated, and clinical parameters of the subjects. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

VIII. Treatment of Autoimmune Disease Subjects

The invention herein provides a method of treating a subject with an autoimmune disease comprising: administering a therapeutic antibody, immunoadhesin, or other biologic drug to the subject to treat an autoimmune disease; obtaining a biological sample from the subject; affinity purifying immunoglobulins from the biological sample; and subjecting the purified immunoglobulins to a neutralizing antibody assay. Preferably, the biological sample is serum, and may have been found to contain interference that interferes with the performance of a neutralizing antibody assay.

Various autoimmune diseases that can be treated herein are described above in the definition section. Exemplary preferred autoimmune diseases include autoimmune rheumatologic disorders (such as rheumatoid arthritis (RA), Sjogren's syndrome, scleroderma, lupus such as SLE and lupus nephritis, polymyositis/dermatomyositis cryoglobulinemia, antiphospholipid antibody syndrome, psoriatic arthritis), autoimmune gastrointestinal and liver disorders (such as inflammatory boweldiseases (e.g., ulcerative colitis and Crohn's disease), autoimmune gastritis and pernicious anemia, autoimmune hepatitis, primary biliary cirrhosis, primary sclerosing cholangitis, celiac disease), vasculitis (ANCA-associated vasculitis, Churg-Strauss vasculitis, Wegener's granulomatosis, and polyarteriitis), autoimmune neurological disorders (such as multiple sclerosis, opsoclonus myoclonus syndrome, myasthenia gravis, neuromyelitis optica, parkinson's, Alzheimer's disease, autoimmune polyneuropathies), renal disorders (glomerulonephritis, Goodpasture's syndrome, Berger's disease), autoimmune dermatologic disorders (psoriasis, urticaria, pemphigus vulgaris, bullous pemphigoid, cutaneous lupus erythematosus), hematologic disorders (thrombocytopenic purpura, thrombotic thrombocytopenic purpura, post-transfusion purpura, autoimmune hemolytic anemia), atherosclerosis, uveitis, autoimmune hearing diseases such as inner ear disease and hearing loss, Behcet's disease, Raynaud's syndrome, organ transplant, and autoimmune endocrine disorders (diabetic-related autoimmune diseases, Addison's disease, autoimmune thyroid disease (Graves' disease, thyroiditis). More preferred autoimmune indications include rheumatoid arthritis (RA), SLE, ulcerative colitis, ANCA-associated vasculitis, lupus, multiple sclerosis, Sjogren's syndrome, Graves' disease, IDDM, pernicious anemia, thyroiditis, and glomerulonephritis, with RA and SLE being most preferred for the purposes herein.

The preferred therapeutic antibody herein is an antibody which binds to a B-cell surface marker, most preferably a CD20 antibody, most preferably a chimeric, humanized, or human CD20 antibody, more preferably rituximab, humanized 2H7, 2F2 (HuMax-CD20) human CD20 antibody (Genmab), humanized A20 antibody (Immunomedics), anti-CD20 auristatin E conjugate (Seattle Genetics), anti-CD20-IL2 (EMD/Biovation/City of Hope), anti-CD20 MAb therapy (EpiCyte), or anti-CD20 antibody TRU 015 (Trubion), etc. Still more preferred is rituximab or humanized 2H7.

Other therapeutic antibodies or immunoadhesins of interest herein include: rituximab, humanized 2H7, 2F2 (HuMax-CD20) human CD20 antibody, humanized A20 antibody or IMMU-106, TRU 015, tumor necrosis factor (TNF)-α antibody, infliximab, CDP571, MAK-195, adalimumab, pegylated TNF-α antibody fragment, CDP-870, anti-TNF-α polyclonal antibody, PassTNF, integrin antibody, efalizumab, natalizumab, BAFF antibody, BR3 antibody, BAFF receptor antibody, Blys antibody, belimumab, CD37 antibody, TRU 016, CD22 antibody, epratuzumab, Abiogen CD22 antibody, CMC 544, combotox, BL22, LIF 226, VEGF antibody, VEGF receptor antibody, bevacizumab, anti-HER antibody, trastuzumab, pertuzumab, cetuximab, anti-IgE antibody, omalizumab, IL-21 antibody, Impheron anti-B cell antibody, 1D09C3, Lym-1 antibody, oncolym, ISF 154, gomiliximab, IL-6 receptor antibody, atlizumab, IL-15 antibody, HuMax-Il-15, chemokine receptor antibody, CCR2 antibody, MLN1202, anti-complement antibody, C5 antibody, eculizuma, oral formulation of human immunoglobulin, IgPO, IL-12 antibody, ABT-874, teneliximab, CD40 antibody, humanized S2C6, TNX 100, CD52 antibody, campath-1H, and αvβ3 antibody.

Where the antibody is a CD20 antibody, such as Rituximab or humanized 2H7, the antibody may be dosed as 1 gm×2, 375 mg/m²×4, etc. Preferably, two or more antibody exposures are given, for example approximately every 6 months, or approximately every 12 months.

The antibody is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated (see, e.g., US Patent Appln No. 2002/0009444, Grillo-Lopez, A, concerning intrathecal delivery of a CD20 antibody). Preferably, the dosing is given intravenously or subcutaneously.

While the therapeutic antibody, immunoadhesin or other biologic may be administered as a single-agent to treat the autoimmune disease, generally, the therapeutic antibody or immunoadhesin will be combined with one or more second medicament(s). For example, for RA, and other autoimmune diseases, the antibody; immunoadhesin, or other biologic drug is preferably combined with any one or more of the immunosuppressive agents, chemotherapeutic agents, BAFF antagonists, integrin antagonists or antibodies, and/or cytokines listed in the definitions section above; any one or more disease-modifying antirheumatic drugs (DMARDs), such as hydroxycloroquine, sulfasalazine, methotrexate, leflunomide, azathioprine, D-penicillamine, Gold (oral), Gold (intramuscular), minocycline, cyclosporine; Staphylococcal protein A immunoadsorption; intravenous immunoglobulin (IVIG); nonsteroidal antiinflammatory drugs (NSAIDs); glucocorticoid (e.g. via joint injection); corticosteroid (e.g. methylprednisolone and/or prednisone); folate; an anti-tumor necrosis factor (TNF) antagonist, e.g. etanercept/ENBREL™, infliximab/REMICADE™, D2E7 (Knoll) or CDP-870 (Celltech); IL-1R antagonist (e.g. Kineret); IL-10 antagonist (e.g. Ilodecakin); a blood clotting modulator (e.g. WinRho); an IL-6 antagonist/anti-TNF (CBP 1011); CD40 antagonist (e.g. IDEC 131); Ig-Fc receptor antagonist (MDX33); immunomodulator (e.g. thalidomide or Immu-Dyn); anti-CD5 antibody (e.g. H5g1.1); macrophage inhibitor (e.g. MDX 33); costimulatory blocker (e.g. BMS 188667 or Tolerimab); complement inhibitor (e.g. h5G1.1, 3E10 or an anti-decay accelerating factor (DAF) antibody); IL-2 antagonist (zxSMART); EGFR inhibitor (see definition above); tyrosine kinase inhibitor (see definition above); anti-angiogenic agent (e.g. VEGF antibody such as bevacizumab); CD22 antibodies such as LL2 or epratuzumab (LYMPHO-CIDE®; Immunomedics), including epratuzumab Y-90 (Juweid et al. Cancer Res 55(23 Suppl):5899s-5907s (1995)), Abiogen's CD22 antibody (Abiogen, Italy), CMC 544 (Wyeth/Celltech), combotox (UT Soutwestern), BL22 (NIH), and LympoScan Tc99 (Immunomedics); EpCAM antibody such as 17-1A (PANOREX®); αvβ3 antibody (e.g. VITAXIN®; Medimmune); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody Y-90 (USC); LIF 226 (Enhanced Lifesci.); BAFF antibody (e.g., WO 03/33658); BAFF receptor antibody (e.g., WO 02/24909); BR3 antibody; Blys antibody such as belimumab; LYMPHOSTAT-B™; anti-Lym-1 Oncolym (USC/Peregrine); ISF 154 (UCSD/Roche/Tragen); gomilixima (Idec 152; Biogen Idec); IL-6 receptor antibody such as atlizumab (ACTEMRA™; Chugai/Roche); IL-15 antibody such as HuMax-Il-15 (Genmab/Amgen); chemokine receptor antibody, such as a CCR2 antibody (e.g. MLN1202; Millieneum); anti-complement antibody, such as C5 antibody (e.g. eculizumab, 5G1.1; Alexion); oral formulation of human immunoglobulin (e.g. IgPO; Protein Therapeutics); IL-12 antibody such as ABT-874 (CAT/Abbott); Teneliximab (BMS-224818); B cell vaccine; DN-BAFF (Xencor); CRx-119 (CombinatoRx); Amgen's BAFF antagonist; Pentostatin (Pfizer); IC-485 (ICOS); chemokine antagonist such as T-487 (Tularik) or Reticulose (AVR-118); SCO-323 (SCIOS); integrin antagonist 683699, Tanabe, NGD-2001-1 (Neurogen); SCIO-469 (SCIOS); BIRB-796 (Boehringer Ingelheim); VX702, VX850 (Vertex); Leukotriene B-4 antagonist (such as amelubunt, BIIL-284; BI); microtubule modulator (Paxceed; Angiotech); protease inhibitor (MBS561392; BMS); AGIX-4207 (Atherogenics); ISIS-104838 (ISIS/Elan); MFG-IRAP (Univ. Pitt.); IL-1 Trap (RGN-303; Regeneron/Novartis); oprelvekin (Wyeth); everolimus (Certican; Novartis); Amevive (Biogen Idec); ORG-39141 (Organon); FK-506 (Fujisawa); IL-2 antagonist (tacrolimus; Fujisawa); etc.

The second medicament may be administered with the initial exposure and/or later exposures of the therapeutic antibody or immunoadhesin, such combined administration includes co-administration, using separate formulations or a single pharmaceutical formulation, and consecutive administration in either order, wherein preferably there is a time period while both (or all) active agents simultaneously exert their biological activities.

Aside from administration of the antibody or immunoadhesin directly to the subject the present application contemplates administration of antibodies or immunoadhesins by gene therapy. Such administration of nucleic acid encoding the antibody is encompassed by the expression administering an "effective amount" of an antibody. See, for example, WO96/07321 published Mar. 14, 1996 concerning the use of gene therapy to generate intracellular antibodies.

There are two major approaches to getting the nucleic acid (optionally contained in a vector) into the subject's cells; in vivo and ex vivo. For in vivo delivery the nucleic acid is injected directly into the subject, usually at the site where the antibody is required. For ex vivo treatment, the subject's cells are removed, the nucleic acid is introduced into these isolated cells and the modified cells are administered to the subject either directly or, for example, encapsulated within porous membranes that are implanted into the subject (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins that bind to a cell surface membrane protein associated with endocytosis may be used for targeting and/or to facilitate uptake, e.g. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

IX. Diagnostic Kits

The present invention also provides a diagnostic kit, or article of manufacture, for use with the pretreatment method herein. The diagnostic kit may comprise any one or more of the following: antagonist/antibody/drug reference material (e.g. rituximab reference material); positive control neutralizing antibody (preferably goat of cyno monkey); Protein A+G column (e.g. Protein A/G column); delipidation reagent; immunoglobulin affinity purification buffer(s) (for example binding, elution and neutralization buffers); complement serum; assay diluent for cells; instruction manual or literature; vial of frozen cells (for example, WIL2 cells); cell labeling reagent (such as CELL TITER GLO®), etc.

For example, the diagnostic kit may comprise (a) delipidation reagent; (b) buffers (e.g. binding and elution buffers) for affinity purification of immunoglobulins; and (c) instruction manual instructing the user of the diagnostic kit to use the kit to pre-treat a biological sample from an autoimmune disease subject prior to conducting a cell based bioassay (such as a neutralizing antibody assay) on the sample (e.g. to avoid the problem of serum interference). Optionally, the biological sample has been treated with a drug, such as a therapeutic antibody or immunoadhesin.

The diagnostic kit optionally further comprises any one or more of: drug reference material, positive control neutralizing antibody, complement serum, assay diluent for cells, and cell labeling reagent, etc.

Further details of the invention are illustrated by the following non-limiting Example. The disclosures of all citations in the specification are expressly incorporated herein by reference.

EXAMPLE 1

Neutralizing Antibody Assay, with Serum Pretreatment

This example concerns the development of a neutralizing antibody assay for a CD20 antibody, rituximab, in autoimmune indications. Rituximab is a human-mouse chimeric monoclonal antibody, which recognizes human CD20 molecule on B-cells, and depletes B-cells through antibody effector functions. Rituximab is approved in the US and Europe for indolent relapsed non-Hodgkin's lymphoma (NHL), and is being developed for autoimmune indications, including rheumatoid arthritis (RA) and systemic lupus erythematosis (SLE), among others.

An assessment of sero-positive neutralizing antibody (NAb) activity against Rituximab was developed based on the potency assay, a complement-dependent cell cytotoxicity (CDC) assay. In this assay, the Rituximab is incubated with a standardized source of human serum complement and a target B lymphocyte cell line, WIL2-S, for 2 hours. After 2 hours the amount of cells killed by Rituximab-CDC is measured in proportion to the amount of live cells remaining.

Reagents

Delipidation reagent: PHM-L LIPOSORB® Absorbent, Calbiochem, cat524371
IMMUNOPURE™ Immobilized Protein A/G: Pierce, cat 20422
5 mL Polypropylene Columns: Pierce, cat 29922
Elution buffer: HCl in sterile ddH$_2$O, pH 2.1
Neutralization buffer: 20×PBS, A410, (without Ca$^{++}$/Mg$^{++}$), pH 6.5, HyClone cat SH3A648.01
Blocking buffer: 1% BSA in PBS
BSA: 7.5% BSA, Fraction V, cell culture tested, Sigma cat A8412
PBS: GNE B5 Media Prep, code A0829

CENTRICON-30® concentrator: 2 mL size, Amicon cat 4209
Centrifuge for de-lipidation: EPPENDORF® Centrifuge 5415C
Centrifuge for cells and concentration: Beckman GS-6R
WIL2-S cells (ATCC CRL-8885)
Growth medium: RPMI 1640, 2 mM L-glutamine, 10% FBS, gentamicin
Assay Diluent (AD): RPMI 1640, 20 mM HEPES, 0.1% BSA, 25 ug/mL gentamicin.
Starvation medium: 10% Growth Medium in AD
Complement: Human complement serum, Quidel part A112, lot 3MO174
Rituximab standard: reference material C2B81298-2, 9.8 mg/mL.
Rituximab NAb standard: Cyno anti-Rituxan pAb (lot 44082-81), 0.5 mg/mL
Rituximab NAb control: $NHS_{pool}$ containing NAb (low and high titer, lot 44083-48)
CELLTITER-GLO®: Promega, cat G7571 (10×10 mL vials)
GUAVA® VIACOUN™: GUAVA® Inc. 4000-0040
96-well white TC plates, clear bottom with lid: Corning costar 3610
Molecular Devices SOFTMAX® Pro Lmax reader
Pierce iCON™ concentrator, 7 mL size, cat-89886 (alternative to CENRICON-30®)
Pierce IMMUNOPURE® Protein A Plus (cat 22811) (alternative to Protein A/G)
Pierce IMMUNOPURE® immobilized Protein G Plus (cat 22851) (alternative to Protein A/G)

Sample Pre-Treatment Procedure

1. Delipidate the serum. Add 200 µL LIPOSORB® (reconstituted in PBS, according to manufacturer's instructions) solution to 0.25 mL serum in a siliconized 1.5 mL polypropylene tube. Vortex for 45 seconds and centrifuge for 10 minutes at 4500 rpm (1600×g). Remove and dilute the supernatant into 1 mL of PBS in a siliconized 1.5 mL polypropylene tube. (It is acceptable if some LIPOSORB® carries over into the sample; it does not clog the column.)
2. Prepare a separate 0.5 mL Protein A/G column for each patient sample, and controls. Add 1 mL of Protein A/G slurry to a 5 mL column, and measure the bed height to ensure a 0.5 mL bed volume.
3. If the gel has been previously used, run 5 mL of Elution buffer through column to clean column beads. The number of times the columns can be re-used has not been determined.
4. Equilbrate the column using 2×5 mL of PBS.
5. Apply the 1.25 mL of diluted serum to the column. Collect the flow through in a siliconized 1.5 mL polypropylene tube, and re-apply twice.
6. Wash column using 3×5 mL PBS.
7. Elute antibody with 4 mL of Elution buffer into a 15 mL FALCON® tube containing 0.2 mL of Neutralization buffer.
8. Block a 2 mL CENTRICON-30® concentrator by adding 0.5 mL of Blocking buffer and centrifuging the concentrator for 10 min at 3000 rpm (1000×g). Discard any Blocking buffer remaining at the top or bottom of the concentrator.
9. Concentrate the neutralized eluants until a final volume of 0.25 mL is achieved. If the sample is over-concentrated, use the CENTRICON-30® flow through to dilute back to 0.25 mL. Use a siliconized 1.5 mL polypropylene tube to measure the final volume to the 0.25 mL mark.
10. Store the concentrate −70° C. until ready to test in the neutralization CDC assay.

Neutralization Assay Procedure

The neutralizing antibody assay herein was based on that disclosed in US2005/0032130 A1 (Beresini and Song), published Feb. 10, 2005. However, the assay was modified in the following respects: The biological sample (i.e. serum) is now pre-treated serum; CELLTITER-GLO® is now the assay readout instead of ALAMAR BLUE™ (resazurin); control antibody used is a cynomolgus monkey Protein A purified (HER2 adsorbed) preparation, not goat anti-Rituximab; and buffers, volumes, complement, controls, serum matrix effects, data analysis and interpretation have changed as described below.

1. The day before the assay, seed $8\times10^6$ cells in 20 mL of starvation media ($0.4\times10^6$ cells/mL).
2. Prepare 100 ($CDC_{max}$), 0.4 ($CDC_{NAb}$) and 0 ($CDC_{zero}$) µg/mL Rituximab.
   100 µg/mL: 10.2 µL Rituximab Standard to 1 mL AD
   20 µg/mL: 150 µL 100 µg/mL Rituximab in 600 µL AD
   0.4 µg/mL: 100 µL 20 µg/mL Rituximab in 4.9 mL AD
   0 µg/mL: AD alone
3. Add 25 µl to assay wells as shown below (Table 3).

TABLE 3

Plate layout of Rituximab concentrations

| | | | | | | | | | |
|---|---|---|---|---|---|---|---|---|---|
| 0.4 | 0.4 | 0.4 | 0.4 | 0.4 | 0.4 | 0.4 | 0.4 | 0.4 | 0.4 |
| 0.4 | 0.4 | 0.4 | 0.4 | 0.4 | 0.4 | 0.4 | 0.4 | 0.4 | 0.4 |
| 0.4 | 0.4 | 0.4 | 0.4 | 0.4 | 0.4 | 0.4 | 0.4 | 0.4 | 0.4 |
| 0.4 | 0.4 | 0.4 | 0.4 | 0.4 | 0.4 | 0.4 | 0.4 | 0.4 | 0.4 |
| 0.4 | 0.4 | 0.4 | 0.4 | 0.4 | 0 | 0 | 0 | 0 | 100 |
| 0.4 | 0.4 | 0.4 | 0.4 | 0.4 | 0 | 0 | 0 | 0 | 100 |

4. Add 25 µL each in duplicate of negative control, low control, and samples as shown in Table 4. The current plate layout has space for 24 samples. It may be possible to use more of the plate, but this has not been tested.

TABLE 4

Plate layout of controls and samples

| NEG | NEG | LO | RA1 | RA2 | RA3 | RA4 | RA5 | RA6 | RA7 |
|---|---|---|---|---|---|---|---|---|---|
| NEG | NEG | LO | RA1 | RA2 | RA3 | RA4 | RA5 | RA6 | RA7 |
| RA8 | RA9 | RA10 | RA11 | RA12 | RA13 | RA14 | RA15 | RA16 | RA17 |
| RA8 | RA9 | RA10 | RA11 | RA12 | RA13 | RA14 | RA15 | RA16 | RA17 |
| RA18 | RA19 | RA20 | RA21 | RA22 | RA23 | RA24 | RA25 | NEG | NEG |
| RA18 | RA19 | RA20 | RA21 | RA22 | RA23 | RA24 | RA25 | NEG | NEG |

5. Incubate with gentle agitation at RT for at least 2 hrs to allow serum purified antibodies to bind and neutralize Rituximab.
6. Thaw complement serum at room temperature (RT) and then place on ice.
7. Remove WIL2-S cells from flask, washing down sides of flask, into a 50 mL falcon tube. Remove 10 µl of cell suspension and add 190 µl of VIACOUNT®. After 2 min. count cells and record #/mL (20× dilution) and % viability. Alternatively, cells can be counted using a hemocytometer.
8. Spin cells down at 1200 rpm (150×g), for 8 min. Decant media and resuspend cells in 1 mL AD. Prepare 10-20 mL of WIL2-S cells in AD at $0.25\times10^6$/mL for the assay.
9. Add 50 µl of complement to each well.
10. Add 50 µl of $0.25\times10^6$/mL WIL2-S cells prepared in step 9 to each well.

11. Agitate plate to mix for 1 min. at RT. Incubate for 2 hrs at 37° C./5% $CO_2$. In the last 10 min. bring plate to RT.
12. Allow CELLTITER-GLO® reagent to come to RT. Add 100 μl to each well. CELLTITER-GLO® buffer and substrate are stored at −20° C. The two components can be put at 4-8° C. overnight to thaw, and on the assay day, mixed and left on the benchtop 30-45 min. before using. Extra mixed reagent can be stored at −20° C. for at least 1 month.
13. Agitate plate to mix for 10 min. at RT.
14. Read luminescence on Molecular Devices LMAX® reader, using an integration time of 1 second, no blank subtraction.

Data Analysis

1. Calculate the mean values from the assay replicates for all samples, and controls. Do not use values if the % CV of the means is >25%.
2. Calculate the cutpoint as follows:

(Mean Negative Control CELLTITER-GLO® Value at 0.4 μg/mL Rituximab)×1.03

A cupoint of the assay is defined as the level of response of the assay above which a sample is defined to be positive and below which it is defined to be negative. Th eupoint is determined statistically from the level of non-specific background in the assay as described in (Mire-Sluis et al. *Journal of Immunological Methods* 289: 1-16 (2004)). In this assay, the cutpoint factor of 1.03 was determined by assaying 10 RA individual naïve serums over 3 days, and represents a 3% increase over the intra-assay negative control response. The 10 RA individual serums were selected from a population of 100 individuals, to reflect the full range of serum interferences and non-specific effects. The serum pre-treament procedure, performed as part of each assay, normalized the sample responses and enabled the low cutpoint factor of 1.03 to be applied. Using the cutpoint factor of 1.03, all Rituximab naïve RA serums would be defined as negative, while 1 μg/ml cynomolgus monkey anti-Rituximab pAb, or 0.25 μg/mL goat anti-Rituximab pAb would be defined as positive.
3. Examine sample mean values and report according to the following criteria:
   If sample mean value≦cutpoint, report sample as negative
   If sample mean value>cutpoint, report sample as positive
4. The assay is valid if the ratio of the low control falls>cutpoint, and if there is a 10-fold drop in signal between the 0 μg/mL and 100 μg/mL Rituximab assay responses.
5. At the present time, samples are reported as positive or negative, based on the intra-assay cutpoint. In the future it may be desired to calculate the titer values of samples. "Titer" is is the reciprocol of the highest dilution of the sample that tests positive in the method. It is a common practice to express titer as the common logarithm of the highest dilution of the sample that tests positive in the method. (Mire-Sluis et al. *Journal of Immunological Methods* 289: 1-16 (2004)). If this were done, a high titer control would also be included.

Interpolation of Titer

The titer of a sample is defined as the log10 of the dilution factor of the sample that results in an assay response equivalent to the cutpoint in the assay. Therefore, if a 1/100 dilution of a sample results in a signal in the assay equivalent to the cutpoint, the titer would be $\log_{10} 100$ or 2.00. A sample requiring a 1/1000 dilution would be assigned a titer of 3.00. If the cutpoint response falls between two dilution responses of a sample (which it generally does), the titer is calculated using a formula to solve for an unknown point on a line on an X-Y axis, given all of the Y points are known ("signal units"), and two of the X points are known ("dilution units").

The following formula is used:
Let a=the signal of the positive sample or control above the cutpoint
Let b=the signal of the positive sample or control below the cutpoint
Let c=the signal of the cutpoint
Let d=the dilution of the positive sample or control signal above the cutpoint
Let e=the dilution of the positive sample or control signal below the cutpoint To calculate the titer:

$$\text{Titer} = \log(a-c) \cdot (e-d) + d(a-b)$$

6. The assay is valid if the ratio of the low control falls>1.03, and the high control titer>2.0.
7. Samples are reported as a neturalizing activity titer value. If the sample response at 0 μg/mL Rituximab indicates assay interference, report data as "not determined due to interfering substances".

WIL2-S Cell Passaging

1. The Rituximab-CDC neutralization assay uses the immortal WIL2-S, B lymphoblast cell line as the target cell. This cell line is optimally passaged after reaching a density of $1-2 \times 10^6$ cells/mL. For maintaining the cells, the new seeding density should target $0.04-0.3 \times 10^6$ cells/mL in growth media. To prepare for a CDC assay, the cells are seeded at a density of $0.4 \times 10^6$ cells/mL in assay diluent containing 10% growth media. The cells can be passaged at least until P31. Ideally, the cells should be maintained at a cell density of $0.25-2.5 \times 10^6$ cells/mL.

TABLE 5

Seeding of WIL2-S cells for passaging

| Number of days before re-passage | # cells input/20 mL growth media |
|---|---|
| 2 | $6 \times 10^6$ |
| 3 | $1.6 \times 10^6$ |
| 4 | $8 \times 10^5$ |

Results and Discussion

The Rituximab CDC neutralizing antibody assay is depicted schematically in FIG. 4. FIG. 5 shows Rituximab complement-dependent cytotoxicity (CDC) can be neutralized at both the Fab and Fc domains. Rituximab mediates CDC in a dose-dependent manner, with maximal cell lysis occurring at a concentration of 5 μg/mL (control data shown as circles). In order to test the ability of this assay to detect neutralizing antibodies, Rituximab was pre-incubated with goat anti-human Fcγ (data shown as diamonds) or goat anti-Rituximab (CDR-specific; data shown as squares) polyclonal antibodies. After 2 hours, normal human serum complement and 12,500 cells were added. After 2 hours, the number of live cells was measured using CELLTITER GLO® In the presence of either anti-CDR or Fc antibodies the potency of Rituximab-CDC activity was reduced, indicated by shifts in the dose-response curves to the right. For example, as indicated by the arrows, the percentage of live cells remaining at 1 µg/mL Rituximab, is greatest in samples pre-incubated with goat anti-CDR (100%), followed by samples pre-incubated with goat anti-Fcγ (70%), compared to the control (40%).

The first step in changing from a potency to neutralizing assay format is testing the ability of the assay to tolerate untreated, drug-naïve serum. Initial testing of the Rituximab-CDC assay in the presence of normal human serum showed equivalent dose-dependent performance among 20 male and female individuals. However, among the NAb assay target population, rheumatoid arthritis (RA) patients, the assay was unreliable, demonstrating highly variable Rituximab-CDC cellular responses between individuals. In some individuals, the addition of naïve serum to the assay completely inhibited the ability of Rituximab to mediate CDC.

FIG. 6 shows serum tolerance in the Rituximab-CDC Assay. The Rituximab-CDC assay was tested for its ability to tolerate untreated, drug-naïve serum. Initial testing of the assay in the presence of normal human serum showed equivalent dose-dependent performance among 10 male and female individuals (left plot). However, among the NAb assay target population, rheumatoid arthritis (RA) patients, the assay was unreliable, demonstrating highly variable Rituxan-CDC cellular responses between individuals (right plot). In some individuals, the addition of naïve serum to the assay completely inhibited the ability of Rituxan to mediate CDC (e.g. individual's data shown as diamonds).

The lack of assay specificity and variability of Rituximab potency in the presence of RA serum, so called "serum interference", led to the addition of a serum pre-treatment step, to "clean-up" the sample before subjecting it to the Rituximab CDC assay.

The methods tested for serum pre-treatment were developed with increasing levels of manipulation.

First, although the interference could be minimized by increasing the minimum sample dilution (to at least 1/80), the sensitivity of the assay was compromised too greatly (>5 µg/mL anti-Rituximab antibody).

Second, several alternative assay read-outs were compared. In this assay, the amount of CDC caused by Rituximab could be measured by the number of live cells remaining or the number of cells killed. Live cells are typically measured by a metabolic readout, such as the redox indicator ALAMAR BLUE™ or the ATP indicator, CELLTITER GLO™. Killed cells can be measured by the release of cytoplasmic contents, either endogenous (e.g. lactose dehydrogenase), or a pre-loaded dye (e.g. calcein). Conceptually, if a reagent gave an assay read-out after 10 minutes (e.g. CELLTITER GLO™), compared to 1.6 hours (e.g. ALAMAR BLUE™) there would be less time for serum to non-specifically interfere with the cell metabolism. Or, if a reagent was exogenously added, and therefore unconnected to the cell metabolism (e.g. calcein) there may be less interference.

FIG. 7 represents alternative assay read-outs for the Rituximab-CDC assay. The amount of cell lysis caused by Rituximab-CDC could be measured by the number of live cells remaining or the number of cells killed. Live cells are typically measured by a metabolic readout, such as the redox indicator ALAMAR BLUE™ or the ATP indicator, CELLTITER GLO®. Killed cells can be measured by the release of cytoplasmic contents, either endogenous (e.g. lactose dehydrogenase) or a pre-loaded dye (e.g. calcein). ALAMAR BLUE™ (data shown in x's) and CELLTITER GLO™ (data shown in circles) demonstrated similar Rituximab-CDC profiles, with an improved dynamic range evident for CELLTITER GLO®. Calcein (data shown in squares) was also able to measure Rituximab-CDC, albeit with less sensitivity and a smaller dynamic range. Lactose dehydrogenase (data shown in diamonds) was not a sensitive indicator of Rituximab-CDC.

FIG. 8 is a comparison of RA serum interference in the Rituximab-CDC assay when using different read-outs. In an effort to reduce rheumatoid arthritis serum interference in the Rituximab-CDC assay, the tolerance of three different CDC assay readouts (see FIG. 7) to five individual RA serums was tested. Serum interference was observed with all three detection reagents, CELLTITER GLO®, ALAMAR BLUE™ (middle plot), and calcein. CELLTITER GLO® was selected as the readout for future assay development as it showed the least serum inteference, best dynamic range, and most uniformly sensitive Rituximab $EC_{50}$.

As shown in FIGS. 7 and 8, in this assay, alternative read-outs did not solve the RA serum interference, suggesting the interference occurs early on in the assay, during the 2 hours the cells are incubated with Rituximab and standardized complement serum. Unfortunately, alternative suitable functional MOA assays for Rituximab, or alternative pathways for CDC measurement are not available.

A third line of approach was to remove the interfering substance. Two fairly gentle methods initially tested included: a desalting column (NAP-5™ column, Pharmacia Biotech) to remove small molecules; and a de-lipidation procedure (PHM-L LIPOSORB™ Calbiochem) to remove serum lipids. Neither method was able to remove the interfering substance. A third possibility, would be to add an inhibitory antibody against, or heat-inactivate, an interfering cytokine. However, although cytokine profiles of the patient RA serum were not normal, they did not demonstrate a correlation between particular cytokine levels and assay interference. A crude way of preferentially precipitating total immunoglobulins is to "salt them out" by adding saturated ammonium sulphate (SAS) to a final 33% volume. Sample interference was still an issue after the SAS procedure. Finally, it was believed that it would be necessary to specifically purify the serum immunoglobulins before assaying samples in the Rituximab-CDC assay.

Specific purification of serum immunoglobulins could be carried out by (a) specifically purifying anti-Rituximab antibodies, or (b) specifically purifying total immunoglobulins.

The purification of anti-Rituximab antibodies appeared to be the most direct approach, with the added benefit of capture of all anti-drug antibody isotypes and removal of Rituximab interference caused by residual therapeutic drug in the patient samples. Several Rituximab-affinity purification strategies were tested including: Rituximab-GLY-CPG™ (Controlled Pore Glass Products Inc.), Rituximab-BIOMAG® (Bangs Laboratories, Inc.) and Rituximab-EMPORE™ (3M Bioanalytical Technologies). After extensive optimization of coupling, blocking, binding and elution parameters, these methods were discontinued due to low recovery, particularly at serum specific antibody concentrations less than 1 µg/ML (<25% recovery).

A classical method for the purification of total immunoglobulins is the use of the recombinant proteins of microbial origin, Protein A and Protein G. Protein G binds strongly to all four IgG subtypes ($IgG_1$, $IgG_2$, $IgG_3$ and $IgG_4$), whereas Protein A binds strongly to $IgG_1$, $IgG_2$ and $IgG_4$, weakly to $IgG_3$, IgM, IgA, and moderately to IgE. A combination of both the Protein A and Protein G properties will capture all anti-drug antibody isotypes, albeit with a bias towards the $IgG_{1,2,4}$ subtypes. Using this approach, neutralizing activity of antibodies to Rituximab were equivalent in normal human serum and pre-treated normal human serum in the CDC assay. Importantly, the dose-responsiveness of the Rituximab-CDC activity became equivalent in the pre-treated serum of RA individuals (individuals demonstrating extremes of CDC assay variability in untreated serum). The low sensitivity of neutralization activity was determined to be 0.25 μg/mL and 1 μg/mL (neat serum concentration) of goat and cynomolgus monkey anti-Rituximab antibodies, respectively. Finally, a procedure using Protein A+G purification prior to assaying seropositive anti-Rituximab antibody samples in the cell-based Rituximab-CDC assay was developed, optimized and qualified. Assay performance characteristics were found to be acceptable for a validated clinical antibody characterization assay.

Figure 9:
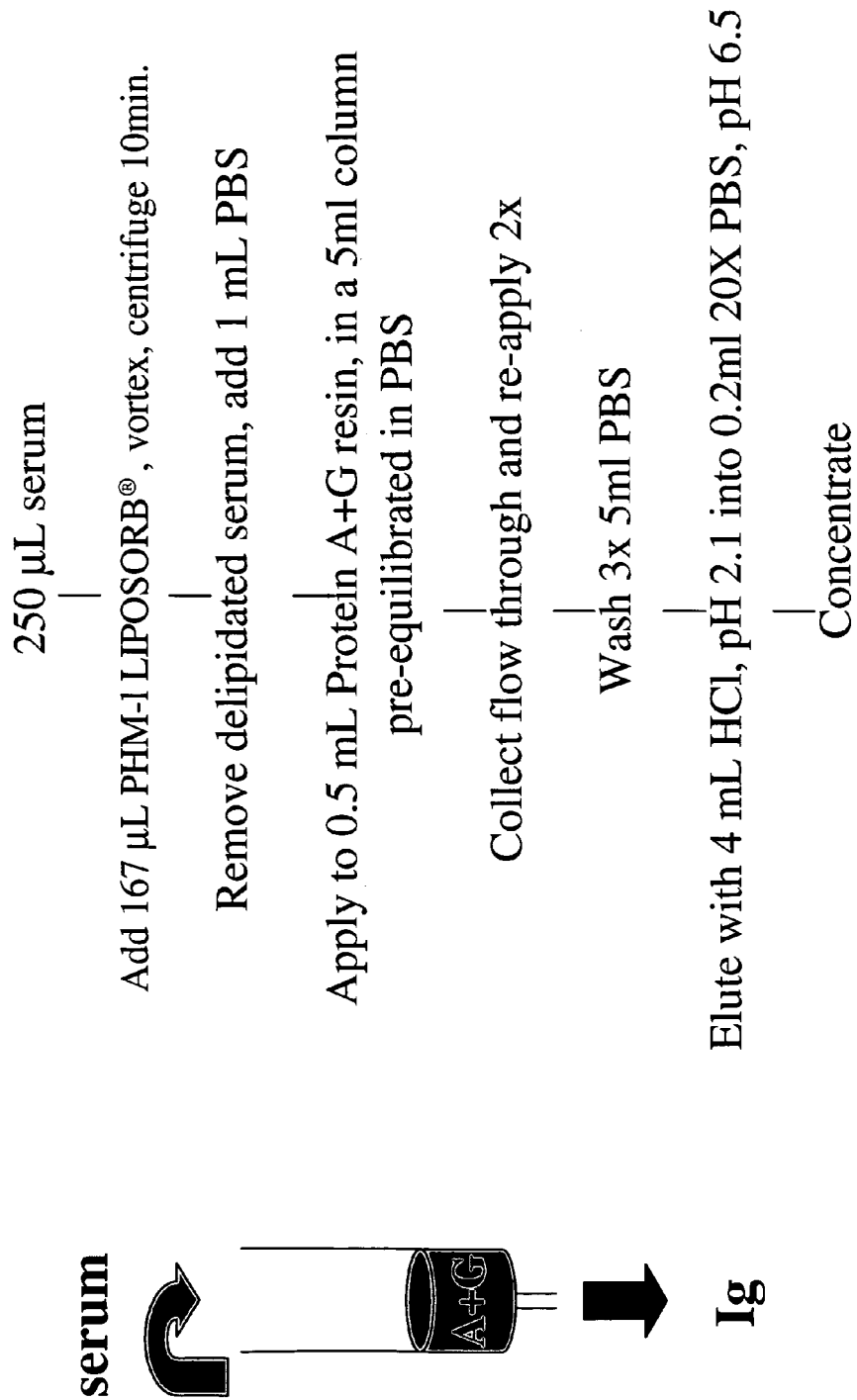
FIG. 9 illustrates a preferred procedure for serum pre-treatment herein.

FIG. 9 shows the serum pre-treatment procedure used to purify total immunoglobulins from the serum sample. This method for the purification of total serum immunoglobulins was developed to eliminate serum interference in the Rituximab-CDC assay. A flowchart summarizing the procedure is shown in this figure.

Figure 10:
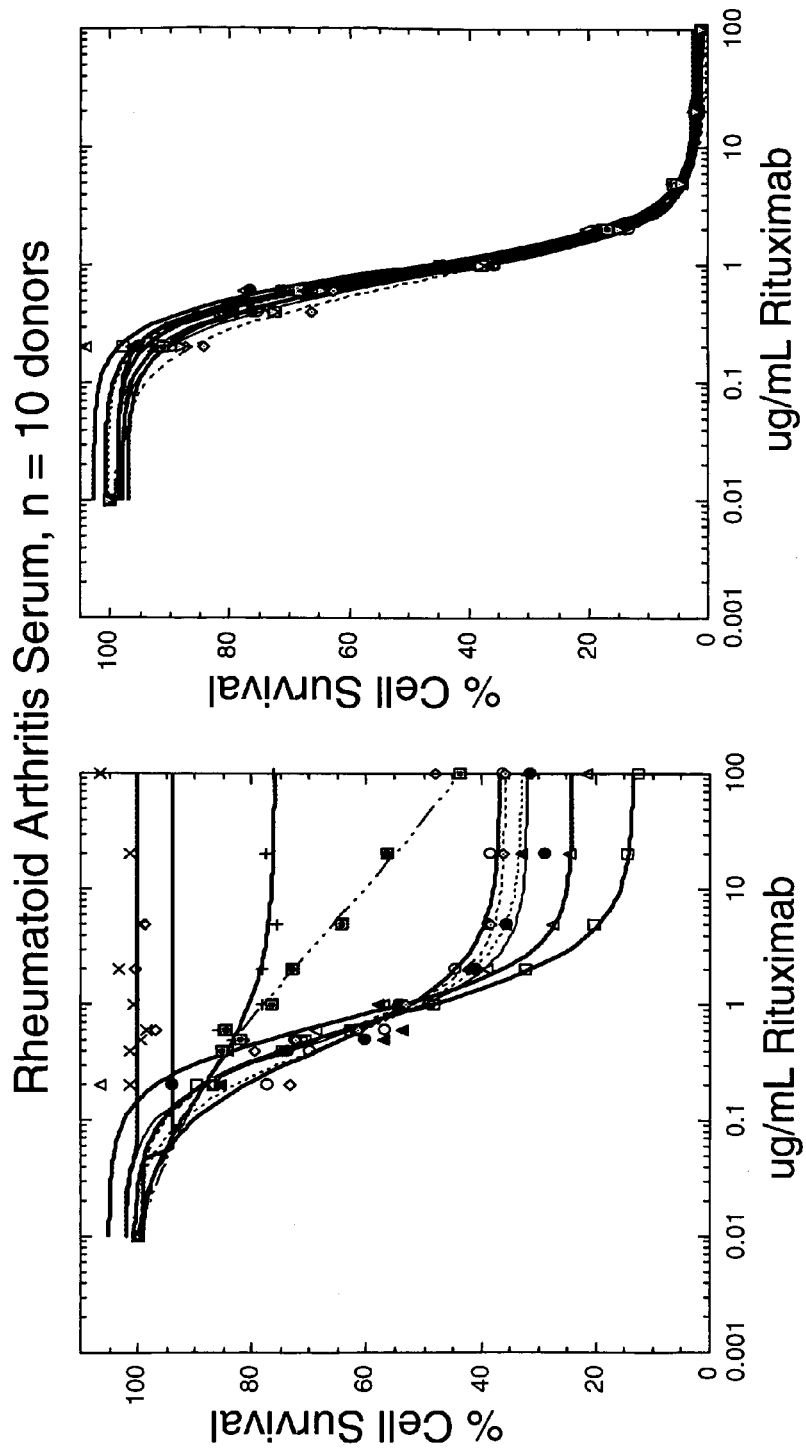
FIG. 10 shows the effect of serum pre-treatment on readout from RA serum without serum pretreatment (left) and with serum pretreatment (right).

The serum pre-treatment procedure overcame the problem of interference. FIG. 10 shows the performance of the Rituximab-CDC assay before and after serum pre-treatment procedure. Among the NAb assay target population, rheumatoid arthritis (RA) patients, the Rituximab-CDC assay was unreliable, demonstrating highly variable Rituxan-CDC cellular responses between individuals (left plot). Ten individual RA serums were tested in the assay before (left plot) and after (right plot) performing the serum pre-treatment procedure. Serum pre-treatment removed the interfering matrix components and normalized the dose-responsiveness of the Rituxan-CDC activity between RA individuals.

Aside from the serum pre-treatment procedure various additional improvements in the neutralizing antibody assay were also developed.

Figure 11:
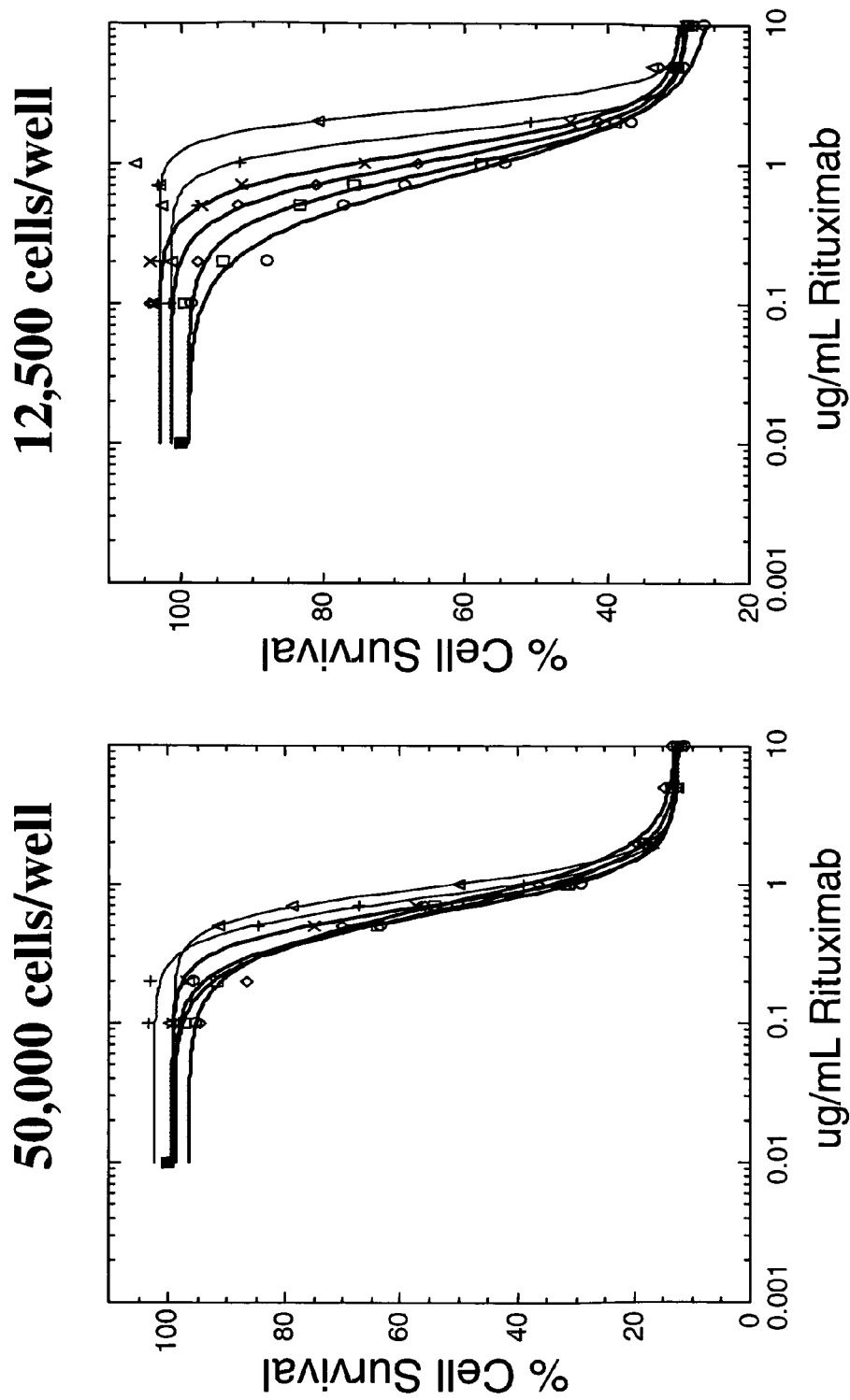
FIG. 11 depicts the effect of varying the cell number used in the NAb assay.

The sensitivity of the assay using different cell numbers was assessed. FIG. 11 shows higher sensitivity of the Rituximab-CDC assay to neutralization at lower cell numbers. The Rituximab-CDC potency assay, used for material lot release, was adapted as a neutralization assay. During neutralization assay optimization, improved sensitivity was observed using 4-fold lower cell numbers (right plot) than used in the potency assay (left plot), while maintaining assay robustness. Increasing concentrations of goat anti-Rituximab CDR polyclonal antibodies, from 0.125-2 μg/mL, were pre-incubated with Rituximab over the full dose-response range of the assay. The rightward shift of the dose-response curve increased in a manner directly proportional to the concentration of pAb directed against Rituximab (left and right plots). The rightward shift was greater at lower cell numbers (right plot). Also, it was observed that at all neutralizing antibody concentrations the shift compared to the control was non-linear, shifting to a greater extent at lower concentrations of Rituximab (upper sections of the left and right plots).

Figure 12:
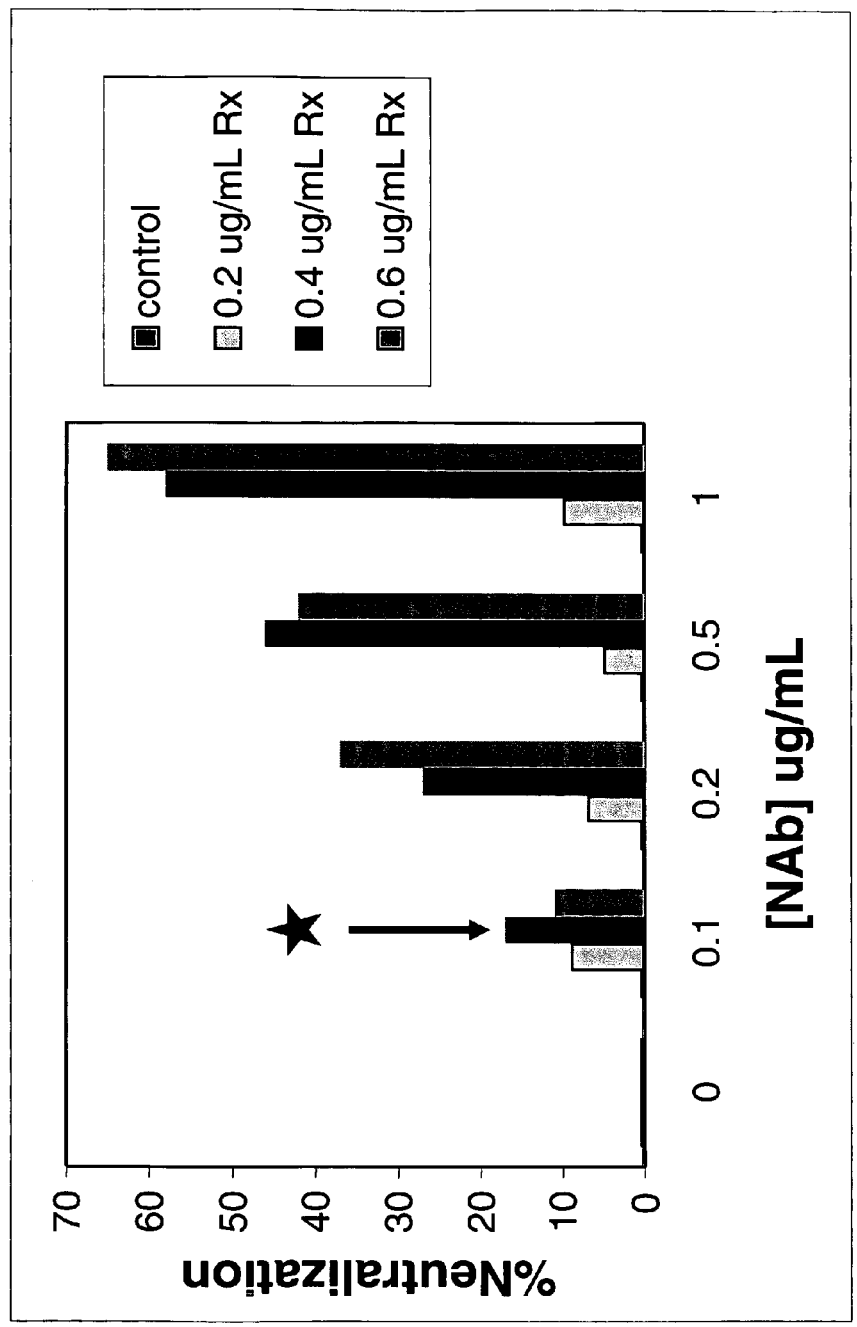
FIG. 12 represents rituximab dose selection, sensitivity to NAb.

Rituximab dose selection was also evaluated as a further means for improving the sensitivity of the neutralizing antibody assay. FIG. 12 reflects selection of the Rituximab concentration used to assess neutralizing activity. In the evaluation of patient samples it is desired to report the neutralizing activity at a single, selected concentration of Rituximab relative to a cutpoint. Based on the improved sensitivity of the Rituximab dose-response curve to neutralization at lower Rituximab concentrations (FIG. 12), the Rituximab concentration was tested at 0.2, 0.4 and 0.6 μg/mL with increasing amounts of goat anti-Rituximab CDR pAb (from 0.1-1 μg/mL). At a Rituximab concentration of 0.2 μg/mL, the CDC activity is only marginally above background cell lysis in the absence of drug, and neutralization is below a statistical significance. At a Rituximab concentration of 0.4 μg/mL, the CDC activity is 25-30% above background cell lysis in the absence of drug, and neutralization is statistical significant, and proportional to the neutralizing antibody concentration. Further increases in Rituximab concentrations, compromised the sensitivity of the assay to detect lower levels of neutralizing antibodies. For example, as pointed out by the star above, 0.1 μg/mL of goat anti-Rituximab CDR pAb does not neutralize 0.6 μg/mL as well as 0.4 μg/mL Rituximab.

Figure 13:
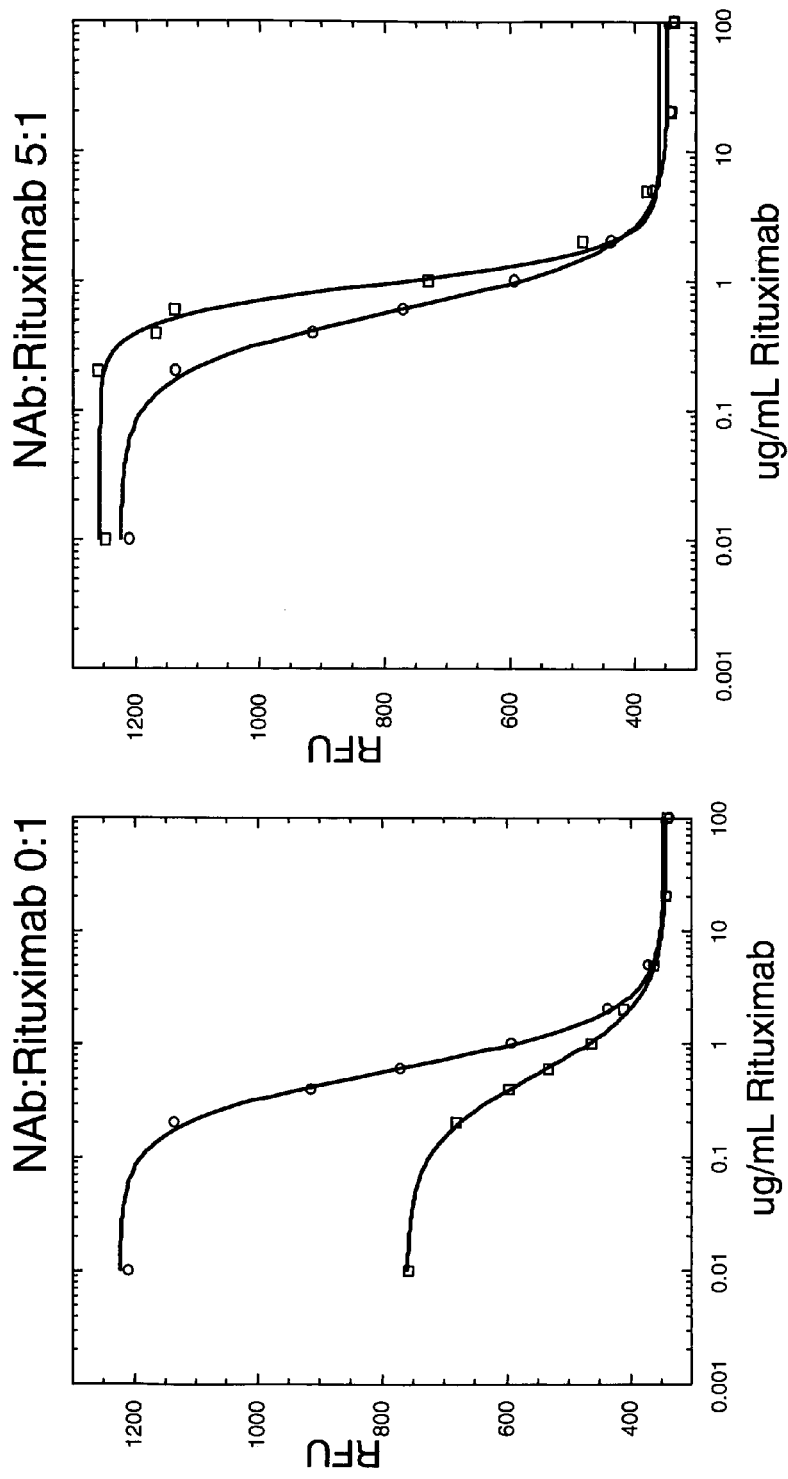
FIG. 13 shows drug interference in NAb assay with NAb:Rituxan ratios of 0:1 (left) or 5:1 (right).

FIG. 13 shows the effect of drug interference on the neutralizing Rituximab-CDC assay. Patient serum for testing in the neutralizing Rituximab-CDC assay may contain residual therapeutic Rituximab. If the levels of neutralizing antibodies are insufficient to biologically inactive circulating therapeutic, the sample may contribute active Rituximab to the assay, resulting in abnormally high CDC activity. Neutralizing activity in the assay is evaluated against intra-assay negative and low positive controls. Abnormally high CDC activity in a sample would result in a false negative readout. The plot on the left shows the effect of adding 1 μg/mL Rituximab (squares) to the normal assay Rituximab dose-response curve (circles). The baseline toxicity is higher, and the $EC_{50}$ shifts to a lower apparent concentration. However, as depicted in the plot to the right, when the same 1 μg/mL Rituximab concentration is added along with a 5-fold molar excess (5 μg/mL) of goat anti-Rituximab CDR polyclonal antibody (squares), the baseline toxicity returns to normal, and there is still enough neutralizing antibody in excess of Rituximab to be measured positive in the assay (as indicated by a significant rightward shift in the dose-response curve).

What is claimed is:

1. A method of treating a biological sample from an autoimmune disease subject comprising:
   (a) delipidating the sample;
   (b) affinity purifying immunoglobulins in the sample;
   (c) concentrating the purified immunoglobulins; and
   (d) subjecting the concentrated immunoglobulins to a cell-based biological activity assay in the presence of a drug with which the subject has been treated.

2. The method of claim 1 wherein the assay in (d) is a neutralizing antibody assay.

3. The method of claim 1 wherein the sample in (a) is a serum sample.

4. The method of claim 1 wherein the subject has rheumatoid arthritis.

5. The method of claim 1 wherein the subject has systemic lupus erythematosis (SLE).

6. The method of claim 1 wherein step (b) comprises purifying essentially all immunoglobulin isotypes.

7. The method of claim 1 wherein step (b) comprises Protein A+G affinity purification.

8. The method of claim 7 wherein the Protein A+G affinity purification is repeated two or more times.

9. The method of claim 8 wherein the Protein A+G affinity purification is repeated three times.

10. The method of claim 2 wherein the sample, prior to step a), interferes with the performance of the neutralizing antibody assay.

11. The method of claim 1 wherein the autoimmune disease subject has been treated with a therapeutic antibody or immunoadhesin.

12. The method of claim 11 wherein the autoimmune disease subject has been treated with a therapeutic antibody.

13. The method of claim 12 wherein the therapeutic antibody is a CD20 antibody.

14. The method of claim 13 wherein the therapeutic antibody is rituximab or humanized 2H7.

15. The method of claim 12 wherein the therapeutic antibody is selected from the group consisting of rituximab, humanized 2H7, 2F2 (HuMax-CD20) human CD20 antibody, humanized A20 antibody or IMMU-106, TRU 015, tumor necrosis factor (TNE)-α antibody, infliximab, CDP571, MAK-195, adalimumab, pegylated TNE-α antibody fragment, CDP-870, anti-TNF-α polyclonal antibody, PassTNF, integrin antibody, efalizumab, natalizumab, BAFF antibody, BR3 antibody, BAFF receptor antibody, Blys antibody, belimumab, CD37 antibody, TRU 016, CD22 antibody, epratuzumab, Abiogen CD22 antibody, CMC 544, combotox, BL22, LIF 226, VEGF antibody, VEGF receptor antibody, bevacizumab, ranibizumab, anti-HER antibody, trastuzumab, pertuzumab, cetuximab, anti-IgE antibody, omalizumab, IL-21 antibody, Impheron anti-B cell antibody, 1D09C3, Lym-1 antibody, oncolym, ISF 154, gomiliximab, IL-6 receptor antibody, atlizumab, IL-15 antibody, HuMax-Il-15, chemokine receptor antibody, CCR2 antibody, MLN1202, anti-complement antibody, C5 antibody, eculizuma, oral formulation of human immunoglobulin, IgPO, IL-12 antibody, ABT-874, teneliximab, CD40 antibody, humanized S2C6, TNX 100, CD52 antibody, campath-1H, and αvβ3 antibody.

16. The method of claim 12 wherein the therapeutic antibody is an integrin antibody.

17. The method of claim 16 wherein the integrin antibody is efalizumab or natalizumab.

18. The method of claim 11 wherein the autoimmune disease subject has been treated with an immunoadhesin.

19. The method of claim 18 wherein the immunoadhesin is selected from the group consisting of BR3-Ig, TNE-α immunoadhesin, etanercept, anti-BAFF peptibody, TACI-Ig, BCMA-Ig, CTLA4-Ig, abatacept, and BAFF-R-Ig.

20. The method of claim 11 wherein the autoimmune disease subject has been treated with a tumor necrosis factor (TNF)-α antibody or a TNF-α immunoadhesin.

21. The method of claim 20 wherein the autoimmune disease subject has been treated with infliximab, adalimumab, etanercept, CDP-870 or D2E7.

22. The method of claim 1 wherein the autoimmune disease subject has been treated with a drug selected from the group consisting of pegylated soluble TNF-R, pegsunercept, IL-1 receptor antagonist (IL-1Ra), anakira, DN-BAFF, and vaccine.

* * * * *

UNITED STATES PATENT AND TRADEMARK OFFICE
CERTIFICATE OF CORRECTION

PATENT NO. : 7,601,335 B2  Page 1 of 1
APPLICATION NO. : 11/437296
DATED : October 13, 2009
INVENTOR(S) : McCutcheon et al.

It is certified that error appears in the above-identified patent and that said Letters Patent is hereby corrected as shown below:

In column 90, line 58, claim 15, please delete "(TNE)-α" and insert --(TNF)-α--.

In column 90, line 59, claim 15, please delete "TNE-α" and insert --TNF-α--.

In column 91, line 16, claim 19, please delete "TNE-α" and insert --TNF-α--.

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,601,335 B2 |
| APPLICATION NO. | : 11/437296 |
| DATED | : October 13, 2009 |
| INVENTOR(S) | : McCutcheon et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 307 days.

Delete the phrase "by 307 days" and insert -- by 454 days --

Signed and Sealed this

Twenty-second Day of June, 2010

David J. Kappos
*Director of the United States Patent and Trademark Office*

SEQUENCE LISTING

<160> NUMBER OF SEQ ID NOS: 24

<210> SEQ ID NO 1
<211> LENGTH: 107
<212> TYPE: PRT
<213> ORGANISM: Mus musculus

<400> SEQUENCE: 1

```
Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Ser Val Ser
                20                  25                  30
```

```
Tyr Met His Trp Tyr Gln Gln Lys Pro Gly Ser Ser Pro Lys Pro
             35                  40                  45

Trp Ile Tyr Ala Pro Ser Asn Leu Ala Ser Gly Val Pro Ala Arg
         50                  55                  60

Phe Ser Gly Ser Gly Ser Gly Thr Ser Tyr Ser Leu Thr Ile Ser
     65                  70                  75

Arg Val Glu Ala Glu Asp Ala Ala Thr Tyr Tyr Cys Gln Gln Trp
             80                  85                  90

Ser Phe Asn Pro Pro Thr Phe Gly Ala Gly Thr Lys Leu Glu Leu
             95                 100                 105

Lys Arg

<210> SEQ ID NO 2
<211> LENGTH: 107
<212> TYPE: PRT
<213> ORGANISM: Artificial sequence
<220> FEATURE:
<223> OTHER INFORMATION: sequence is synthesized

<400> SEQUENCE: 2

Asp Ile Gln Met Thr Gln Ser Pro Ser Ser Leu Ser Ala Ser Val
  1               5                  10                  15

Gly Asp Arg Val Thr Ile Thr Cys Arg Ala Ser Ser Ser Val Ser
             20                  25                  30

Tyr Met His Trp Tyr Gln Gln Lys Pro Gly Lys Ala Pro Lys Pro
             35                  40                  45

Leu Ile Tyr Ala Pro Ser Asn Leu Ala Ser Gly Val Pro Ser Arg
         50                  55                  60

Phe Ser Gly Ser Gly Ser Gly Thr Asp Phe Thr Leu Thr Ile Ser
     65                  70                  75

Ser Leu Gln Pro Glu Asp Phe Ala Thr Tyr Tyr Cys Gln Gln Trp
             80                  85                  90

Ser Phe Asn Pro Pro Thr Phe Gly Gln Gly Thr Lys Val Glu Ile
             95                 100                 105

Lys Arg

<210> SEQ ID NO 3
<211> LENGTH: 108
<212> TYPE: PRT
<213> ORGANISM: Artificial Sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
             20                  25                  30

Asn Tyr Leu Ala Trp Tyr Gln Gln Lys Pro Gly Lys Ala Pro Lys
             35                  40                  45

Leu Leu Ile Tyr Ala Ala Ser Ser Leu Glu Ser Gly Val Pro Ser
         50                  55                  60

Arg Phe Ser Gly Ser Gly Ser Gly Thr Asp Phe Thr Leu Thr Ile
     65                  70                  75

Ser Ser Leu Gln Pro Glu Asp Phe Ala Thr Tyr Tyr Cys Gln Gln
             80                  85                  90

Tyr Asn Ser Leu Pro Trp Thr Phe Gly Gln Gly Thr Lys Val Glu
```

Ile Lys Arg

<210> SEQ ID NO 4
<211> LENGTH: 10
<212> TYPE: PRT
<213> ORGANISM: Mus musculus

<400> SEQUENCE: 4

Arg Ala Ser Ser Val Ser Tyr Met His
 1               5                  10

<210> SEQ ID NO 5
<211> LENGTH: 7
<212> TYPE: PRT
<213> ORGANISM: Mus musculus

<400> SEQUENCE: 5

Ala Pro Ser Asn Leu Ala Ser
 1               5

<210> SEQ ID NO 6
<211> LENGTH: 9
<212> TYPE: PRT
<213> ORGANISM: Mus musculus

<400> SEQUENCE: 6

Gln Gln Trp Ser Phe Asn Pro Pro Thr
 1               5

<210> SEQ ID NO 7
<211> LENGTH: 122
<212> TYPE: PRT
<213> ORGANISM: Mus musculus

<400> SEQUENCE: 7

Gln Ala Tyr Leu Gln Gln Ser Gly Ala Glu Leu Val Arg Pro Gly
 1               5                  10                  15

Ala Ser Val Lys Met Ser Cys Lys Ala Ser Gly Tyr Thr Phe Thr
                 20                  25                  30

Ser Tyr Asn Met His Trp Val Lys Gln Thr Pro Arg Gln Gly Leu
                 35                  40                  45

Glu Trp Ile Gly Ala Ile Tyr Pro Gly Asn Gly Asp Thr Ser Tyr
                 50                  55                  60

Asn Gln Lys Phe Lys Gly Lys Ala Thr Leu Thr Val Asp Lys Ser
                 65                  70                  75

Ser Ser Thr Ala Tyr Met Gln Leu Ser Ser Leu Thr Ser Glu Asp
                 80                  85                  90

Ser Ala Val Tyr Phe Cys Ala Arg Val Val Tyr Tyr Ser Asn Ser
                 95                 100                 105

Tyr Trp Tyr Phe Asp Val Trp Gly Thr Gly Thr Thr Val Thr Val
                110                 115                 120

Ser Ser

<210> SEQ ID NO 8
<211> LENGTH: 122
<212> TYPE: PRT
<213> ORGANISM: Artificial sequence
<220> FEATURE:
<223> OTHER INFORMATION: sequence is synthesized -continued

<400> SEQUENCE: 8

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
        35                  40                  45

Glu Trp Val Gly Ala Ile Tyr Pro Gly Asn Gly Asp Thr Ser Tyr
    50                  55                  60

Asn Gln Lys Phe Lys Gly Arg Phe Thr Ile Ser Val Asp Lys Ser
65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Asn Ser
        95                  100                 105

Tyr Trp Tyr Phe Asp Val Trp Gly Gln Gly Thr Leu Val Thr Val
    110                 115                 120

Ser Ser

<210> SEQ ID NO 9
<211> LENGTH: 119
<212> TYPE: PRT
<213> ORGANISM: Artificial Sequence
<220> FEATURE:
<223> OTHER INFORMATION: sequence is synthesized

<400> SEQUENCE: 9

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
        35                  40                  45

Glu Trp Val Ala Val Ile Ser Gly Asp Gly Gly Ser Thr Tyr Tyr
    50                  55                  60

Ala Asp Ser Val Lys Gly Arg Phe Thr Ile Ser Arg Asp Asn Ser
65                  70                  75

Lys Asn Thr Leu Thr Leu Gln Met Asn Ser Leu Arg Ala Glu Asp
            80                  85                  90

Thr Ala Val Tyr Tyr Cys Ala Arg Gly Arg Val Gly Tyr Ser Leu
        95                  100                 105

Tyr Asp Tyr Trp Gly Gln Gly Thr Leu Val Thr Val Ser Ser
    110                 115

<210> SEQ ID NO 10
<211> LENGTH: 10
<212> TYPE: PRT
<213> ORGANISM: Mus musculus

<400> SEQUENCE: 10

Gly Tyr Thr Phe Thr Ser Tyr Asn Met His
1               5                   10

<210> SEQ ID NO 11
<211> LENGTH: 17
<212> TYPE: PRT
<213> ORGANISM: Mus musculus

```
<400> SEQUENCE: 11

Ala Ile Tyr Pro Gly Asn Gly Asp Thr Ser Tyr Asn Gln Lys Phe
  1               5                  10                  15

Lys Gly

<210> SEQ ID NO 12
<211> LENGTH: 13
<212> TYPE: PRT
<213> ORGANISM: Mus musculus

<400> SEQUENCE: 12

Val Val Tyr Tyr Ser Asn Ser Tyr Trp Tyr Phe Asp Val
  1               5                  10

<210> SEQ ID NO 13
<211> LENGTH: 213
<212> TYPE: PRT
<213> ORGANISM: Artificial sequence
<220> FEATURE:
<223> OTHER INFORMATION: sequence is synthesized

<400> SEQUENCE: 13

Asp Ile Gln Met Thr Gln Ser Pro Ser Ser Leu Ser Ala Ser Val
  1               5                  10                  15

Gly Asp Arg Val Thr Ile Thr Cys Arg Ala Ser Ser Ser Val Ser
                 20                  25                  30

Tyr Met His Trp Tyr Gln Gln Lys Pro Gly Lys Ala Pro Lys Pro
                 35                  40                  45

Leu Ile Tyr Ala Pro Ser Asn Leu Ala Ser Gly Val Pro Ser Arg
                 50                  55                  60

Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Gln Gln Trp
                 80                  85                  90

Ser Phe Asn Pro Pro Thr Phe Gly Gln Gly Thr Lys Val Glu Ile
                 95                 100                 105

Lys Arg Thr Val Ala Ala Pro Ser Val Phe Ile Phe Pro Pro Ser
                110                 115                 120

Asp Glu Gln Leu Lys Ser Gly Thr Ala Ser Val Val Cys Leu Leu
                125                 130                 135

Asn Asn Phe Tyr Pro Arg Glu Ala Lys Val Gln Trp Lys Val Asp
                140                 145                 150

Asn Ala Leu Gln Ser Gly Asn Ser Gln Glu Ser Val Thr Glu Gln
                155                 160                 165

Asp Ser Lys Asp Ser Thr Tyr Ser Leu Ser Ser Thr Leu Thr Leu
                170                 175                 180

Ser Lys Ala Asp Tyr Glu Lys His Lys Val Tyr Ala Cys Glu Val
                185                 190                 195

Thr His Gln Gly Leu Ser Ser Pro Val Thr Lys Ser Phe Asn Arg
                200                 205                 210

Gly Glu Cys

<210> SEQ ID NO 14
<211> LENGTH: 452
<212> TYPE: PRT
<213> ORGANISM: Artificial sequence
<220> FEATURE:
<223> OTHER INFORMATION: sequence is synthesized
```

<400> SEQUENCE: 14

```
Glu Val Gln Leu Val Glu Ser Gly Gly Gly Leu Val Gln Pro Gly
  1               5                  10                 15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Asp Thr Ser Tyr
             50                  55                  60

Asn Gln Lys Phe Lys Gly Arg Phe Thr Ile Ser Val Asp Lys Ser
 65                  70                  75

Lys Asn Thr Leu Tyr Leu Gln Met Asn Ser Leu Arg Ala Glu Asp
             80                  85                  90

Thr Ala Val Tyr Tyr Cys Ala Arg Val Val Tyr Tyr Ser Asn Ser
             95                 100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Glu Lys Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
```

-continued

```
                380                 385                 390
Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 15
<211> LENGTH: 213
<212> TYPE: PRT
<213> ORGANISM: Artificial sequence
<220> FEATURE:
<223> OTHER INFORMATION: sequence is synthesized

<400> SEQUENCE: 15

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
                20                  25                  30

Tyr Leu His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
        50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Trp
            80                  85                  90

Ala Phe Asn Pro Pro Thr Phe Gly Gln Gly Thr Lys Val Glu Ile
                95                 100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 16
<211> LENGTH: 452
<212> TYPE: PRT
<213> ORGANISM: Artificial sequence
<220> FEATURE:
<223> OTHER INFORMATION: sequence is synthesized

<400> SEQUENCE: 16
```

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Ala Thr Ser Tyr
         50                  55                  60

Asn Gln Lys Phe Lys Gly Arg Phe Thr Ile Ser Val Asp Lys Ser
         65                  70                  75

Lys Asn Thr Leu Tyr Leu Gln Met Asn Ser Leu Arg Ala Glu Asp
         80                  85                  90

Thr Ala Val Tyr Tyr Cys Ala Arg Val Val Tyr Ser Tyr Arg
         95                 100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ala Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Ala Ala Leu Pro Ala Pro Ile Ala Ala Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390
```

```
Gln Pro Glu Asn Asn Tyr Lys Thr Thr Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 17
<211> LENGTH: 451
<212> TYPE: PRT
<213> ORGANISM: Artificial sequence
<220> FEATURE:
<223> OTHER INFORMATION: sequence is synthesized

<400> SEQUENCE: 17

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
             20                  25                  30

Ser Tyr Asn Met His Trp Val Arg Gln Ala Pro Gly Lys Gly Leu
             35                  40                  45

Glu Trp Val Gly Ala Ile Tyr Pro Gly Asn Gly Asp Thr Ser Tyr
             50                  55                  60

Asn Gln Lys Phe Lys Gly Arg Phe Thr Ile Ser Val Asp Lys Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Val Val Tyr Tyr Ser Asn Ser
             95                 100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225

Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
```

```
                275                 280                 285

Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Glu Lys Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly

<210> SEQ ID NO 18
<211> LENGTH: 107
<212> TYPE: PRT
<213> ORGANISM: Artificial sequence
<220> FEATURE:
<223> OTHER INFORMATION: sequence is synthesized

<400> SEQUENCE: 18

Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ser Val Ser
            20                  25                  30

Tyr Leu His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Gln Gln Trp
            80                  85                  90

Ala Phe Asn Pro Pro Thr Phe Gly Gln Gly Thr Lys Val Glu Ile
            95                  100                 105

Lys Arg

<210> SEQ ID NO 19
<211> LENGTH: 122
<212> TYPE: PRT
<213> ORGANISM: Artificial sequence
<220> FEATURE:
<223> OTHER INFORMATION: sequence is synthesized

<400> SEQUENCE: 19
```

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Ala Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Tyr Arg
                95                  100                 105

Tyr Trp Tyr Phe Asp Val Trp Gly Gln Gly Thr Leu Val Thr Val
                110                 115                 120

Ser Ser
```

<210> SEQ ID NO 20
<211> LENGTH: 451
<212> TYPE: PRT
<213> ORGANISM: Artificial sequence
<220> FEATURE:
<223> OTHER INFORMATION: sequence is synthesized

<400> SEQUENCE: 20

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Ala Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Tyr Arg
                95                  100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210
```

```
        Pro Ser Asn Thr Lys Val Asp Lys Val Glu Pro Lys Ser Cys
                    215                 220                 225

Asp Lys Thr His Thr Cys Pro Pro Cys Pro Ala Pro Glu Leu Leu
                    230                 235                 240

Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp
                    260                 265                 270

Val Ser His Glu Asp Pro Glu Val Lys Phe Asn Trp Tyr Val Asp
                    275                 280                 285

Gly Val Glu Val His Asn Ala Lys Thr Lys Pro Arg Glu Glu Gln
                    290                 295                 300

Tyr Asn Ala Thr Tyr Arg Val Val Ser Val Leu Thr Val Leu His
                    305                 310                 315

Gln Asp Trp Leu Asn Gly Lys Glu Tyr Lys Cys Lys Val Ser Asn
                    320                 325                 330

Ala Ala Leu Pro Ala Pro Ile Ala Ala Thr Ile Ser Lys Ala Lys
                    335                 340                 345

Gly Gln Pro Arg Glu Pro Gln Val Tyr Thr Leu Pro Pro Ser Arg
                    350                 355                 360

Glu Glu Met Thr Lys Asn Gln Val Ser Leu Thr Cys Leu Val Lys
                    365                 370                 375

Gly Phe Tyr Pro Ser Asp Ile Ala Val Glu Trp Glu Ser Asn Gly
                    380                 385                 390

Gln Pro Glu Asn Asn Tyr Lys Thr Thr Pro Pro Val Leu Asp Ser
                    395                 400                 405

Asp Gly Ser Phe Phe Leu Tyr Ser Lys Leu Thr Val Asp Lys Ser
                    410                 415                 420

Arg Trp Gln Gln Gly Asn Val Phe Ser Cys Ser Val Met His Glu
                    425                 430                 435

Ala Leu His Asn His Tyr Thr Gln Lys Ser Leu Ser Leu Ser Pro
                    440                 445                 450

Gly

<210> SEQ ID NO 21
<211> LENGTH: 10
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 9
<223> OTHER INFORMATION: Xaa is M or L

<400> SEQUENCE: 21

Arg Ala Ser Ser Ser Val Ser Tyr Xaa His
                5                   10

<210> SEQ ID NO 22
<211> LENGTH: 9
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 4
<223> OTHER INFORMATION: Xaa is S or A
```

```
<400> SEQUENCE: 22

Gln Gln Trp Xaa Phe Asn Pro Pro Thr
                    5

<210> SEQ ID NO 23
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 8
<223> OTHER INFORMATION: Xaa is D or A

<400> SEQUENCE: 23

Ala Ile Tyr Pro Gly Asn Gly Xaa Thr Ser Tyr Asn Gln Lys Phe
 1               5                  10                  15

Lys Gly

<210> SEQ ID NO 24
<211> LENGTH: 13
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 6
<223> OTHER INFORMATION: Xaa is N, A, Y, W or D
<220> FEATURE:
<221> NAME/KEY: Xaa
<222> LOCATION: 7
<223> OTHER INFORMATION: Xaa is S or R

<400> SEQUENCE: 24

Val Val Tyr Tyr Ser Xaa Xaa Tyr Trp Tyr Phe Asp Val
                    5                  10
```